US012753203B2

(12) United States Patent
Gray et al.

(10) Patent No.: US 12,753,203 B2
(45) Date of Patent: Oct. 6, 2026

(54) CYCLIN-DEPENDENT KINASE INHIBITORS AND METHODS OF USE

(71) Applicant: DANA-FARBER CANCER INSTITUTE, INC., Boston, MA (US)

(72) Inventors: Nathanael S. Gray, Boston, MA (US); John Hatcher, Malborough, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 18/144,534

(22) Filed: May 8, 2023

(65) Prior Publication Data

US 2023/0365620 A1 Nov. 16, 2023

Related U.S. Application Data

(63) Continuation of application No. 16/965,674, filed as application No. PCT/US2019/017747 on Feb. 13, 2019, now abandoned.

(60) Provisional application No. 62/629,751, filed on Feb. 13, 2018.

(51) Int. Cl.
*C07J 43/00* (2006.01)
*A61P 35/00* (2006.01)

(52) U.S. Cl.
CPC .................................. *C07J 43/003* (2013.01)

(58) Field of Classification Search
CPC ................................ C07J 43/003; A61P 35/00
See application file for complete search history.

(56) References Cited

U.S. PATENT DOCUMENTS

| | | | |
|---|---|---|---|
| 9,745,299 | B2 | 8/2017 | Rzymski et al. |
| 2012/0190659 | A1 | 7/2012 | Corey et al. |
| 2013/0252930 | A1 | 9/2013 | Chu et al. |

FOREIGN PATENT DOCUMENTS

| | | | |
|---|---|---|---|
| WO | 2006093993 | A1 | 9/2006 |
| WO | 2010123545 | A2 | 10/2010 |
| WO | 2017004411 | A1 | 1/2017 |

OTHER PUBLICATIONS

Zugazagoitia et al., "Current Challenges in Cancer Treatment," Clin. Ther. Jul. 2016;38(7):1551-66. PMID: 27158009. (Year: 2016).*

Clement et al., "Three dimensional pharmacophore modeling of human CYP17 inhibitors: Potential agents for prostate cancer therapy," J. Med. Chem., vol. 46, pp. 2345-2351 (Year: 2003).

Czako et al., "Discovery of Potent and Practical Antiangiogenic Agents Inspired by Cortistatin A," J. Am. Chem. Soc., 2009, vol. 131, pp. 9014-9019.

Koch et al., "Stille and Suzuki Cross-Coupling Reactions as Versatile Tools for Modifications at C-17 of Steroidal Skeletons—A Comprehensive Study," Adv. Synth. Catal., 2017, vol. 359, No. 5, pp. 832-840.

Koch et al., "Stille and Suzuki Cross-Coupling Reactions as Versatile Tools for Modifications at C-17 of Steroidal Skeletons—A Comprehensive Study," (Supporting Information), Adv. Synth. Catal., 2017, vol. 359, No. 5, pp. 1-110.

Lauro et al., "A facile synthesis and theoretical analysis of a steroid-cyclophanone," Letts. Org. Chem., vol. 12(9), pp. 614-621 (Year: 2015), Abstract only.

Maurya et al., "Synthesis and biological evaluation of herterocyclic analogues of pregnenolone as novel anti-osteoporotic agents," Bioorganic & Medicinal Chem. Letts., vol. 27, pp. 1390-1396 (Year: 2017).

Mohareb et al., "Synthesis of progesterone heterocyclic derivatives of potential antimicrobial activity," Acta Pharmaceutica, vol. 58(1), pp. 29-42 (Year: 2008), Abstract only.

Pelc et al., "Steroid derivatives. LX. Androstane derivatives substituted by pyrazole ring in position 17," Coll. Czech. Chem. Commun., vol. 34, pp. 442-450 (Year: 1969).

Pelish et al., "Mediator Kinase Inhibition Further Activates Super-Enhancer-Associated Genes in AML," Nature, 2015, vol. 526, No. 7572, pp. 273-276.

Silva et al., "1H-indazole and 2H-indazole derivatives of androsta-5, 16-dien-3beta-ol," Acta Crystallographica, Section C: Crystal Structure Communications, vol. 64(4), pp. 217-219 (Year: 2008), Abstract only.

Tokunaga et al., "Determination of corticoids using pyrrole. V. Studies on the colored products," Chem. Pharm. Bull., vol. 35(3), pp. 1118-1127 (Year: 1987).

Wicha et al., "Cardiotonic steroids, Part 7: Synthesis of 17beta-pyridylandrostane derivatives," Bulletin of the Polish Academy of Sciences, Chemistry, vol. 12(1-2), p. 75-83 (Year: 1984), Abstract only.

Hatcher et al., "Development of Highly Potent and Selective Steroidal Inhibitors and Degraders of CDK8", ACS Med. Chem. Lett., 2018, vol. 9, pp. 540-545.

Bragelmann, J. et al., "Pan-Cancer Analysis of the Mediator Complex Transcriptome Identifies CDK19 and CDK8 as Therapeutic Targets in Advanced Prostate Cancer", Clin. Cancer Res., 2017, vol. 23, No. 7, pp. 1829-1840.

Broude, E. V. et al., "Expression of CDK8 and CDK8-interacting Genes as Potential Biomarkers in Breast Cancer", Current Cancer Drug Targets, 2015, vol. 15, pp. 739-749.

(Continued)

*Primary Examiner* — Theodore R. Howell
(74) *Attorney, Agent, or Firm* — ArentFox Schiff LLP; Daniel W. Clarke; Shawn P. Foley

(57) ABSTRACT

Compounds of Formula (I) or pharmaceutically acceptable salts thereof are provided and methods involving compounds of Formula (I) as effective inhibitors of CDK8 and/or CDK19 are also provided.

20 Claims, 2 Drawing Sheets

(56) References Cited

OTHER PUBLICATIONS

Nakamura, A. et al., “CDK8/19 inhibition induces premature G1/S transition and ATR-dependent cell death in prostate cancer cells”, Oncotarget, 2018, vol. 9, No. 17, pp. 13474-13487
Duax, W. L. et al., “Steroid Structure and Function-II. Conformational Transmission and Receptor Binding of Medroxyprogesterone Acetate”, 1978, vol. 9, pp. 901-907.
Duax, W. L. et al., “The Fascinating Complexities of Steroid-Binding Enzymes”, Curr. Opin. Struct. Biol, 1996, vol. 6, pp. 813-823.
Pluchino, N. et al., “Effects of -5 and -4 Androgens on the Brain”, US Endocrinology, 2008, vol. 4, No. 2, pp. 118-120.

* cited by examiner

CYCLIN-DEPENDENT KINASE INHIBITORS AND METHODS OF USE

CROSS-REFERENCE TO RELATED APPLICATION

This application is a continuation of U.S. application Ser. No. 16/965,674, filed on Jul. 29, 2020, which is a national stage application, filed under 35 U.S.C. § 371, of International Application No. PCT/US2019/017747, filed Feb. 13, 2019, which claims the benefit of priority under 35 U.S.C. § 119(e) to U.S. Provisional Application No. 62/629,751, filed Feb. 13, 2018, the entire contents of which are incorporated herein by reference.

GOVERNMENT LICENSE RIGHTS

This invention was made with government support under Grant No. DK043889 awarded by the National Institutes of Health. The government has certain rights in the invention.

BACKGROUND

Cyclin-dependent kinase is a kinase family integrating multiple signaling pathways to control either cell cycle or gene transcription. CDK1, 2, 4 and 6 are the critical enzymes that drive cell cycle transition. CDK7, 9 and 12 are known enzymes that regulate transcription instead of directly promoting cell cycles.

CDK8 forms part of a mediator complex that regulates the transcriptional activity of RNA polymerase II, and thereby regulates cellular proliferation and differentiation. CDK8 has also been shown to modulate the transcriptional output from distinct transcription factors involved in oncogenic control, including the Wnt/β-catenin pathway, Notch, p53, and TGF-β. CDK8 has been found to be amplified and overexpressed in colon and gastric cancer by acting through the Wnt pathway and its key signaling molecule β-catenin. In addition, CDK8 gene expression correlates with increased mortality in breast and ovarian cancers, and is essential for cell proliferation in melanoma. Similar to CDK8, CDK19 is one of the components of this mediator co-activator complex.

Deregulation of CDKs has been shown to have a significant impact on the cell state and is frequently identified as oncogenic. Numerous selective or pan-CDK small molecule inhibitors have been identified, however, most of the known inhibitors have failed in clinic trials due to the lack of high systemic drug concentration. Accordingly, compounds with improved properties to inhibit cyclin-dependent kinases, such as CDK8 and CDK19, are needed. The present application addresses the need.

SUMMARY

In one aspect, the present application relates to a compound of Formula (I):

(I)

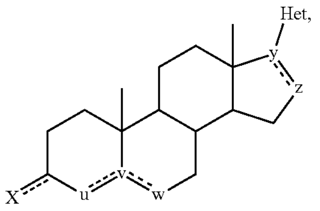

or an enantiomer, diastereomer, stereoisomer, or pharmaceutically acceptable salt thereof, wherein X, u, v, w, y, z, and Het are each defined herein, wherein the compound of Formula (I) is not a compound of Formula (AJ)

(A)

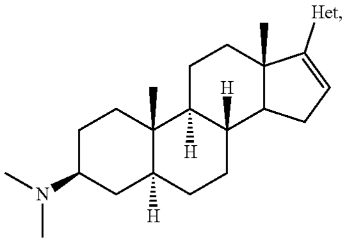

wherein Het is selected from 7-isoquinolinyl, 6-isoquinolinyl, 5-isoquinolinyl, 6-quinolinyl, and 3-pyridyl.

In another aspect, the present application relates to a pharmaceutical composition comprising a therapeutically effective amount of a compound of the application, or an enantiomer, diastereomer, stereoisomer, or pharmaceutically acceptable salt thereof, and a pharmaceutically acceptable carrier.

Another aspect of the present application relates to a method of modulating (e.g., inhibiting) a kinase (e.g., a cyclin-dependent kinase, such as CDK8 and/or CDK19). The method comprises administering to a subject in need thereof an effective amount of a compound of the application or an enantiomer, diastereomer, stereoisomer, or pharmaceutically acceptable salt thereof, or a pharmaceutical composition of the application.

Another aspect of the present application relates to a method of treating or preventing a disease (e.g., a disease in which CDK8 and/or CDK19 plays a role). The method comprises administering to a subject in need thereof an effective amount of a compound of the application or an enantiomer, diastereomer, stereoisomer, or pharmaceutically acceptable salt thereof, or a pharmaceutical composition of the application. In one aspect, the disease is a kinase (e.g., CDK8 and/or CDK19) mediated disorder. In one aspect, the disease is a proliferative disease (e.g., a proliferative disease in which CDK8 and/or CDK19 plays a role).

Another aspect of the present application relates to a method of treating or preventing cancer in a subject, wherein the cell of the cancer comprises an activated CDK8 and/or activated CDK19 or wherein the subject is identified as being in need of inhibition of CDK8 and/or CDK19 for the treatment or prevention of cancer. The method comprises administering to the subject an effective amount of a compound of the application or an enantiomer, diastereomer, stereoisomer, or pharmaceutically acceptable salt thereof, or a pharmaceutical composition of the application.

Another aspect of the present application relates to a kit comprising a compound of the application or an enantiomer, diastereomer, stereoisomer, or pharmaceutically acceptable salt thereof, or a pharmaceutical composition of the application.

Another aspect of the present application relates to a compound of the application or an enantiomer, diastereomer, stereoisomer, or pharmaceutically acceptable salt thereof, or a pharmaceutical composition of the application, for use in the manufacture of a medicament for modulating (e.g., inhibiting) a kinase (e.g., a cyclin-dependent kinase, such as CDK8 and/or CDK19), for treating or preventing a disease (e.g., a disease in which CDK8 and/or CDK19 plays a role), or for treating or preventing cancer in a subject, wherein the cell of the cancer comprises an activated CDK8 and/or activated CDK19 or wherein the subject is identified as being in need of inhibition of CDK8 and/or CDK19 for the treatment or prevention of cancer.

Another aspect of the present application relates to use of a compound of the application or an enantiomer, diastereomer, stereoisomer, or pharmaceutically acceptable salt thereof, or a pharmaceutical composition of the application, in the manufacture of a medicament for modulating (e.g., inhibiting) a kinase (e.g., a cyclin-dependent kinase, such as CDK8 and/or CDK19), for treating or preventing a disease (e.g., a disease in which CDK8 and/or CDK19 plays a role), or for treating or preventing cancer in a subject, wherein the cell of the cancer comprises an activated CDK8 and/or activated CDK19 or wherein the subject is identified as being in need of inhibition of CDK8 and/or CDK19 for the treatment or prevention of cancer.

Another aspect of the present application relates to a compound of the application or an enantiomer, diastereomer, stereoisomer, or pharmaceutically acceptable salt thereof, or a pharmaceutical composition of the application, for use in modulating (e.g., inhibiting) a kinase (e.g., a cyclin-dependent kinase, such as CDK8 and/or CDK19), in treating or preventing a disease (e.g., a disease in which CDK8 and/or CDK19 plays a role), or in treating or preventing cancer in a subject, wherein the cell of the cancer comprises an activated CDK8 and/or activated CDK19 or wherein the subject is identified as being in need of inhibition of CDK8 and/or CDK19 for the treatment or prevention of cancer.

Another aspect of the present application relates to use of a compound of the application or an enantiomer, diastereomer, stereoisomer, or pharmaceutically acceptable salt thereof, or a pharmaceutical composition of the application, in modulating (e.g., inhibiting) a kinase (e.g., a cyclin-dependent kinase, such as CDK8 and/or CDK19), in treating or preventing a disease (e.g., a disease in which CDK8 and/or CDK19 plays a role), or in treating or preventing cancer in a subject, wherein the cell of the cancer comprises an activated CDK8 and/or activated CDK19 or wherein the subject is identified as being in need of inhibition of CDK8 and/or CDK19 for the treatment or prevention of cancer.

The present application provides inhibitors of CDK8 and/or CDK19 that are therapeutic agents in the treatment or prevention of diseases such as cancer and metastasis.

The present application further provides compounds and compositions with an improved efficacy and/or safety profile relative to known inhibitors of CDK8 and/or CDK19.

The details of the disclosure are set forth in the accompanying description below. Although methods and materials similar or equivalent to those described herein can be used in the practice or testing of the present application, illustrative methods and materials are now described. In the case of conflict, the present specification, including definitions, will control. In addition, the materials, methods, and examples are illustrative only and are not intended to be limiting. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs.

The contents of all references (including literature references, issued patents, published patent applications, and co-pending patent applications) cited throughout this application are hereby expressly incorporated herein in their entireties by reference. The references cited herein are not admitted to be prior art to the application.

DETAILED DESCRIPTION

Figure 1:
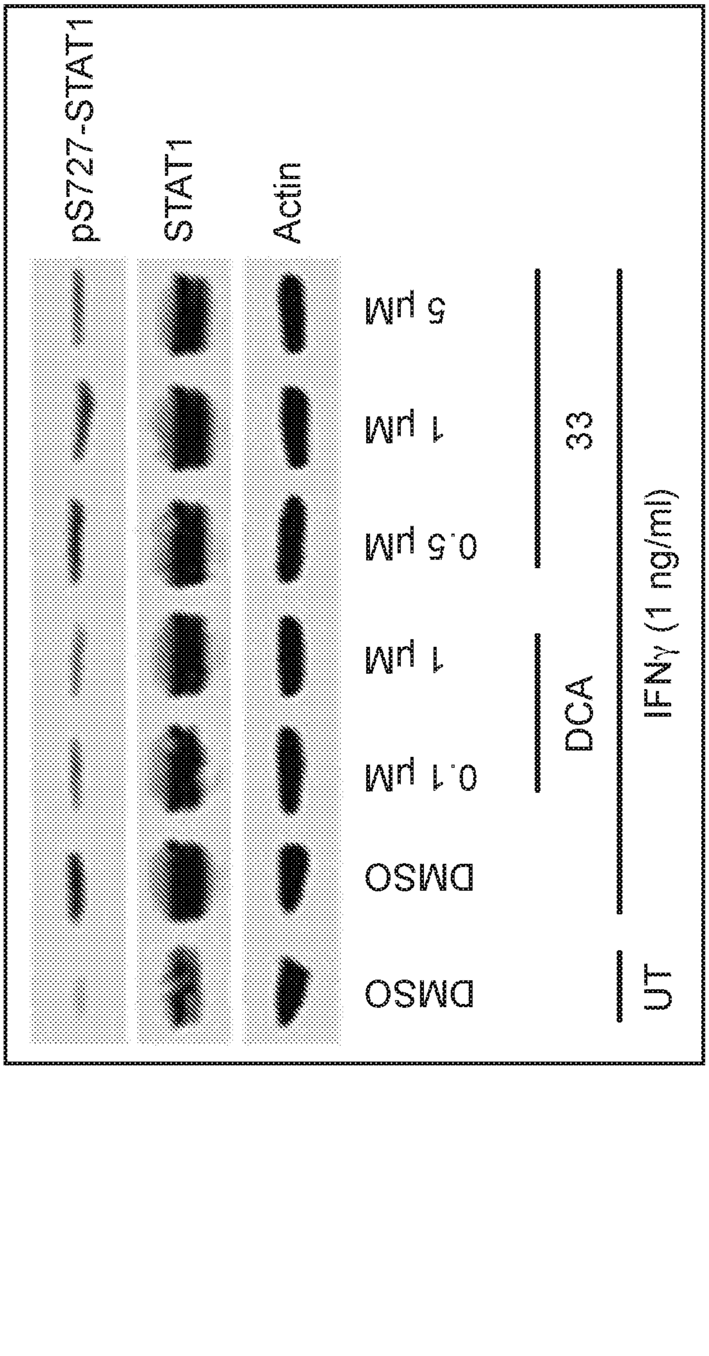
FIG. 1 is a Western blot illustrating inhibition of phosphorylation of 5727-STAT1, a known CDK8 substrate, to form pS727-STAT1. pS727-STAT1 and total STAT1 were from $HepG_2$ cells independently treated for 18 h with interferon gamma (IFNγ) and 0.5 μM, 1 μM, or 5 μM Compound 33, or with IFNγ and 0.1 μM or 1 μM dehydrocortistatin A ("DCA"). DCA has an CDK8 $IC_{50}$ value of 17 nM. Compound 33 and DCA induced dose-dependent inhibition of S727 phosphorylation in HepG2 cells.

The present application relates to compounds of Formula (I) that are shown to potently and selectively inhibit CDK8 and/or CDK19. In one embodiment, a compound of the present application is represented by Formula (I):

(I)

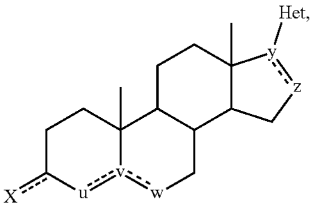

or an enantiomer, diastereomer, stereoisomer, or pharmaceutically acceptable salt thereof, wherein:

X is —OR, =O, or —$NR_1R_2$;

R is H or $C_1$-$C_6$ alkyl;

$R_1$ and $R_2$ are each independently H, $C_1$-$C_6$ alkyl, or —C(O)—$C_1$-$C_6$ alkyl, or $R_1$ and $R_2$, together with the nitrogen atom to which they are attached, form a 3- to 7-membered heterocyclic or a 5-, 8-, or 9-membered heteroaryl ring optionally comprising one or more additional heteroatoms selected from nitrogen, sulfur, and oxygen;

u, v, and w together form (i), (ii), or (iii):

(i)

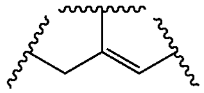

(ii)

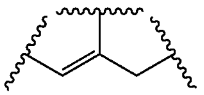

(iii)

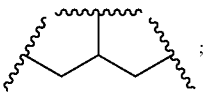

;

y and z together form (iv) or (v):

(iv)

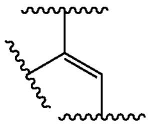

(v)

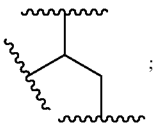

;

and

Het is heteroaryl comprising one or two 5- or 6-membered rings and 1-4 heteroatoms selected from nitrogen, sulfur, and oxygen, and optionally substituted with $NH_2$, wherein the compound is not a compound of Formula (A):

(A)

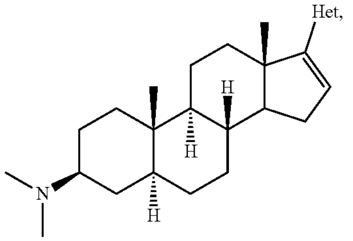

wherein Het is selected from 7-isoquinolinyl, 6-isoquinolinyl, 5-isoquinolinyl, 6-quinolinyl, and 3-pyridyl.

For a compound of Formula (I), in various embodiments where applicable, X, u, v, w, y, z, R, $R_1$, $R_2$, and Het are each as described below.

In one embodiment, X is —OR or ═O.

In one embodiment, X is —OR. In one embodiment, X is (R)—OR. In one embodiment, X is (S)—OR.

In one embodiment, X is ═O.

In one embodiment, X is —$NR_1R_2$. In one embodiment, X is (R)—$NR_1R_2$. In one embodiment, X is (S)—$NR_1R_2$.

In one embodiment, X is —OR, ═O, or (R)—$NR_1R_2$.

R or S configuration may be determined by methods readily known in art, such as by assigning priority groups about a stereogenic carbon.

In one embodiment, R is H.

In one embodiment, R is $C_1$-$C_6$ straight-chain or $C_3$-$C_6$ branched alkyl (e.g., methyl, ethyl, n-propyl, i-propyl, n-butyl, i-butyl, s-butyl, t-butyl, pentyl, or hexyl). In one embodiment, R is $C_1$-$C_4$ straight-chain or $C_3$-$C_4$ branched alkyl (e.g., methyl, ethyl, n-propyl, i-propyl, n-butyl, i-butyl, s-butyl, or t-butyl).

In one embodiment, R is $C_1$-$C_6$ alkyl optionally substituted with OH, O—($C_1$-$C_6$ alkyl), $NH_2$, NH($C_1$-$C_6$ alkyl), or N($C_1$-$C_6$ alkyl)$_2$.

In one embodiment, $R_1$ and $R_2$ are each H.

In one embodiment, one of $R_1$ and $R_2$ is H, and the other is $C_1$-$C_6$ straight-chain or $C_3$-$C_6$ branched alkyl (e.g., methyl, ethyl, n-propyl, i-propyl, n-butyl, i-butyl, s-butyl, t-butyl, pentyl, or hexyl). In one embodiment, one of $R_1$ and $R_2$ is H, and the other is $C_1$-$C_4$ straight-chain or $C_3$-$C_4$ branched alkyl (e.g., methyl, ethyl, n-propyl, i-propyl, n-butyl, i-butyl, s-butyl, or t-butyl).

In one embodiment, $R_1$ and $R_2$ are each $C_1$-$C_6$ straight-chain or $C_3$-$C_6$ branched alkyl (e.g., methyl, ethyl, n-propyl, i-propyl, n-butyl, i-butyl, s-butyl, t-butyl, pentyl, or hexyl). In one embodiment, $R_1$ and $R_2$ are each $C_1$-$C_4$ straight-chain or $C_3$-$C_4$ branched alkyl (e.g., methyl, ethyl, n-propyl, i-propyl, n-butyl, i-butyl, s-butyl, or t-butyl).

In one embodiment, $R_1$ and $R_2$ are each independently H or $C_1$-$C_6$ alkyl optionally substituted with OH, O—($C_1$-$C_6$ alkyl), $NH_2$, NH($C_1$-$C_6$ alkyl), or N($C_1$-$C_6$ alkyl)$_2$.

In one embodiment, one of $R_1$ and $R_2$ is —C(O)—$C_1$-$C_6$ alkyl, and the other is $C_1$-$C_6$ alkyl (each alkyl independently, for example, methyl, ethyl, n-propyl, i-propyl, n-butyl, i-butyl, s-butyl, t-butyl, pentyl, or hexyl).

In one embodiment, one of $R_1$ and $R_2$ is H, and the other is —C(O)—$C_1$-$C_6$ alkyl (e.g., methyl, ethyl, n-propyl, i-propyl, n-butyl, i-butyl, s-butyl, t-butyl, pentyl, or hexyl).

In one embodiment, $R_1$ and $R_2$, together with the nitrogen atom to which they are attached, form a 3- to 7-membered heterocyclic or a 5-, -8, or 9-membered heteroaryl ring optionally comprising one or more additional heteroatoms selected from nitrogen, sulfur, and oxygen. In one embodiment, $R_1$ and $R_2$, together with the nitrogen atom to which they are attached, form a 3- to 7-membered heterocyclic ring. In one embodiment, the heterocyclic ring is selected from aziridine, azetidine, pyrrolidine, dihydropyrrole, piperidine, piperazine, dihydropyridine, tetrahydropyridine, azepane, oxaziridine, oxazetidine, isoxazoline, isoxazolidine, oxazoline, oxazolidine, thiazoline, thiazolidine, isothiazoline, isothiazolidine, pyrazoline, pyrazolidine, imidazoline, imidazolidine, morpholine, oxazinane, thiomorpholine, thiazinane, or the like. In one embodiment, the heterocyclic ring is morpholine. In one embodiment, $R_1$ and $R_2$, together with the nitrogen atom to which they are attached, form a 5-, -8, or 9-membered heteroaryl ring (e.g., pyrrole, pyrazole, imidazole, triazole, tetrazole, indole, benzimidazole, indazole, azaindole, and the like). In one embodiment, the heteroaryl ring is selected from pyrrole, imidazole, 1,2,3-triazole, 1,2,4-triazole, and tetrazole. In one embodiment, the heteroaryl ring is triazole. In one embodiment, the heteroaryl ring 1,2,3-triazole.

In one embodiment, u, v, and w together form (i)

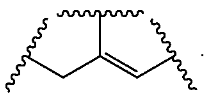

.

In one embodiment, u, v, and w together form (ii)

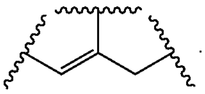

.

In one embodiment, u, v, and w together form (iii)

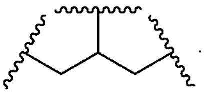

.

In one embodiment, y and z together form

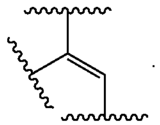

(iv)

In one embodiment, y and z together form

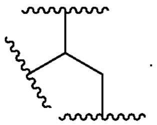

(v)

In one embodiment, Het is heteroaryl selected from isoquinolinyl, quinolinyl, indazolyl, cinnolinyl, phthalazinyl, pyridinyl, pyridazinyl, indolyl, acridinyl, pyrazinyl, benzoquinolinyl, pyrazolyl, pyrrolyl, pyrimidinyl, purinyl, pyrrolopyrimidinyl, quinoxalinyl, and quinazolinyl. In one embodiment, Het is selected from 6-isoquinolinyl, 7-isoquinolinyl, 6-quinazolinyl, 6-phthalazinyl, 6-indazolyl, 6-indazolyl-3-amine, and 5-indazolyl. In one embodiment, Het is 7-isoquinolinyl.

In one embodiment, Het is in the R configuration. In one embodiment, Het is in the S configuration.

Any of the groups described herein for any of X, R, $R_1$, $R_2$, u, v, w, y, z, and Het can be combined with any of the groups described herein for one or more of the remainder of X, R, $R_1$, $R_2$, u, v, w, y, z, and Het.

(1) In one embodiment, u, v, and w together form

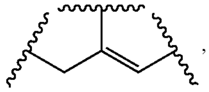

(i)

and y and z together form (iv)

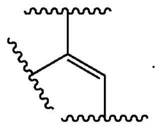

(iv)

(2) In one embodiment, u, v, and w together form

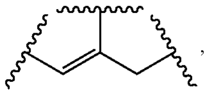

(ii)

and y and z together form

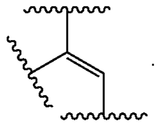

(iv)

(3) In one embodiment, u, v, and w together form

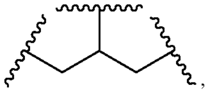

(iii)

and y and z together form

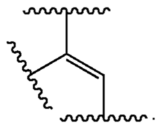

(iv)

(4) In one embodiment, u, v, and w together form

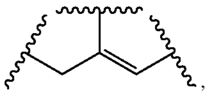

(i)

and y and z together form

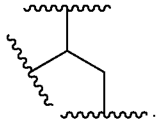

(v)

(5) In one embodiment, u, v, and w together form

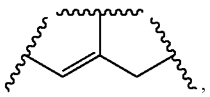

(ii)

and y and z together form

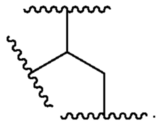

(v)

(6) In one embodiment, u, v, and w together form (iii)

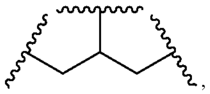

and y and z together form (v)

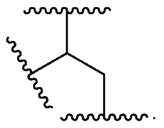

(7) In one embodiment, u, v, w, y, and z are each as defined and combined in any one of (1)-(6), and X is —OR. In a further embodiment, X is (S)—OR.

(8a) In one embodiment, u, v, w, y, z, and X are each as defined and combined, where applicable, in any one of (1)-(7), and R is H.

(8b) In one embodiment, u, v, w, y, z, and X are each as defined and combined, where applicable, in any one of (1)-(7), and R is $C_1$-$C_6$ alkyl as described herein.

(9) In one embodiment, u, v, w, y, and z are each as defined and combined in any one of (1)-(6), and X is ═O.

(10a) In one embodiment, u, v, w, y, and z are each as defined and combined in any one of (1)-(6), and X is (R)—$NR_1R_2$.

(10b) In one embodiment, u, v, w, y, and z are each as defined and combined in any one of (1), (2), and (4)-(6), and X is —$NR_1R_2$.

(10c) In one embodiment, u, v, w, y, and z are each as defined and combined in (1) or (4), and X is —$NR_1R_2$.

(11a) In one embodiment, u, v, w, y, z, and X are each as defined and combined, where applicable, in any one of (1)-(6) and (10a)-(10c), and $R_1$ and $R_2$ are each H.

(11 b) In one embodiment, u, v, w, y, z, and X are each as defined and combined, where applicable, in any one of (1)-(6) and (10a)-(10c), and one of $R_1$ and $R_2$ is H, and the other is $C_1$-$C_6$ alkyl as described herein.

(11c) In one embodiment, u, v, w, y, z, and X are each as defined and combined, where applicable, in any one of (1)-(6) and (10a)-(10c), and $R_1$ and $R_2$ are each independently $C_1$-$C_6$ alkyl as described herein.

(11d) In one embodiment, u, v, w, y, z, and X are each as defined and combined, where applicable, in any one of (1)-(6) and (10a)-(10c), and $R_1$ and $R_2$, together with the nitrogen atom to which they are attached, form a 3- to 7-membered heterocyclic or 5-, 8-, or 9-membered heteroaryl ring as described herein. In one embodiment, $R_1$ and $R_2$, together with the nitrogen atom to which they are attached, form a 3- to 7-membered heterocyclic ring as described herein. In one embodiment, $R_1$ and $R_2$, together with the nitrogen atom to which they are attached, form a 5-, 8-, or 9-membered heteroaryl ring as described herein.

(12) In one embodiment, u, v, w, y, z, and X are each as defined and combined, where applicable, in any one of (1)-(6) and (10a)-(10c), and one of $R_1$ and $R_2$ is H, and the other is —C(O)—$C_1$-$C_6$ alkyl as described herein.

(13) In one embodiment, u, v, w, y, z, and X are each as defined and combined, where applicable, in any one of (1)-(6) and (10a)-(10c), and one of $R_1$ and $R_2$ is $C_1$-$C_6$ alkyl, and the other is —C(O)—$C_1$-$C_6$ alkyl as described herein.

(14) In one embodiment, u, v, w, y, z, X, R, $R_1$, and $R_2$ are each as defined and combined, where applicable, in any one of (1)-(13), and Het, where applicable, is in the (S) configuration.

(15) In one embodiment, u, v, w, y, z, X, R, $R_1$, and $R_2$ are each as defined and combined, where applicable, in any one of (1)-(13), and Het is heteroaryl comprising two 5- or 6-membered rings and 1-4 heteroatoms selected from nitrogen, sulfur, and oxygen. In a further embodiment, Het is heteroaryl comprising two 5- or 6-membered rings and 1-4 nitrogen atoms. In a further embodiment, Het, where applicable, is in the (S) configuration. In one embodiment, Het is selected from the heteroaryl groups described herein.

In one embodiment, a compound of Formula (I) is of Formula (i'), (ii'), (iii'), (iv(a)), (iv(b)), (iv(c)), (v(a)), (v(b)), or (v(c)):

(i')

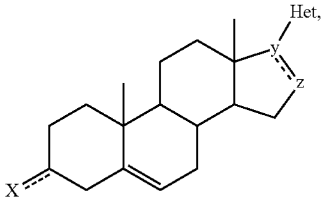

(ii')

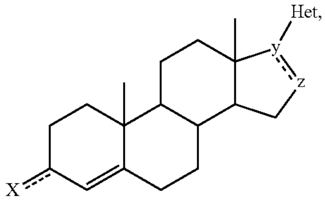

(iii')

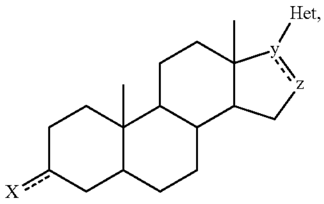

(iv(a))

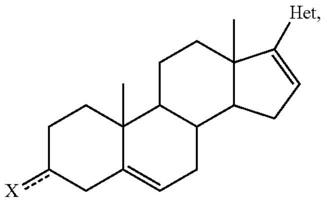

(iv(b))

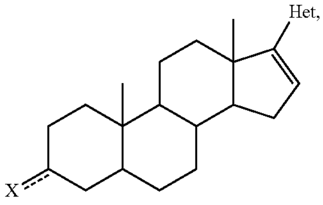

-continued (iv(c))

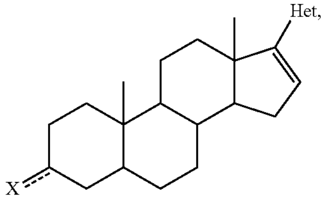

(v(a))

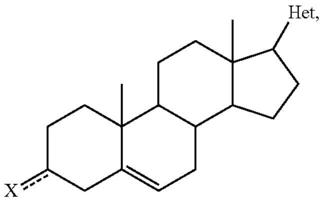

(v(b))

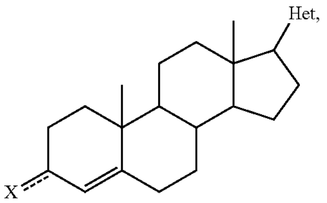

or (v(c))

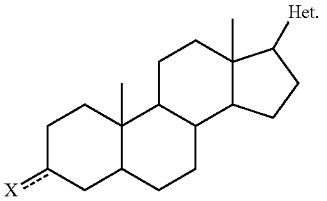

For a compound of Formula (i'), (ii'), (iii'), (iv(a)), (iv(b)), (iv(c)), (v(a)), (v(b)), or (v(c)), where applicable:

In one embodiment, X is —$NR_1R_2$. For example, X is —$N(CH_3)_2$ or —$NH(CH_3)$.

In one embodiment, X is —$NR_1R_2$, and $R_1$ and $R_2$, together with the nitrogen atom to which they are attached, form 1,2,3-triazole. In one embodiment, X is —$NR_1R_2$, and $R_1$ and $R_2$, together with the nitrogen atom to which they are attached, form morpholine. In one embodiment, X is —$NR_1R_2$, and $R_1$ and $R_2$, together with the nitrogen atom to which they are attached, form pyrrolidine.

In one embodiment, X is —$NR_1R_2$. For example, X is —$N(CH_3)C(O)CH_3$. For example, X is —$NHC(O)CH_3$.

In one embodiment, X is —OR. For example, X is —OH.

In one embodiment, the carbon to which X is attached is designated with R stereochemistry (i.e., X is (R)—$NR_1R_2$ or (R)—OR).

In one embodiment, the carbon to which X is attached is designated with S stereochemistry (i.e., X is (S)—$NR_1R_2$ or (S)—OR).

In one embodiment, X is =O.

In one embodiment, y and z together form (iv)

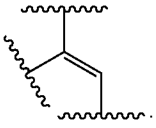

In one embodiment, y and z together form (v)

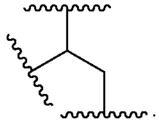

In one embodiment, a compound of Formula (I) is of Formula (iv(a)'), (v(a)'), (iv(a)''), (v(a)''), (iv(b)'), (v(b)'), (iv(b)''), (v(b)''), (iv(c)''), or (v(c)''):

(iv(a)')

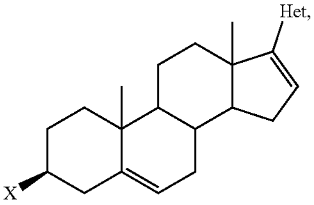

(v(a)')

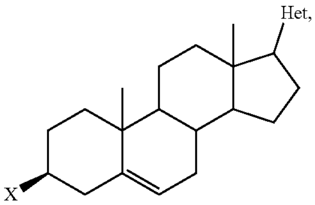

(iv(a)'')

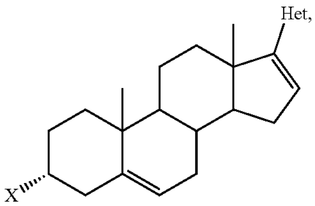

(v(a)'')

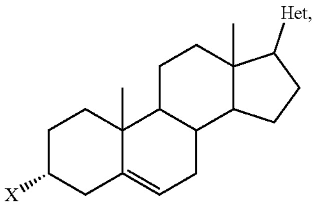

(iv(b)')

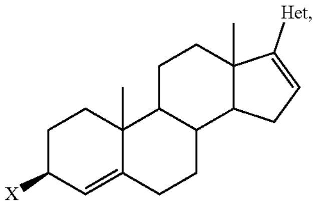

(v(b)')

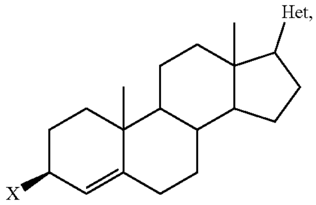

-continued (iv(b)″)

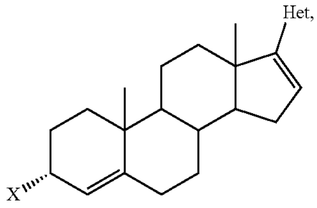

(v(b)″)

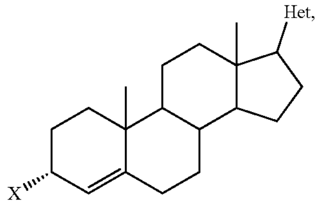

(iv(c)″)

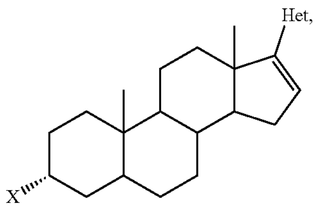

or (v(c)″)

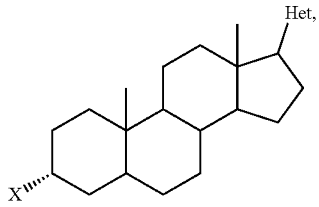

wherein:

X is —OR or —$NR_1R_2$;

R is H or $C_1$-$C_6$ alkyl; and $R_1$ and $R_2$ are each independently H, $C_1$-$C_6$ alkyl, or —C(O)—$C_1$-$C_6$ alkyl, or $R_1$ and $R_2$, together with the nitrogen atom to which they are attached, form a 3- to 7-membered heterocyclic or a 5-, 8-, or 9-membered heteroaryl ring optionally comprising one or more additional heteroatoms selected from nitrogen, sulfur, and oxygen.

In one embodiment, X is —OH.

In one embodiment, X is —$NR_1R_2$, and $R_1$ and $R_2$ are each methyl.

In one embodiment, X is —$NR_1R_2$, and $R_1$ is H and $R_2$ is methyl.

In one embodiment, X is —$NR_1R_2$, and $R_1$ is acetyl, i.e., —$C(O)CH_3$, and $R_2$ is methyl.

In one embodiment, X is —$NR_1R_2$, and $R_1$ and $R_2$, together with the nitrogen atom to which they are attached, form 1,2,3-triazole. In one embodiment, X is —$NR_1R_2$, and $R_1$ and $R_2$, together with the nitrogen atom to which they are attached, form morpholine. In one embodiment, X is —$NR_1R_2$, and $R_1$ and $R_2$, together with the nitrogen atom to which they are attached, form pyrrolidine.

In one embodiment, a compound of Formula (I) is of Formula (iv(c)′) or (v(c)′):

(iv(c)′)

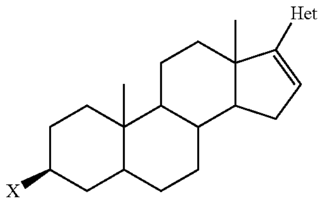

or (v(c)′)

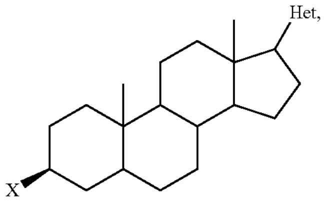

wherein:

X is —OR or —$NR_1R_2$;

R is H or $C_1$-$C_6$ alkyl; and $R_1$ and $R_2$ are each independently H, $C_1$-$C_6$ alkyl or —C(O)—$C_1$-$C_6$ alkyl, or $R_1$ and $R_2$, together with the nitrogen atom to which they are attached, form a 3- to 7-membered heterocyclic or a 5-, 8-, or 9-membered heteroaryl ring optionally comprising one or more additional heteroatoms selected from nitrogen, sulfur, and oxygen.

In one embodiment, X is —OH.

In one embodiment, X is —$NR_1R_2$, and $R_1$ and $R_2$ are each methyl, provided that in Formula (iv(c)′), Het is not 7-isoquinolinyl, 6-isoquinolinyl, 5-isoquinolinyl, 6-quinolinyl, and 3-pyridyl.

In one embodiment, X is —$NR_1R_2$, and $R_1$ is H and $R_2$ is methyl.

In one embodiment, X is —$NR_1R_2$, and $R_1$ is acetyl and $R_2$ is methyl.

In one embodiment, X is —$NR_1R_2$, and $R_1$ and $R_2$, together with the nitrogen atom to which they are attached, form 1,2,3-triazole. In one embodiment, X is —$NR_1R_2$, and $R_1$ and $R_2$, together with the nitrogen atom to which they are attached, form morpholine. In one embodiment, X is —$NR_1R_2$, and $R_1$ and $R_2$, together with the nitrogen atom to which they are attached, form pyrrolidine.

In one embodiment, a compound of Formula (I) is of one of the following formulae:

IIa

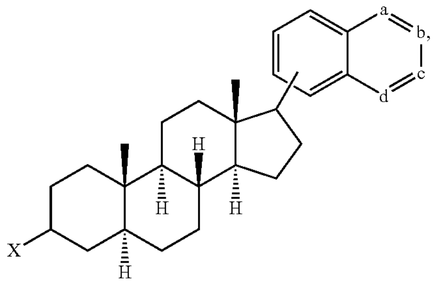

-continued

IIb

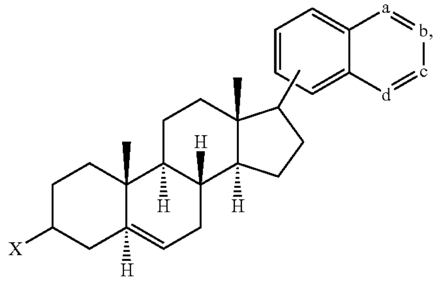

IIc

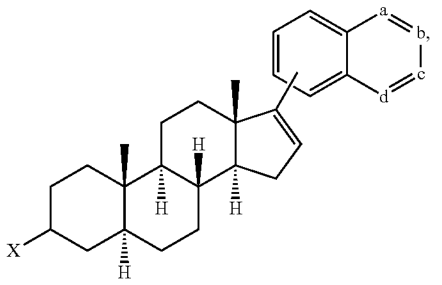

or

IId

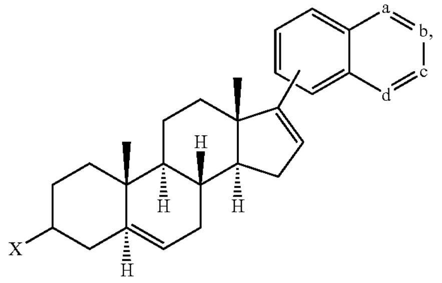

wherein:

X is —OH or —$NR_1R_2$;

$R_1$ and $R_2$ are each independently H, $C_1$-$C_6$ alkyl, —C(O)—$C_1$-$C_6$ alkyl, or $R_1$ and $R_2$, together with the nitrogen atom to which they are attached, form a 3- to 7-membered heterocyclic, or a 5-, 8-, or 9-membered heteroaryl ring optionally comprising one or more additional heteroatoms selected from nitrogen, sulfur, and oxygen;

a, b, c, and d are each independently $CR_3$ or N; and each $R_3$ is independently H or $NH_2$.

In one embodiment, X is —OH.

In one embodiment, X is —$NR_1R_2$.

In one embodiment, X is —$NR_1R_2$, and $R_1$ and $R_2$ are each methyl.

In one embodiment, X is —$NR_1R_2$, and $R_1$ is H and $R_2$ is methyl.

In one embodiment, X is —$NR_1R_2$, and $R_1$ is acetyl and $R_2$ is methyl.

In one embodiment, X is —$NR_1R_2$, and $R_1$ and $R_2$, together with the nitrogen atom to which they are attached, form pyrrolidine. In one embodiment, $R_1$ and $R_2$, together with the nitrogen atom to which they are attached, form triazole. In one embodiment, $R_1$ and $R_2$, together with the nitrogen atom to which they are attached, form morpholine.

In one embodiment, b and d are each independently $CR_3$; a and c are each N; and one $R_3$ is H, and one $R_3$ is $NH_2$.

In one embodiment, a, b, and d are each independently $CR_3$; c is N; and each $R_3$ is H.

In one embodiment, a compound of Formula (I) is of one of the following formulae:

IIIa

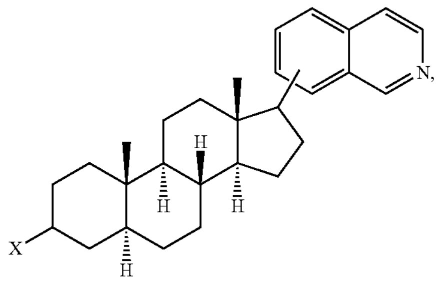

IIIb

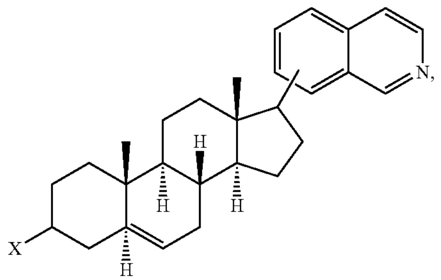

IIIc

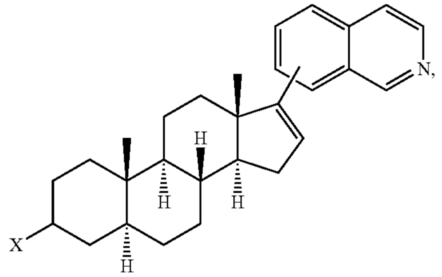

or

IIId

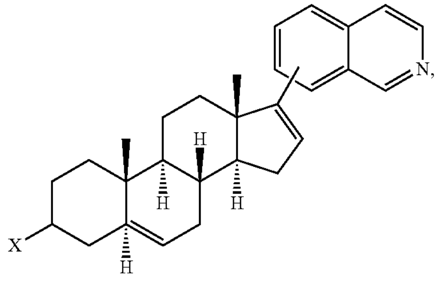

wherein:

X is —OH or —$NR_1R_2$; and $R_1$ and $R_2$ are each independently H, $C_1$-$C_6$ alkyl, —C(O)—$C_1$-$C_6$ alkyl, or $R_1$ and $R_2$, together with the nitrogen atom to which they are attached, form a 3- to 7-membered heterocyclic or a 5-, 8-, or 9-membered heteroaryl ring optionally comprising one or more additional heteroatoms selected from nitrogen, sulfur, and oxygen.

In one embodiment, X is —OH.

In one embodiment, X is —$NR_1R_2$.

In one embodiment, X is —$NR_1R_2$, and $R_1$ and $R_2$ are each methyl.

In one embodiment, X is —$NR_1R_2$, and $R_1$ is H and $R_2$ is methyl.

In one embodiment, X is —$NR_1R_2$, and $R_1$ is acetyl and $R_2$ is methyl.

In one embodiment, X is —$NR_1R_2$, and $R_1$ and $R_2$, together with the nitrogen atom to which they are attached, form pyrrolidine. In one embodiment, $R_1$ and $R_2$, together with the nitrogen atom to which they are attached, form triazole. In one embodiment, $R_1$ and $R_2$, together with the nitrogen atom to which they are attached, form morpholine.

In one embodiment, a compound of Formula (I) is of one of the following formulae:

IVa

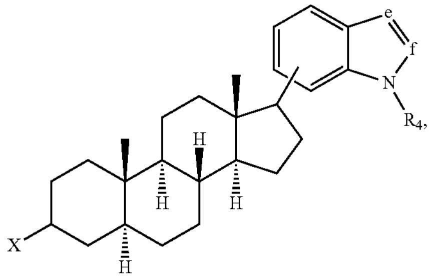

IVb

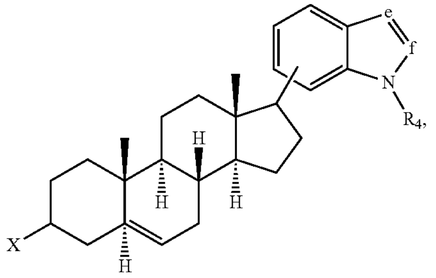

IVc

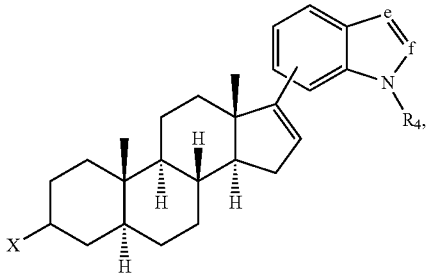

or

IVd

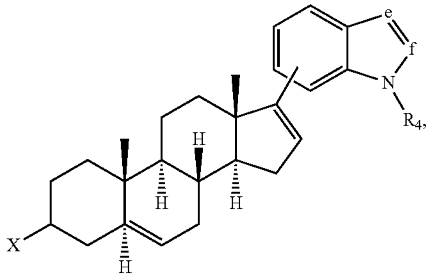

wherein:

X is —OH or —$NR_1R_2$;

$R_1$ and $R_2$ are each independently H, $C_1$-$C_6$ alkyl, —C(O)—$C_1$-$C_6$ alkyl, or $R_1$ and $R_2$, together with the nitrogen atom to which they are attached, form a 3- to 7-membered heterocyclic or a 5-, 8-, or 9-membered heteroaryl ring optionally comprising one or more additional heteroatoms selected from nitrogen, sulfur, and oxygen;

$R_4$ is H or $C_1$-$C_6$ alkyl;

e and f are each independently $CR_5$ or N; and each $R_5$ is independently be H or $NH_2$.

In one embodiment, X is —OH.

In one embodiment, X is —$NR_1R_2$.

In one embodiment, X is —$NR_1R_2$, and $R_1$ and $R_2$ are each methyl.

In one embodiment, X is —$NR_1R_2$, and $R_1$ is H and $R_2$ is methyl.

In one embodiment, X is —$NR_1R_2$, and $R_1$ is acetyl and $R_2$ is methyl.

In one embodiment, X is —$NR_1R_2$, and $R_1$ and $R_2$, together with the nitrogen atom to which they are attached, form pyrrolidine. In one embodiment, $R_1$ and $R_2$, together with the nitrogen atom to which they are attached, form triazole or morpholine.

In one embodiment, e is N; f is $CR_5$; and $R_5$ is H.

In one embodiment, e is N; f is $CR_5$; and $R_5$ is $NH_2$.

In one embodiment, e is $CR_5$; f is N; $R_5$ is $NH_2$; and $R_4$ may be H.

In one embodiment, e is $CR_5$; f is N; $R_5$ is H; and $R_4$ may be H.

In several embodiments, the compound may be represented by one of compounds in Table 1:

TABLE 1

| Cmpd No. | Structure |
|---|---|
| 1 | 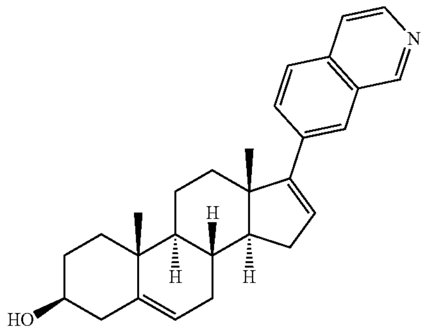 |
| 2 | 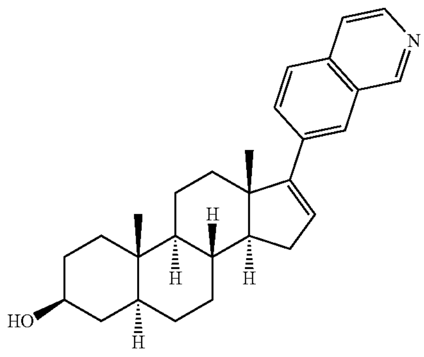 |

TABLE 1-continued
| Cmpd No. | Structure |
| --- | --- |
| 3 | 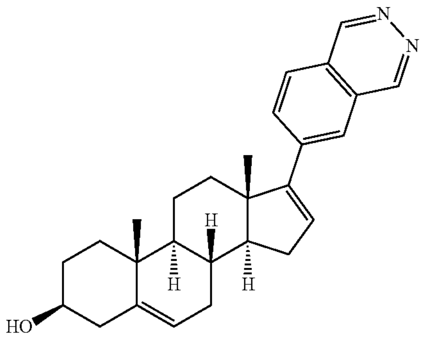 |
| 4 | 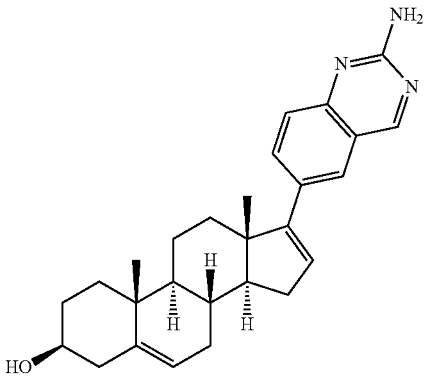 |
| 5 | 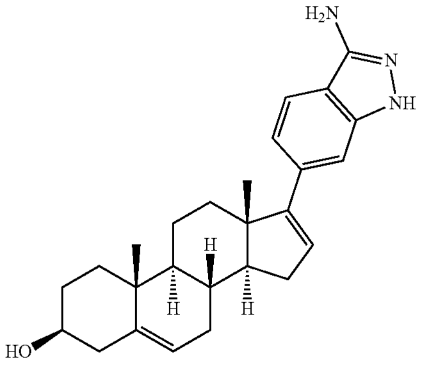 |
| 6 | 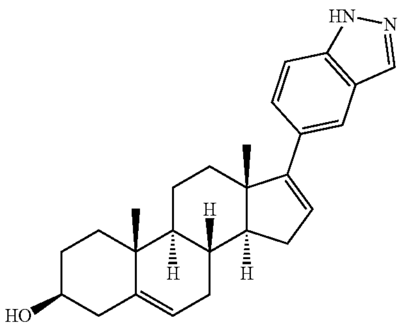 |
TABLE 1-continued
| Cmpd No. | Structure |
| --- | --- |
| 7 | 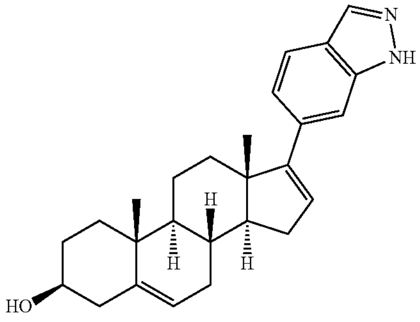 |
| 8a | 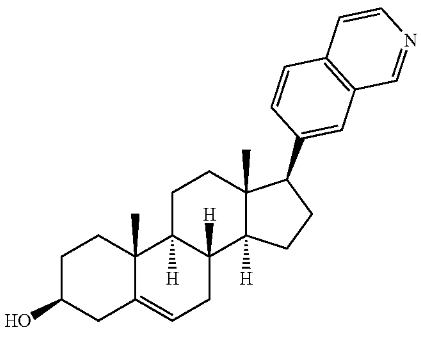 |
| 8b | 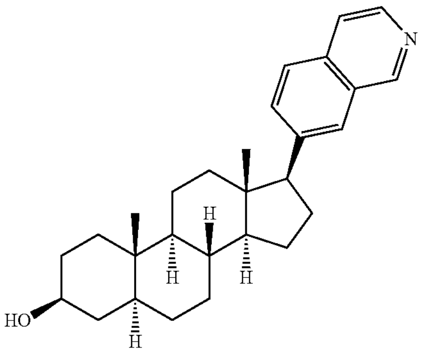 |
| 9 | 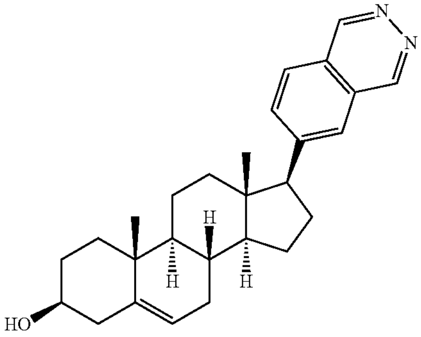 |

TABLE 1-continued
| Cmpd No. | Structure |
|---|---|
| 10 | 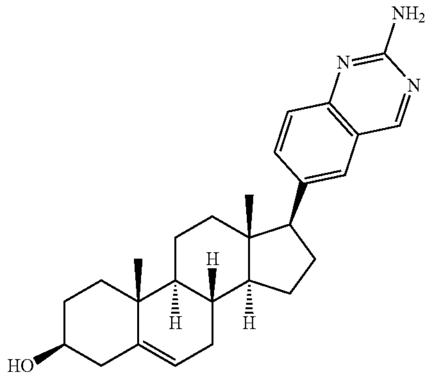 |
| 11 | 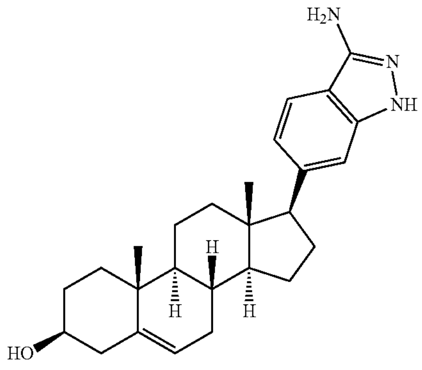 |
| 12 | 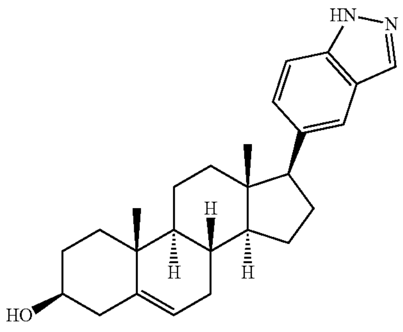 |
| 13 | 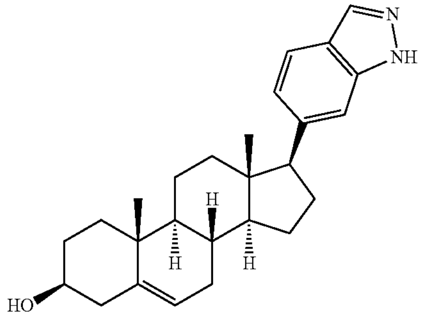 |
TABLE 1-continued
| Cmpd No. | Structure |
|---|---|
| 14 | 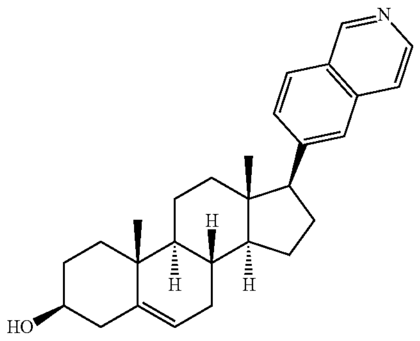 |
| 22r | 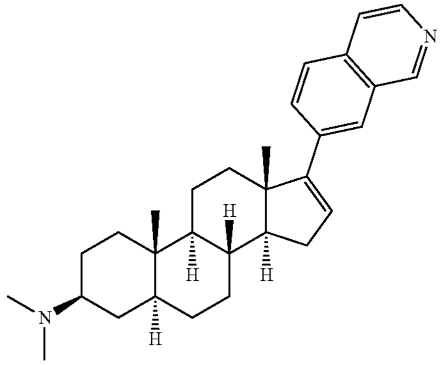 |
| 23 | 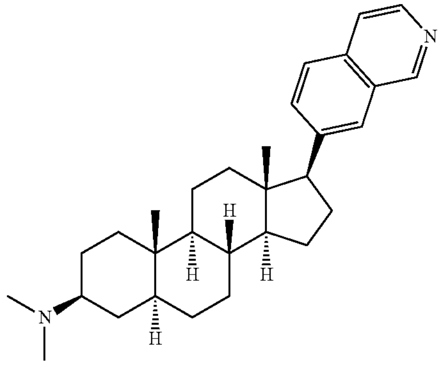 |
| 24 | 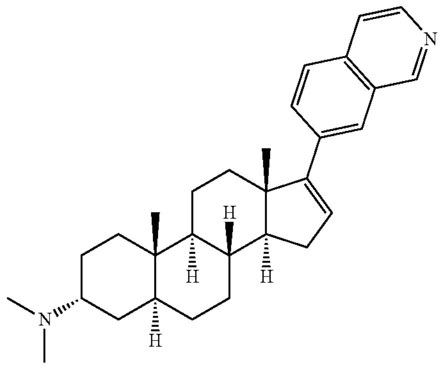 |

TABLE 1-continued
| Cmpd No. | Structure |
|---|---|
| 25 | 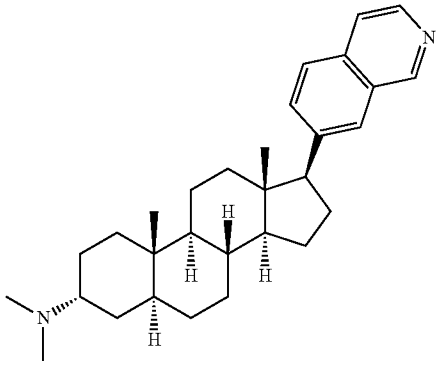 |
| 32 | 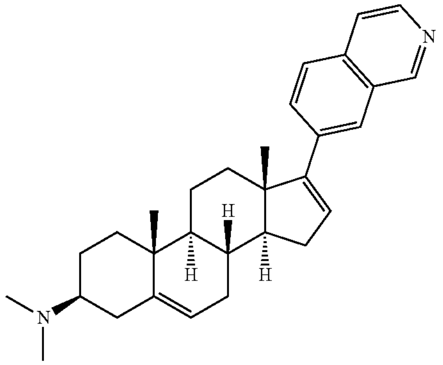 |
| 33 | 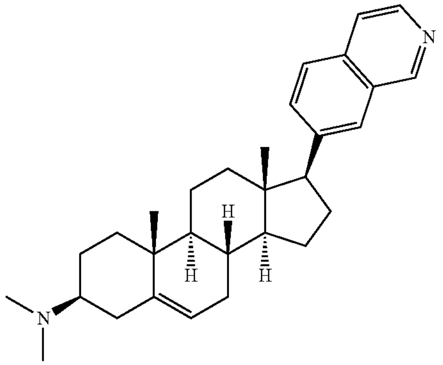 |
| 34 | 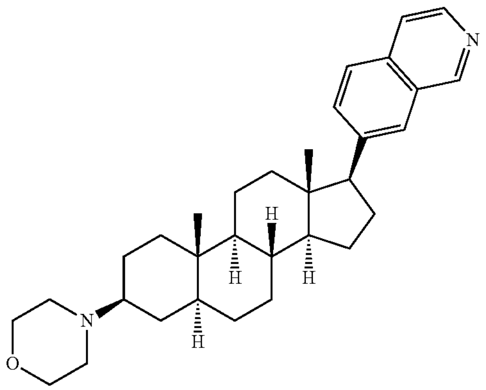 |
TABLE 1-continued
| Cmpd No. | Structure |
|---|---|
| 38 | 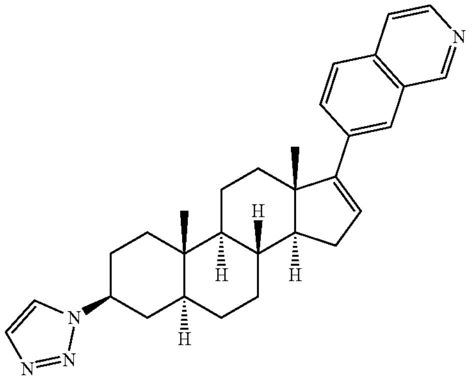 |
| 39 | 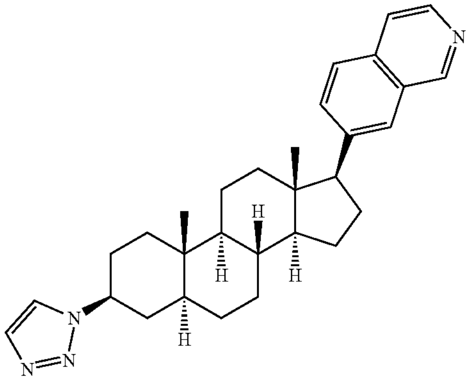 |
| 45 | 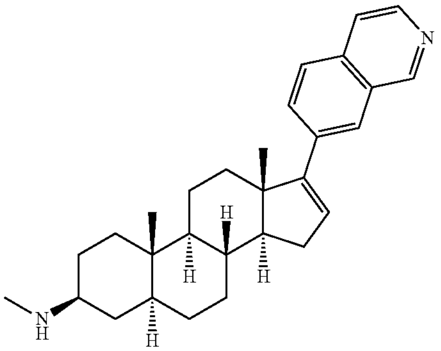 |
| 46 | 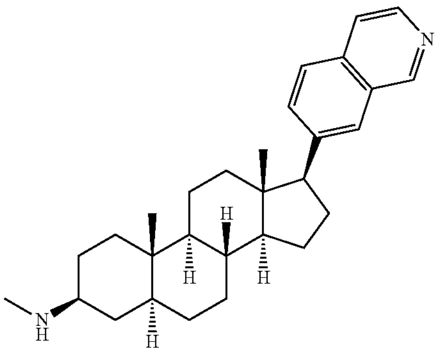 |

TABLE 1-continued
| Cmpd No. | Structure |
|---|---|
| 47 | 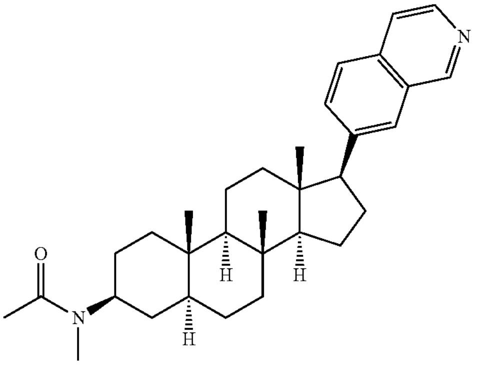 |
| 48 | 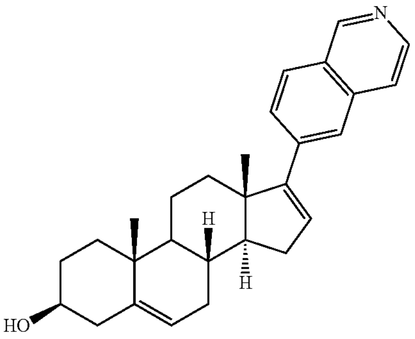 |
In several embodiments, the compound may be represented by one of:
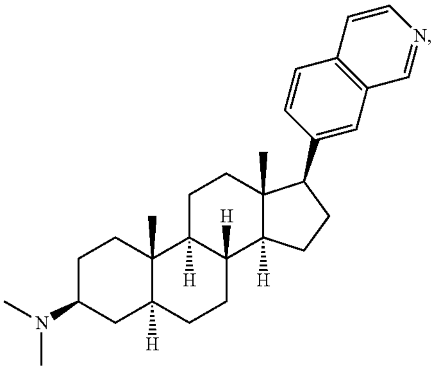
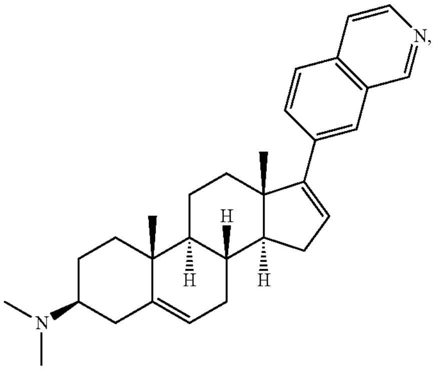
or
-continued
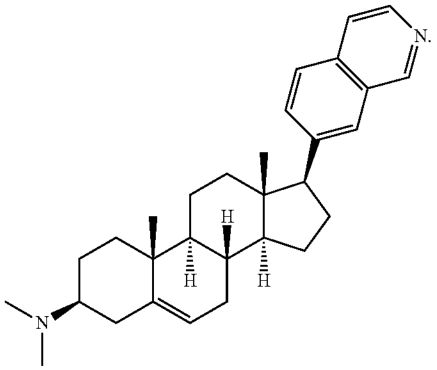
In several embodiments, the compound may be represented by one of:
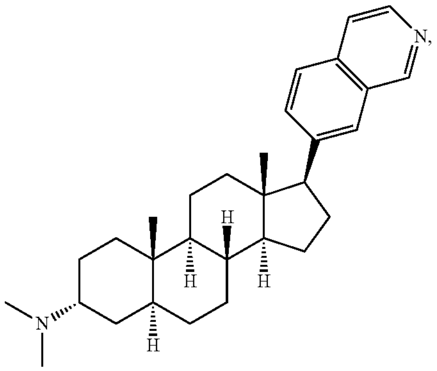
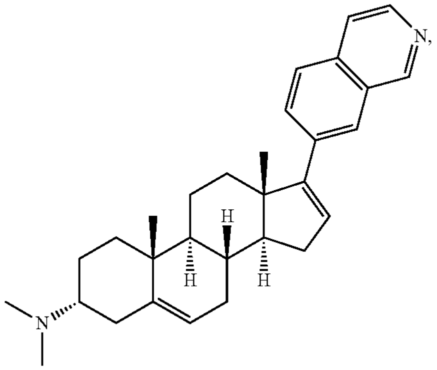
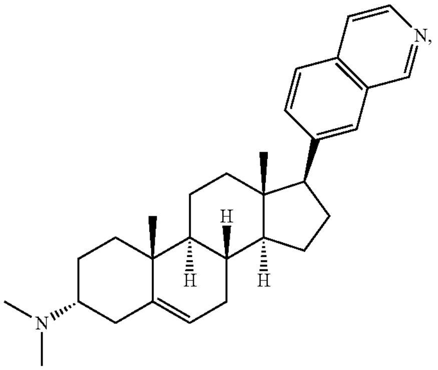
or -continued
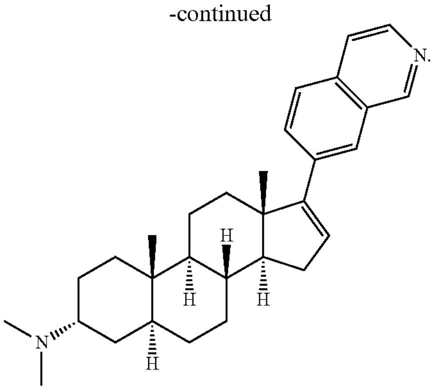
In several embodiments, the compound may be represented by one of:
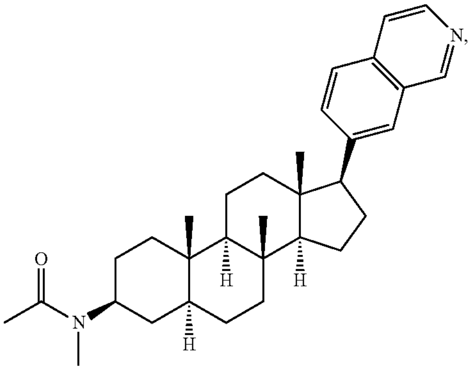
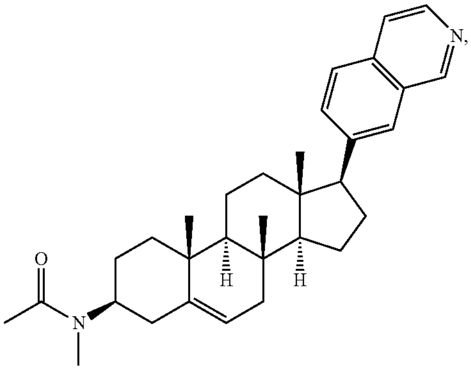
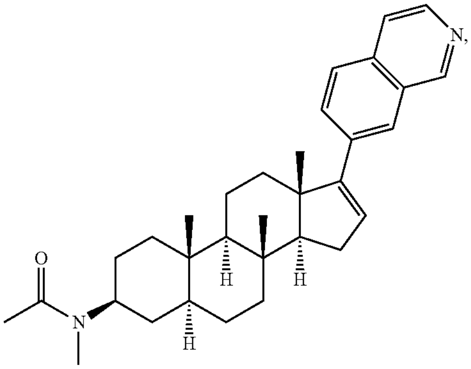
-continued
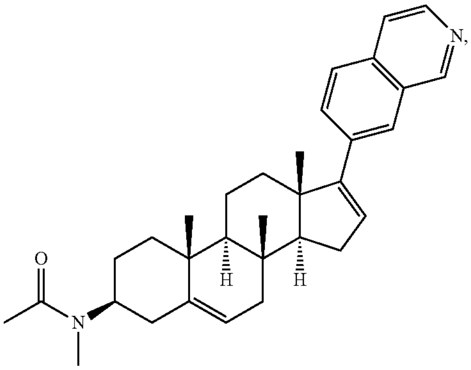
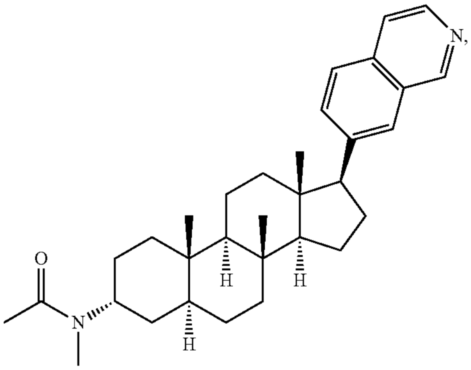
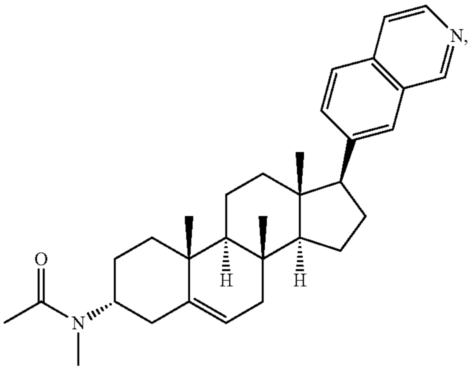
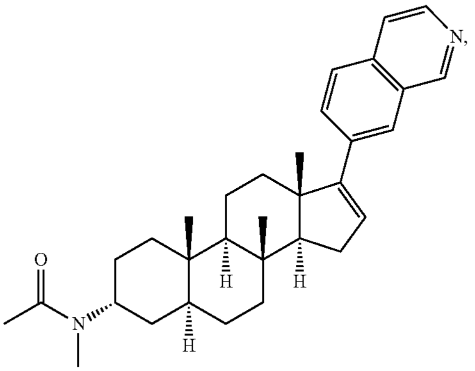
or -continued
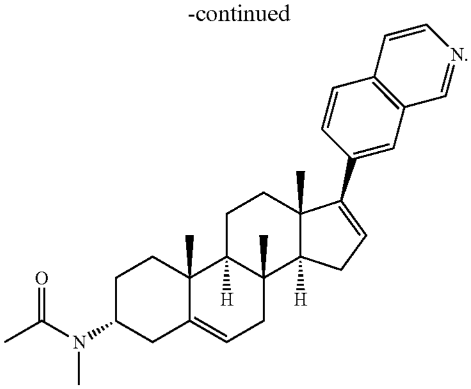
In several embodiments, the compound may be represented by one of:
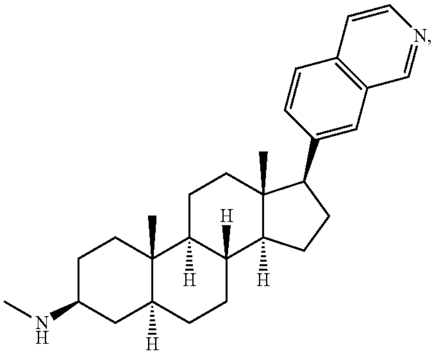
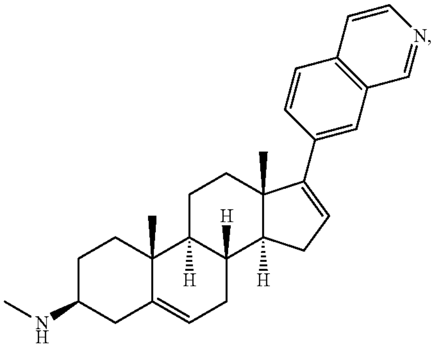
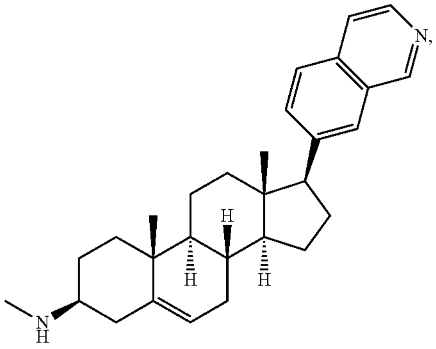
or
-continued
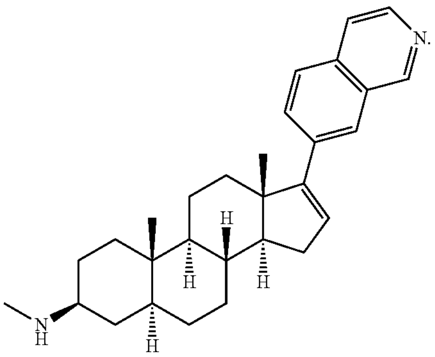
In several embodiments, the compound may be represented by one of:
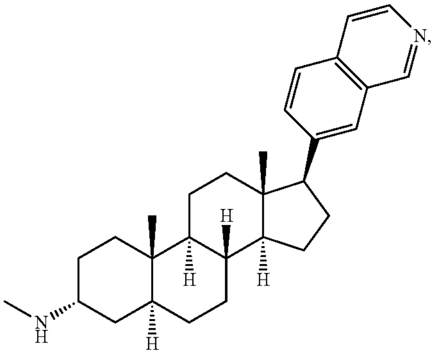
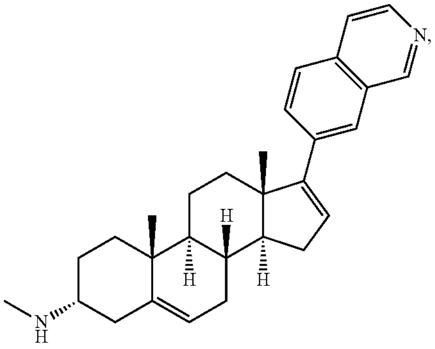
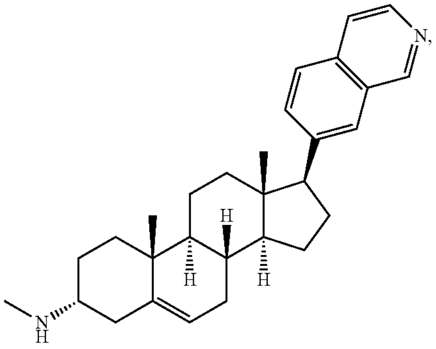
or -continued
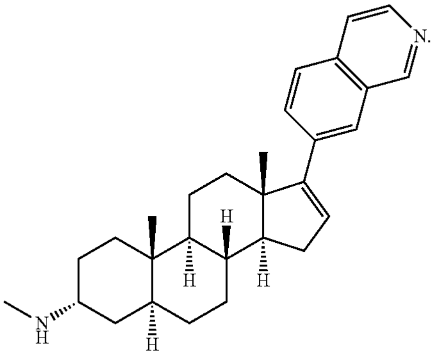
In several embodiments, the compound may be represented by one of:
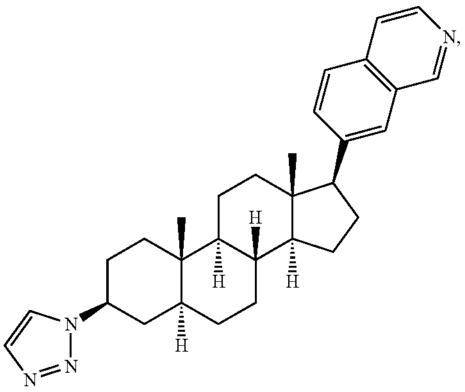
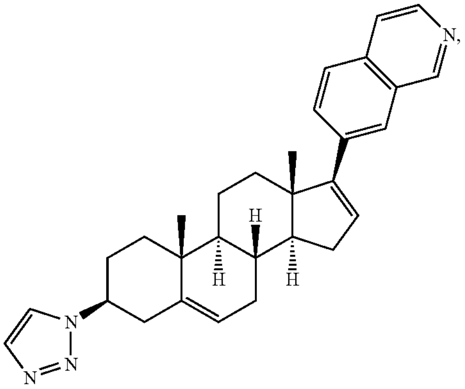
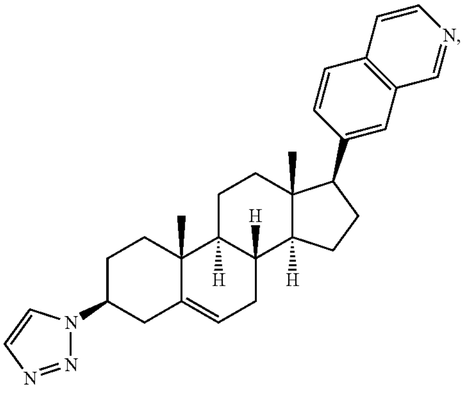
-continued
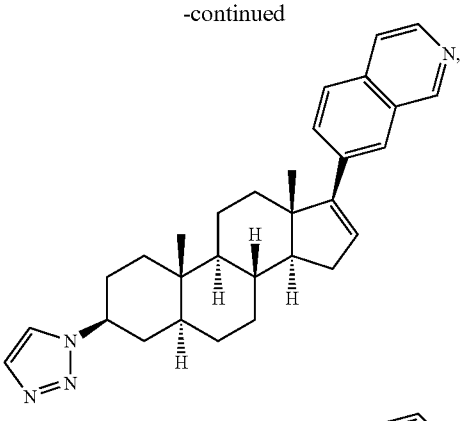
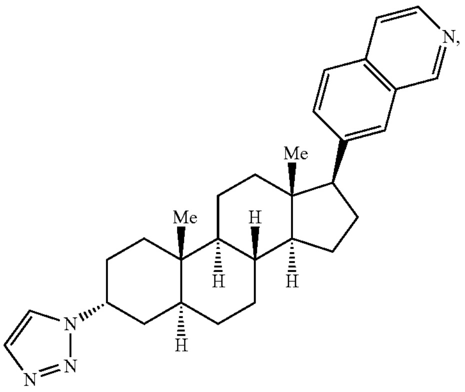
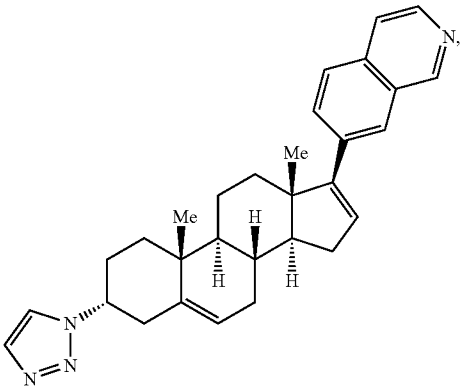
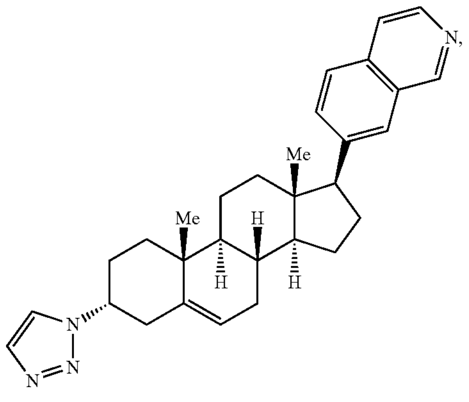
or -continued
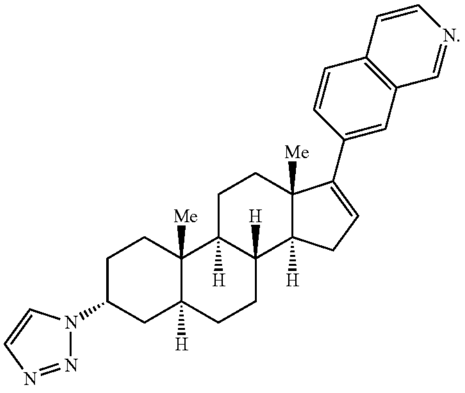
In several embodiments, the compound may be represented by one of:
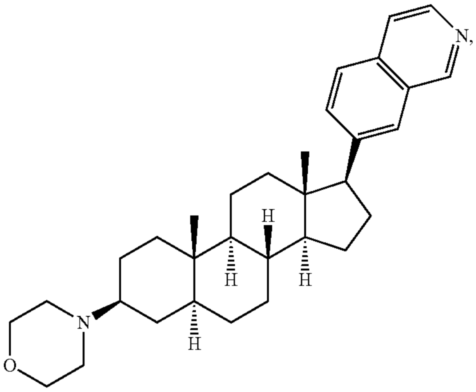
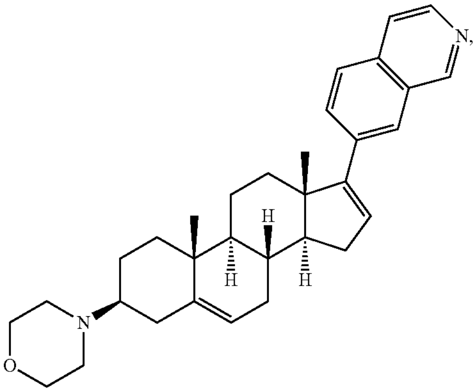
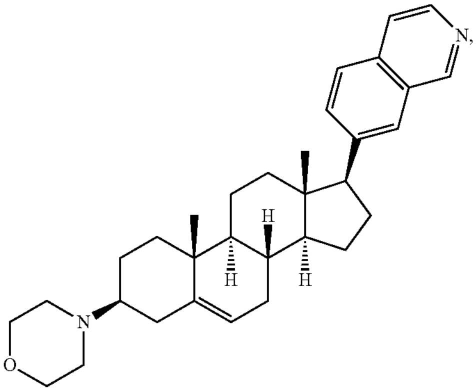
-continued
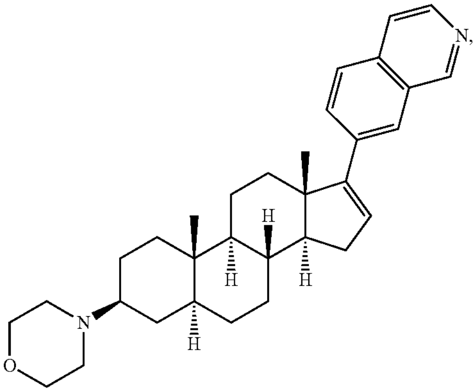
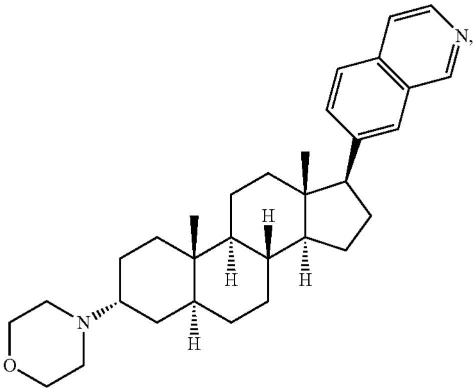
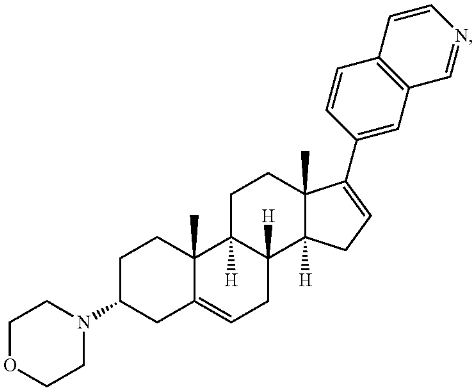
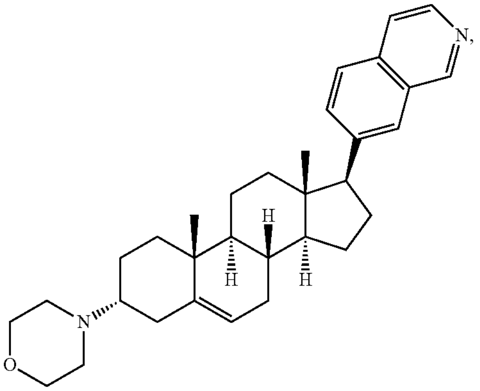
or -continued
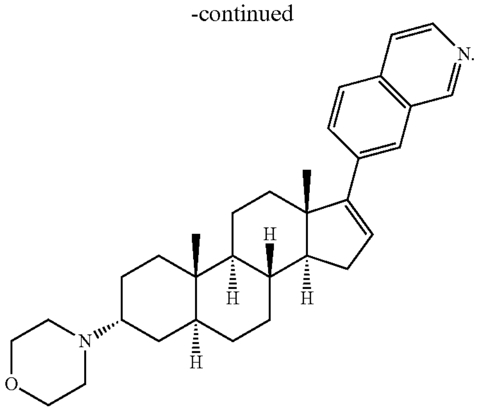
In some embodiments, the compound may be represented by one of:
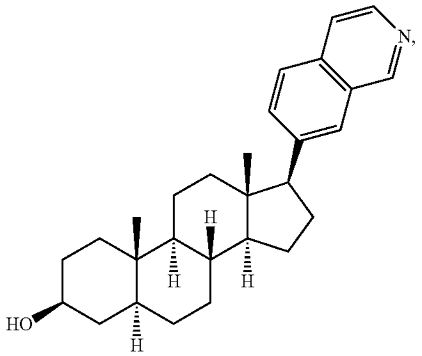
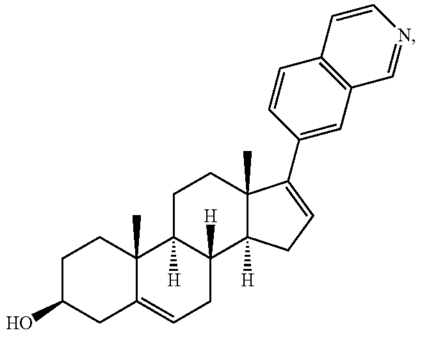
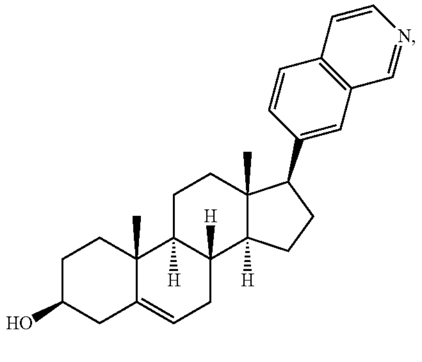
-continued
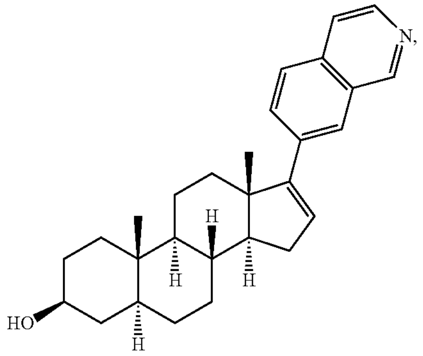
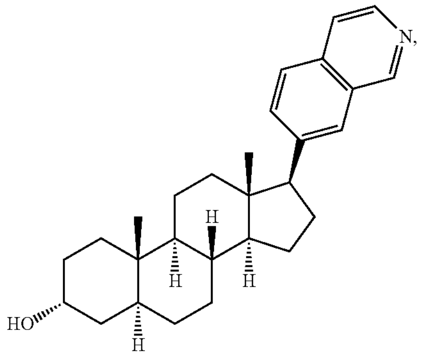
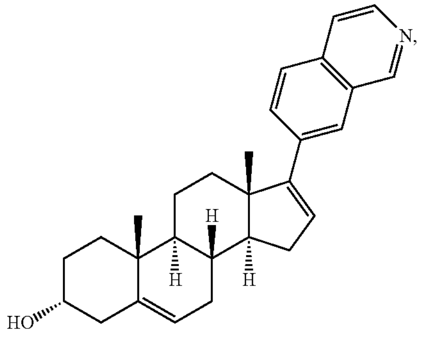
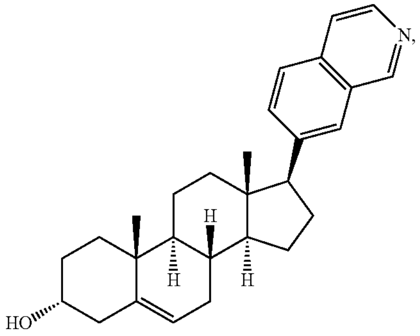
or -continued
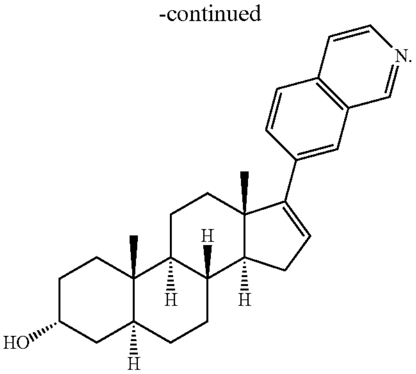.
In some embodiments, the compound may be represented by one of:
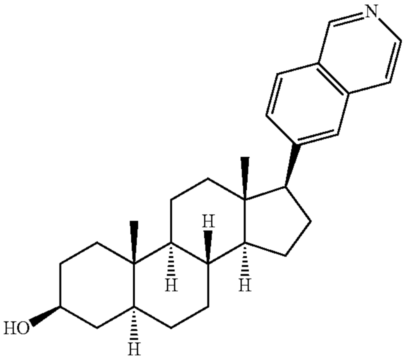,
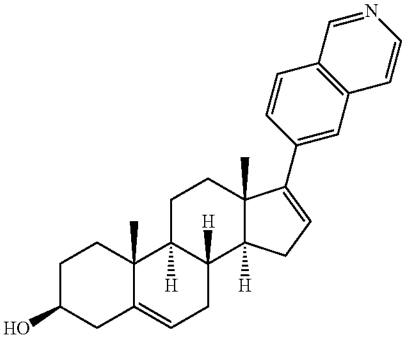,
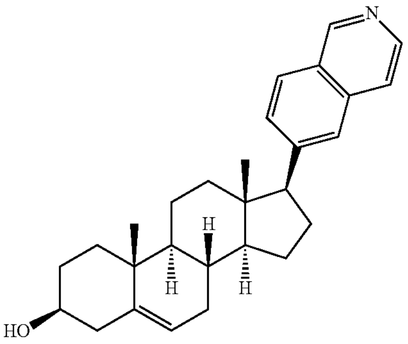,
-continued
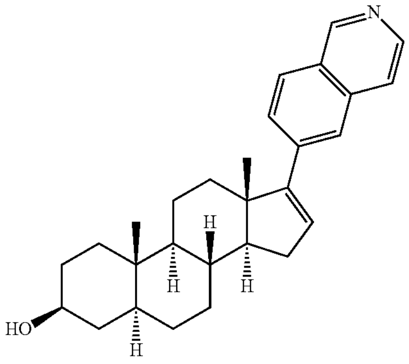,
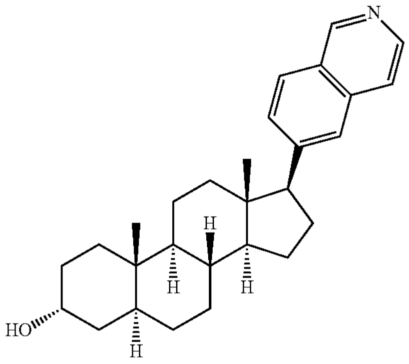,
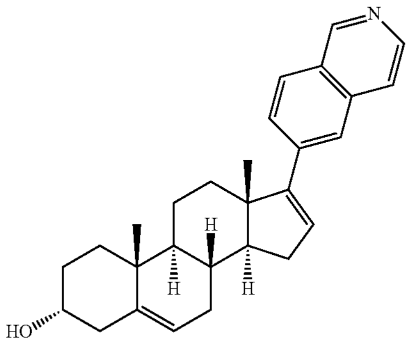,
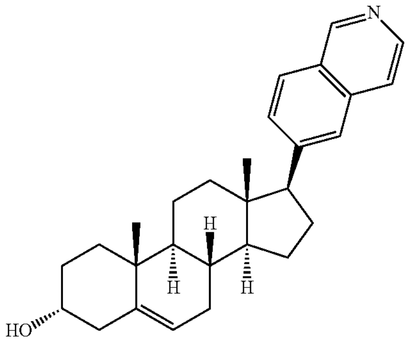, or -continued
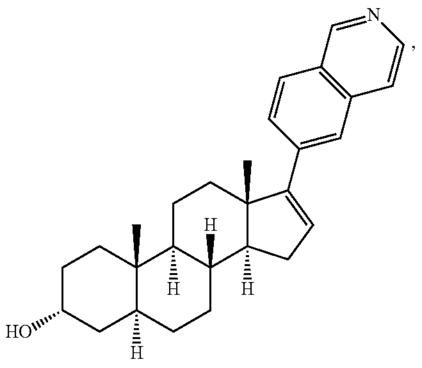
In some embodiments, the compound may be represented by one of:
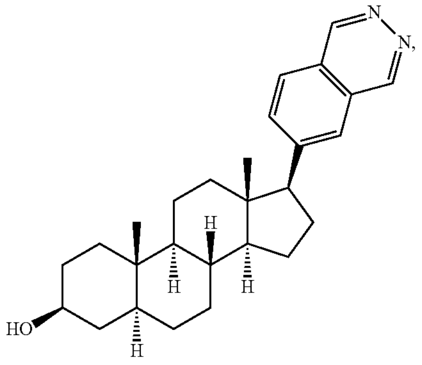
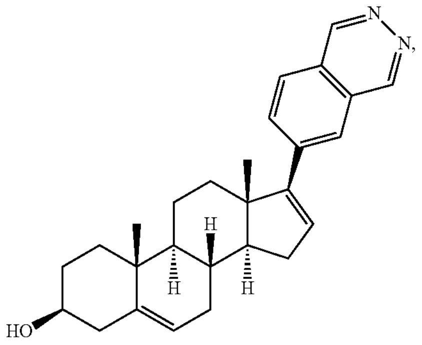
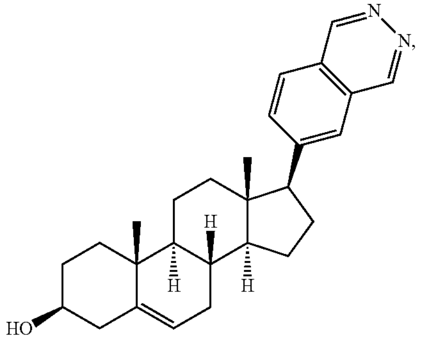
-continued
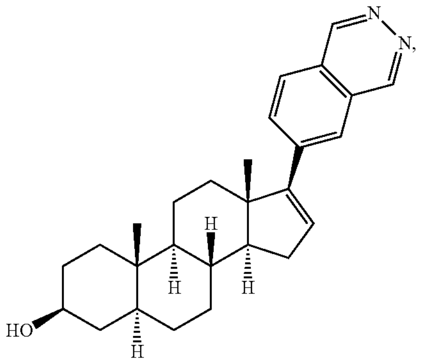
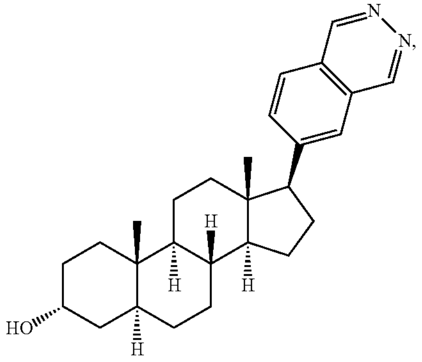
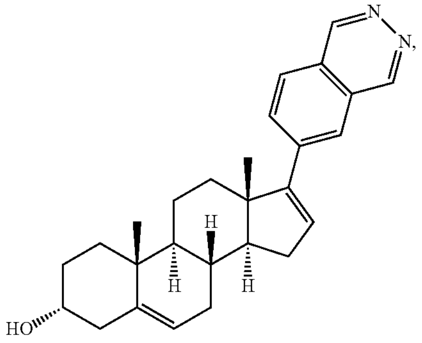
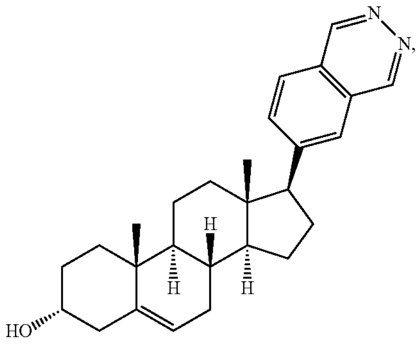
or -continued
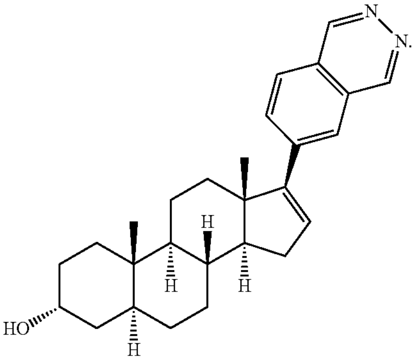
In some embodiments, the compound may be represented by one of:
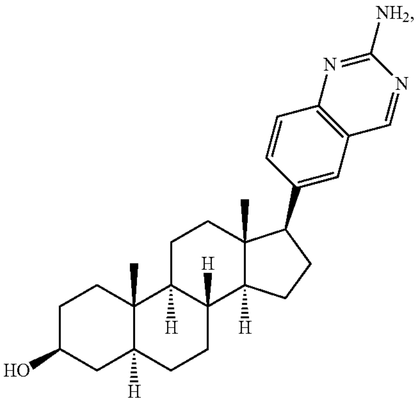
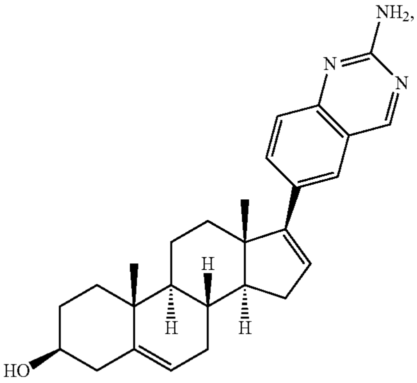
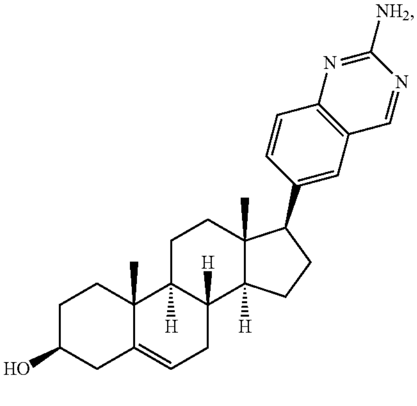
-continued
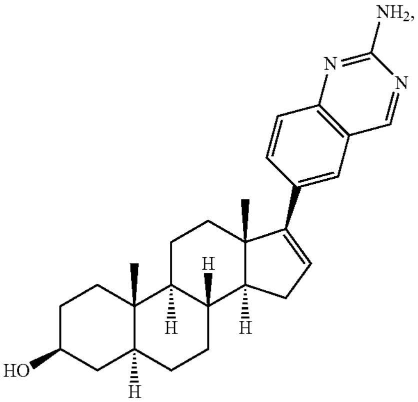
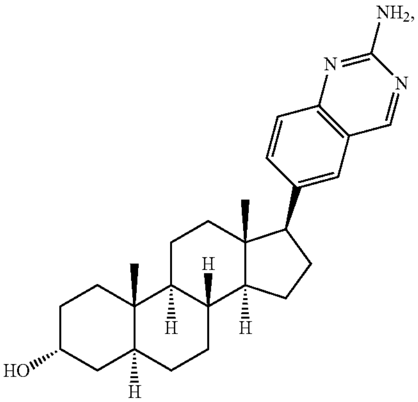
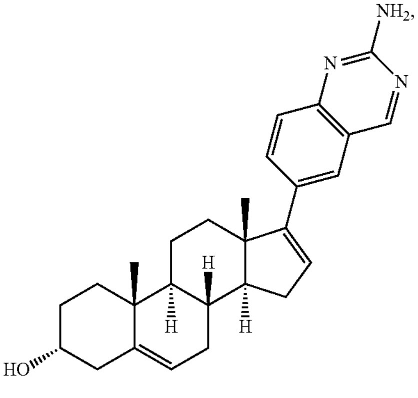
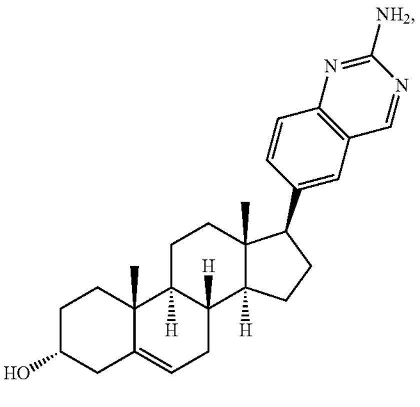
or -continued
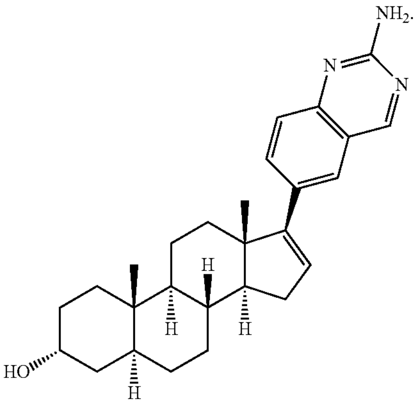
In many embodiments, the compound may be represented by one of:
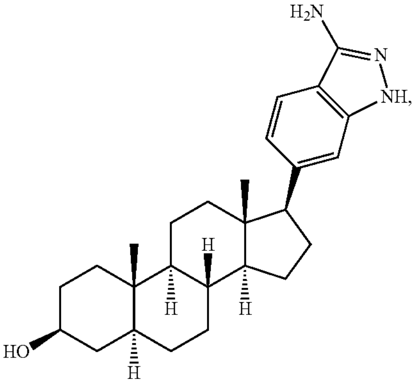
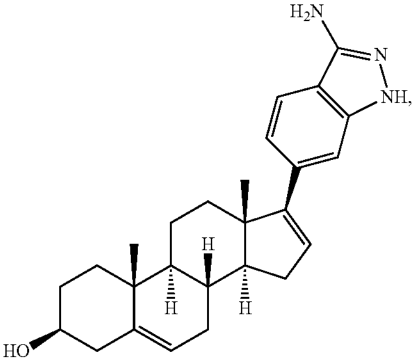
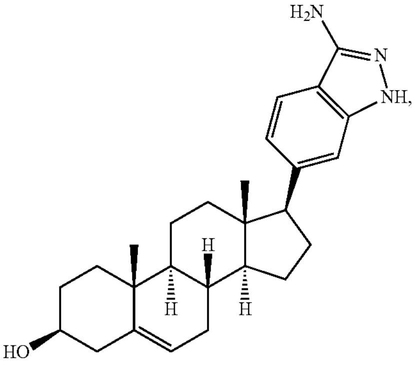
-continued
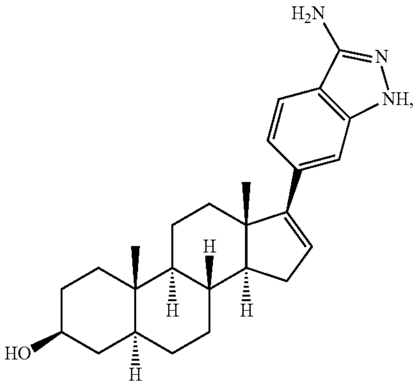
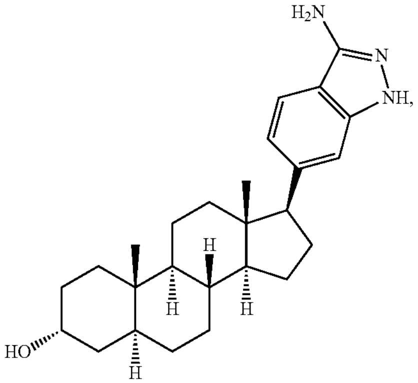
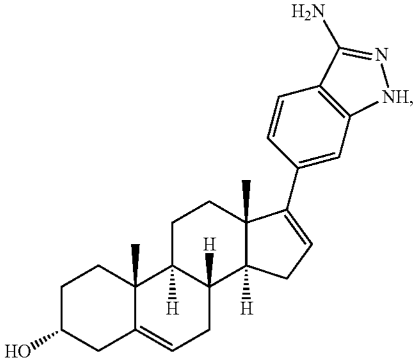
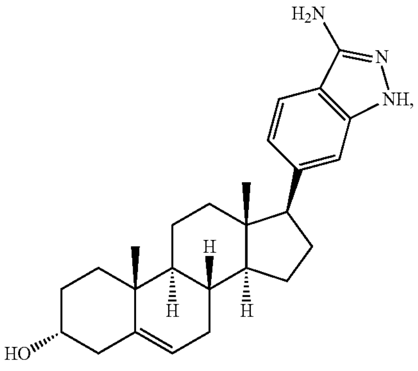
or -continued
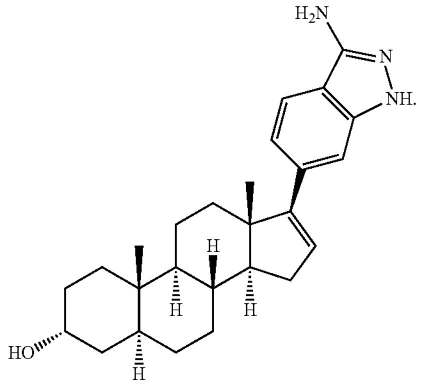
In some embodiments, the compound may be represented by one of:
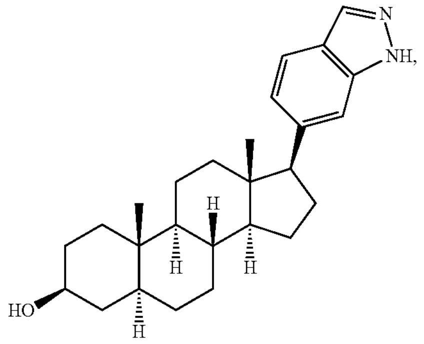
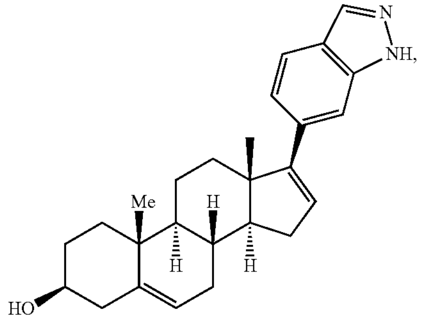
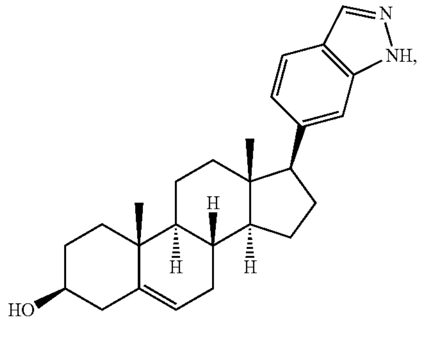
-continued
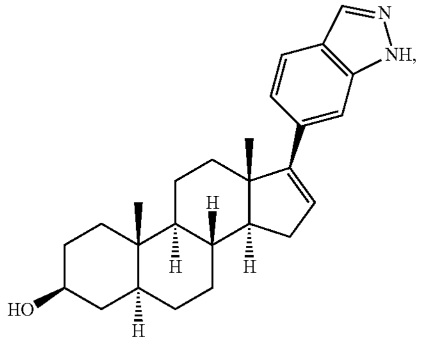
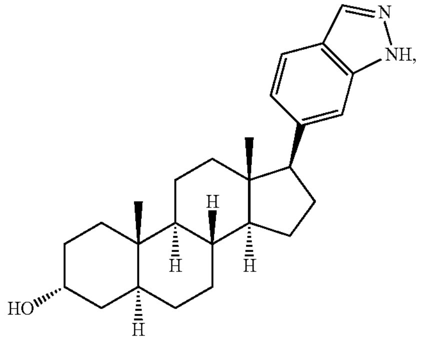
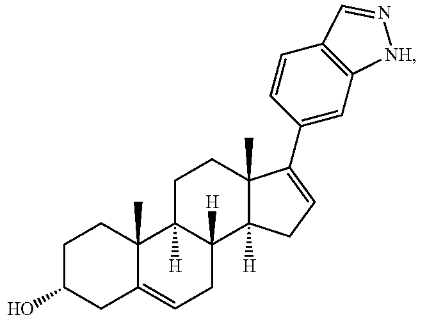
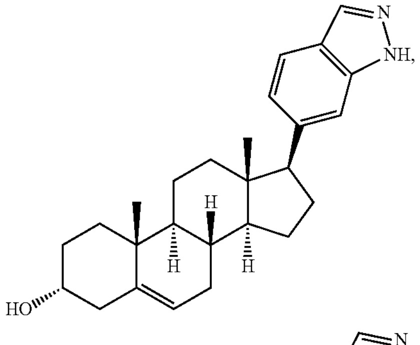
or
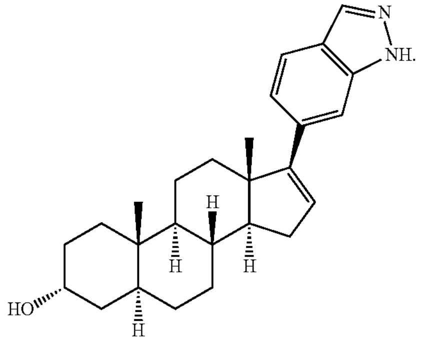

In some embodiments, the compound may be represented by one of:

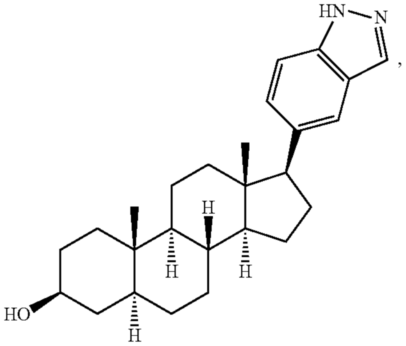

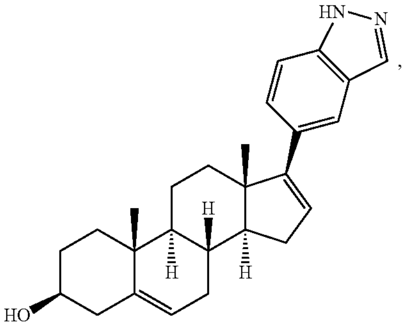

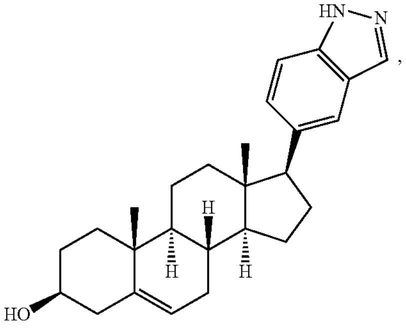

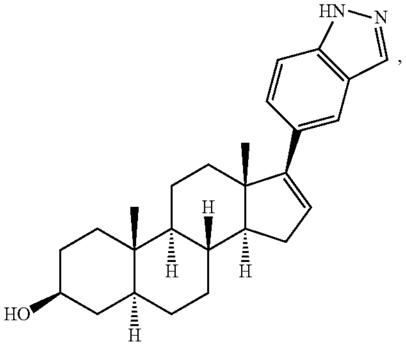

-continued

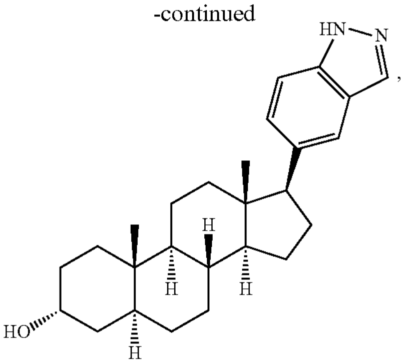

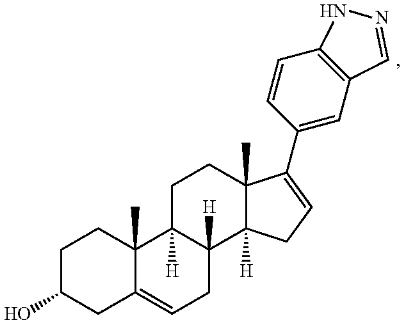

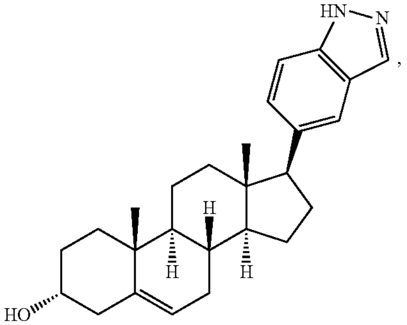

or

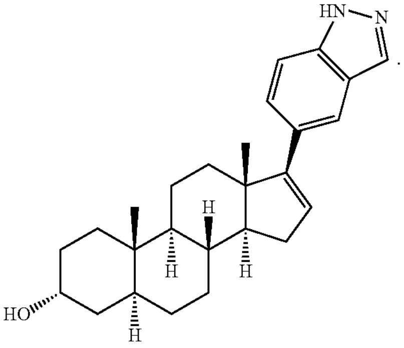

Some of the foregoing compounds can comprise one or more asymmetric centers, and thus can exist in various isomeric forms, e.g., stereoisomers and/or diastereomers. Accordingly, compounds of the application may be in the form of an individual enantiomer, diastereomer or geometric isomer, or may be in the form of a mixture of stereoisomers. In one embodiment, the compounds of the application are enantiopure compounds. In another embodiment, mixtures of stereoisomers or diastereomers are provided.

Another aspect is an isotopically labeled compound of any of the formulae delineated herein. Such compounds have one or more isotope atoms which may or may not be radioactive (e.g., $^{3}H$, $^{2}H$, $^{14}C$, $^{13}C$, $^{18}F$, $^{5}S$, $^{32}P$, $^{125}I$, and $^{131}I$)

introduced into the compound. Such compounds are useful for drug metabolism studies and diagnostics, as well as therapeutic applications.

A compound of the application may be prepared as a pharmaceutically acceptable salt (e.g., protonated) by reacting the free base form of the compound with a pharmaceutically acceptable inorganic or organic acid. Alternatively, a pharmaceutically acceptable salt (e.g., deprotonated) of a compound of the application can be prepared by reacting the free acid form of the compound with a pharmaceutically acceptable inorganic or organic base. The pharmaceutically acceptable salt may include various counterions, e.g., counterions of the inorganic or organic acid, counterions of the inorganic or organic base, or counterions afforded by counterion exchange.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Potency of the inhibitor can also be determined by $IC_{50}$ value. A compound with a lower $IC_{50}$ value, as determined under substantially similar conditions, is a more potent inhibitor relative to a compound with a higher $IC_{50}$ value. In some embodiments, the substantially similar conditions comprise determining a CDK8-dependent phosphorylation level and/or a CDK19-dependent phosphorylation level, in vitro or in vivo (e.g., in cells expressing a wild-type CDK8, a mutant CDK8, a wild-type CDK19, a mutant CDK19, or a fragment of any thereof).

In one embodiment, the compounds of the present application are useful as anticancer agents, and thus may be useful in the treatment of cancer, by effecting tumor cell death or inhibiting the growth of tumor cells. In certain exemplary embodiments, the disclosed anticancer agents are useful in the treatment of cancers and other proliferative disorders, including, but not limited to breast cancer, cervical cancer, colon and rectal cancer, leukemia, lung cancer (e.g., non-small cell lung cancer), melanoma, multiple myeloma, non-Hodgkin's lymphoma, ovarian cancer, pancreatic cancer, prostate cancer, gastric cancer, leukemias (e.g., myeloid, lymphocytic, myelocytic and lymphoblastic leukemias), malignant melanomas, and T-cell lymphoma.

A "selective CDK8 inhibitor" can be identified, for example, by comparing the ability of a compound to inhibit CDK8 kinase activity to its ability to inhibit the other members of the CDK kinase family or other kinases. For example, a substance may be assayed for its ability to inhibit CDK8 kinase activity, as well as CDK1, CDK2, CDK4, CDK6, CDK7, CDK9, CDK11, CDK12, CDK13, CDK14 and other kinases. In some embodiments, the selectivity can be identified by measuring the $EC_{50}$ or $IC_{50}$ of the compounds.

A "selective CDK19 inhibitor" can be identified, for example, by comparing the ability of a compound to inhibit CDK19 kinase activity to its ability to inhibit the other members of the CDK kinase family or other kinases. For example, a substance may be assayed for its ability to inhibit CDK19 kinase activity, as well as CDK1, CDK2, CDK4, CDK6, CDK7, CDK9, CDK11, CDK12, CDK13, CDK14 and other kinases. In some embodiments, the selectivity can be identified by measuring the $EC_{50}$ or $IC_{50}$ of the compounds.

In certain embodiments, the compounds of the application are CDK8 inhibitors that exhibit at least 2-fold, 3-fold, 5-fold, 10-fold, 25-fold, 50-fold or 100-fold selectivity over other kinases (e.g., CDK1, CDK2, CDK4, CDK6, CDK7, CDK9, CDK11, CDK12, CDK13, CDK14, etc.). In various embodiments, the compounds of the application exhibit 1000-fold selectivity over other kinases.

In certain embodiments, the compounds of the application are CDK19 inhibitors that exhibit at least 2-fold, 3-fold, 5-fold, 10-fold, 25-fold, 50-fold or 100-fold selectivity over other kinases (e.g., CDK1, CDK2, CDK4, CDK6, CDK7, CDK9, CDK11, CDK12, CDK13, CDK14, etc.). In various embodiments, the compounds of the application exhibit 1000-fold selectivity over other kinases.

Method of Synthesizing the Compounds

Compounds of the present application can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* $5^{th}$ edition, John Wiley & Sons: New York, 2001; and Greene, T. W., Wuts, P. G. M., *Protective Groups in Organic Synthesis,* $3^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present application. The processes generally provide the desired final compound at or near the end of the overall process, although it may be desirable in certain instances to further convert the compound to a pharmaceutically acceptable salt, ester or prodrug thereof. Suitable synthetic routes are depicted in the schemes below.

Those skilled in the art will recognize if a stereocenter exists in the compounds disclosed herein. Accordingly, the present application includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds of the present application can be prepared in a number of ways well known to those skilled in the art of organic synthesis. By way of example, compounds of the present application can be synthesized using the methods described below, together with synthetic methods known in the art of synthetic organic chemistry, or variations thereon as appreciated by those skilled in the art. Preferred methods include but are not limited to those methods described below.

Compounds of the present application can be synthesized by following the steps outlined in Schemes 1 and 2 which comprise different sequences of assembling intermediates. Starting materials are either commercially available or made by known procedures in the reported literature or as illustrated.

Scheme 1.
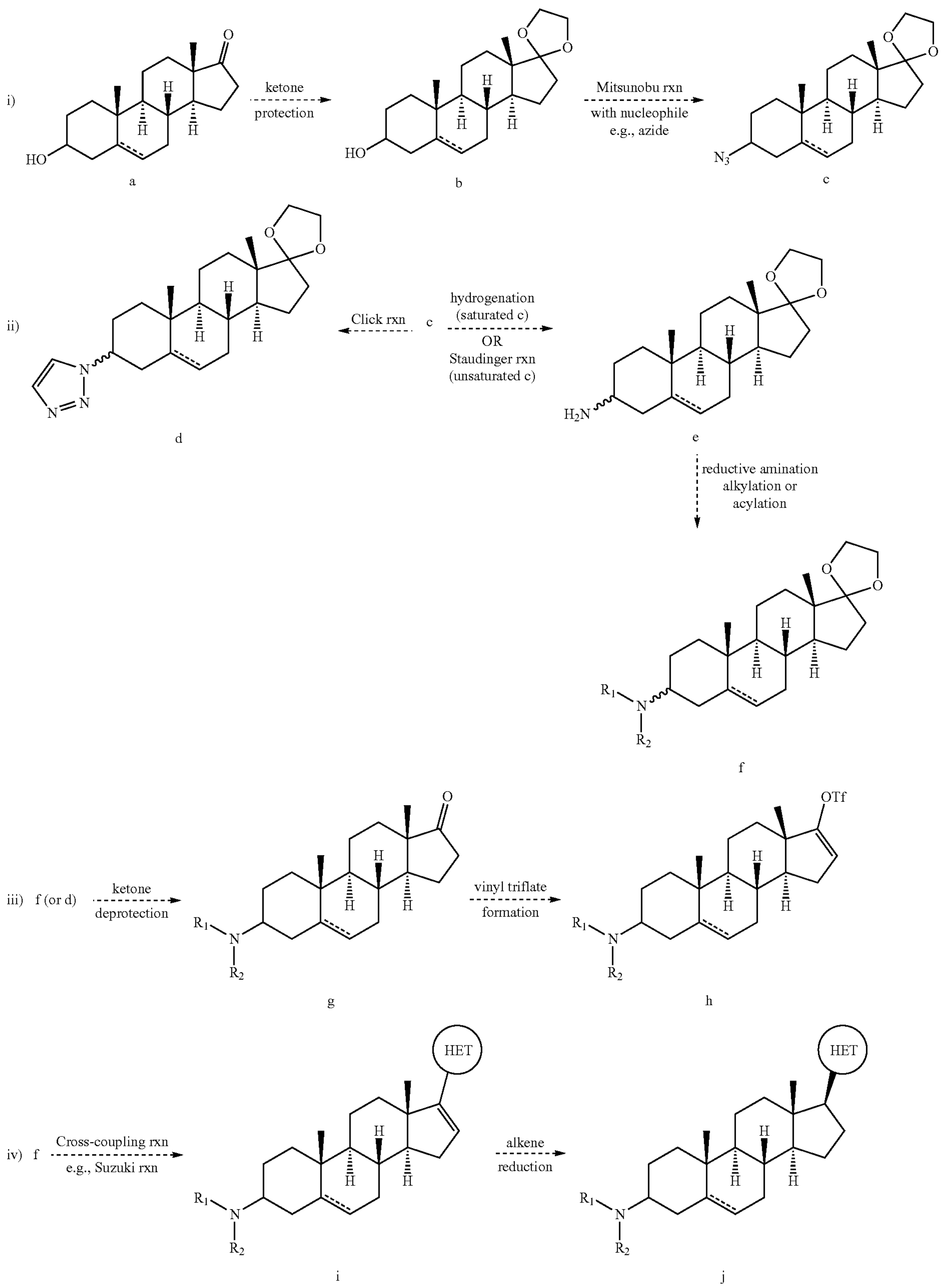

Compound (a) may be obtained commercially as a single stereoisomer, and as either saturated or unsaturated as indicated.

Step i) Compound (a) may be protected as ketal (b), for example, with a suitable diol or thiol in the presence of an acid, e.g., ethylene glycol and tosylic acid. Ketal (b) may be subjected to Mitsunobu conditions (e.g., a phosphine such as triphenylphosphine; an azodicarboxylate such as diethylazodicarboxylate; and a nucleophile such as an azide, e.g., diphenyl phosphoryl azide) to form azide (c). Other nucleophiles may be readily envisioned.

Step ii) Azide (c) may undergo a Click reaction in the presence of a suitable alkyne, such as TMS-acetylene, and a copper catalyst. Azide (c) may also be used to prepare various amino-substituted intermediates. For example, saturated azide (c) may be hydrogenated under standard hydrogenation conditions, e.g., $H_2$ and Pd/C. Unsaturated azide (c) may similarly be reduced under Staudinger conditions to provide amine (e), i.e., by treatment with a phosphine such as trimethylphosphine. Amine (e) may undergo reductive amination and/or alkylation. For example, reductive amination conditions may include imine formation with a suitable aldehyde, e.g., formaldehyde, or ketone, followed by treatment with a reducing agent such as sodium borohydride. For example, alkylation conditions may include treating amine (e), in the presence of a base, with a suitable alkylating agent such as an alkyl halide, e.g., ethyl iodide, 1,4-dibromoethane, or 2-bromoethyl ether. Alternatively, amine (e) may undergo mono-protection prior to alkylation, for example, as the boc amine, by treatment with boc anhydride. Deprotection of a boc amine may be afforded by treatment with an acid, such as trifluoroacetic acid. For example, deprotection may be carried out on compound (i) or (j).

Step iii) The ketones of amine (f) or triazole (d) may be deprotected by treatment with a suitable acid such as tosylic acid and subsequently converted to the corresponding vinyl triflate (h). For example, triflate (h) may be provided by treatment of ketone (g) with a non-nucleophilic base, such as KHMDS, and suitable electrophilic triflate source, such as N-phenyl-bis(trifluoromethanesulfonimide) or triflic anhydride.

Step iv) Triflate (h) may be coupled to a variety of heteroaryl groups ("HET"). For example, triflate (h) may be contacted with a HET-boronic acid or HET-boronate ester in the presence of a suitable palladium catalyst, i.e., Suzuki cross-coupling. Other cross-coupling reactions are readily envisioned, for example contacting triflate (h) with a HET-$Sn(alkyl)_3$ reagent in the presence of a palladium catalyst, i.e., Stille cross-coupling. Compound (i) may further be reduced to afford compound (j), for example, by treatment with a diimide reducing agent, such as potassium azodicarboxylate.

Scheme 2.

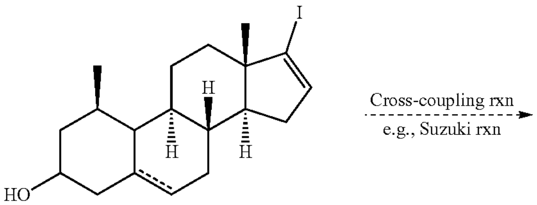

m

-continued

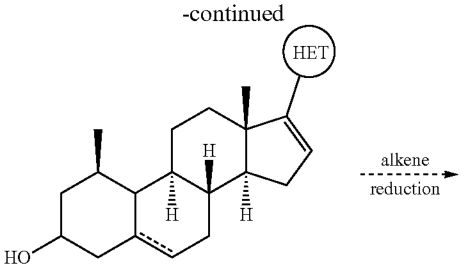

n

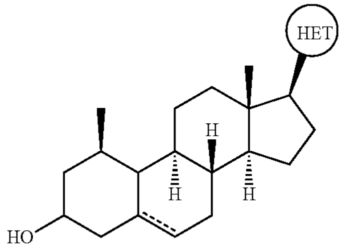

o

Compound (m) may be obtained commercially as a single stereoisomer, and as either saturated or unsaturated as indicated by the figure.

Compound (m) may be subjected to cross-coupling conditions in order to install a suitable heteroaryl group ("HET"), and the resulting compound (n) may further be reduced. Each step may be carried out as described above in Scheme 1.

Biological Assays

The biological activities of the compounds of the present application can be assessed through a variety of methods known in the art. For example, a kinase competitive binding assay may be used to determine the activity of the compounds of the present application to bind to CD8 and/or CD19. In the competitive binding assay, a reporting ligand capable of binding to CD8 and/or CD19, such as a fluoro- or radio-labeled compound, is incubated with CD8 and/or CD19 in the absence of a compound of the present application or with increasing concentrations of the compound. The changes in the signal produced by the reporting ligand when the compound is present relative when the compound is absent are recorded, which are calculated to provide the $IC_{50}$ of the compound.

Pharmaceutical Compositions

In another aspect, a pharmaceutical composition is provided. The pharmaceutical composition comprises a therapeutically effective amount of a compound of the application, or an enantiomer, diastereomer, stereoisomer, or pharmaceutically acceptable salt thereof, and a pharmaceutically acceptable carrier.

Compounds of the application may be administered as pharmaceutical compositions by any conventional route, in particular enterally, e.g., orally, e.g., in the form of tablets or capsules, or parenterally, e.g., in the form of injectable solutions or suspensions, or topically, e.g., in the form of lotions, gels, ointments or creams, or in a nasal or suppository form.

Pharmaceutical compositions including a compound of the present application in free form or in a pharmaceutically acceptable salt form in association with at least one pharmaceutically acceptable carrier or diluent may be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present application with a carrier. A carrier may include absorbable pharmacologically acceptable solvents to assist passage through the skin of the host. For example, transdermal devices may be in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The pharmaceutical compositions of the present application comprise a therapeutically effective amount of a compound of the present application formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which may serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxy propylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this application may be administered to humans and other animals orally, rectally, parenterally, intracisternally, intravaginally, intraperitoneally, topically (as by powders, ointments, or drops), buccally, or as an oral or nasal spray.

Liquid dosage forms for oral administration may include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, com, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous, or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds may also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this application.

The ointments, pastes, creams and gels may contain, in addition to an active compound of this application, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this application, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Methods of Use

In one aspect, the present application provides a method of modulating (e.g., inhibiting) a kinase (e.g., a cyclin-dependent kinase, such as CDK8 and/or CDK19). The method comprises administering to a subject in need thereof an effective amount of a compound of the application or an enantiomer, diastereomer, stereoisomer, or pharmaceutically acceptable salt thereof, or a pharmaceutical composition of the application.

In one aspect, the present application provides a method of modulating (e.g., inhibiting) CDK8 and/or CDK19. The method comprises administering to a subject in need thereof an effective amount of a compound of the application or an enantiomer, diastereomer, stereoisomer, or pharmaceutically acceptable salt thereof, or a pharmaceutical composition of the application.

In some embodiments, the inhibition of CDK8 and/or CDK19 activity is measured by $IC_{50}$. In some embodiments, the inhibition of CDK8 and/or CDK19 activity is measured by $EC_{50}$.

A compound of the present application (e.g., a compound of any of the formulae described herein, or selected from any compounds described herein) is capable of treating or preventing a disease or disorder in which CDK8 and/or CDK 19 plays a role or in which CDK8 and/or CDK19 is deregulated (e.g., overexpressed).

In one aspect, the present application provides a method of treating or preventing a disease responsive to modulation of CDK8 and/or CDK19. The method comprises administering to a subject in need thereof an effective amount of a compound of the application or an enantiomer, diastereomer, stereoisomer, or pharmaceutically acceptable salt thereof, or a pharmaceutical composition of the application.

In one aspect, the present application provides a method of treating or preventing a disease. The method comprises administering to a subject in need thereof an effective amount of a compound of the application or an enantiomer, diastereomer, stereoisomer, or pharmaceutically acceptable salt thereof, or a pharmaceutical composition of the application. In one aspect, the disease is a kinase (e.g., CDK8 and/or CDK19) mediated disorder. In one aspect, the disease is a proliferative disease (e.g., a proliferative disease in which CDK8 and/or CDK19 plays a role).

In one aspect, the present application provides a method of treating or preventing cancer in a subject, wherein the cell of the cancer comprises an activated CDK8 and/or activated CDK19 or wherein the subject is identified as being in need of inhibition of CDK8 and/or CDK19 for the treatment or prevention of cancer. The method comprises administering to the subject an effective amount of a compound of the application or an enantiomer, diastereomer, stereoisomer, or pharmaceutically acceptable salt thereof, or a pharmaceutical composition of the application.

In one embodiment, the disease (e.g., cancer) is mediated by CDK8 and/or CDK19 (e.g., CDK8 and/or CDK19 plays a role in the initiation or development of the disease).

In one embodiment, the CDK8 activation is selected from mutation of CDK8, amplification of CDK8, overexpression of CDK8, and ligand mediated activation of CDK8.

In one embodiment, the CDK19 activation is selected from mutation of CDK19, amplification of CDK19, overexpression of CDK19, and ligand mediated activation of CDK19.

In one embodiment, the present application provides a method of treating or preventing any of the diseases, disorders, and conditions described herein, wherein the subject is a human. In one embodiment, the application provides a method of treating. In one embodiment, the application provides a method of preventing.

As inhibitors of CDK8 and/or CDK19, the compounds and compositions of this application are particularly useful for treating or lessening the severity of a disease, condition, or disorder where a protein kinase is implicated in the disease, condition, or disorder. In one embodiment, the present application provides a method for treating or lessening the severity of a disease, condition, or disorder where a protein kinase is implicated in the disease state. In one embodiment, the present application provides a method for treating or lessening the severity of a kinase disease, condition, or disorder where inhibition of enzymatic activity is implicated in the treatment of the disease. In one embodiment, the present application provides a method for treating or lessening the severity of a disease, condition, or disorder with compounds that inhibit enzymatic activity by binding to the protein kinase. In one embodiment, the present application provides a method for treating or lessening the severity of a kinase disease, condition, or disorder by inhibiting enzymatic activity of the kinase with a protein kinase inhibitor.

In one embodiment, the disease or disorder is cancer or a proliferation disease.

In one embodiment, the disease or disorder is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

In one embodiment, the disease or disorder is inflammation, arthritis, rheumatoid arthritis, spondyiarthropathies, gouty arthritis, osteoarthritis, juvenile arthritis, and other arthritic conditions, systemic lupus erthematosus (SLE), skin-related conditions, psoriasis, eczema, burns, dermatitis, neuroinflammation, allergy, pain, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, cancer, leukemia, lymphoma, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamous cell and/or basal cell cancers, prostate cancer, renal cell carcinoma, and other known cancers that affect epithelial cells throughout the body, chronic myelogenous leukemia (CML), acute myeloid leukemia (AML) and acute promyelocytic leukemia (APL), angiogenesis including neoplasia, metastasis, central nervous system disorders, central nervous system disorders having an inflammatory or apoptotic component, Alzheimer's disease, Parkinson's disease, Huntington's disease, amyotrophic lateral sclerosis, spinal cord injury, peripheral neuropathy, or B-Cell Lymphoma.

In one embodiment, the disease or disorder is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, dermatitis, pain, pulmonary disorders, lung inflammation, adult respiratory distress syndrome, pulmonary sarcoisosis, asthma, chronic pulmonary inflammatory disease, and chronic obstructive pulmonary disease (COPD), cardiovascular disease, arteriosclerosis, myocardial infarction (including post-myocardial infarction indications), congestive heart failure, cardiac reperfusion injury, inflammatory bowel disease, Crohn's disease, gastritis, irritable bowel syndrome, leukemia, or lymphoma.

In one embodiment, the disease or disorder is selected from autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In one embodiment, the disease or disorder is selected from a proliferative disorder and a neurodegenerative disorder.

In one embodiment, the disease or disorder is characterized by excessive or abnormal cell proliferation. Such diseases include, but are not limited to, a proliferative or hyperproliferative disease, and a neurodegenerative disease. Examples of proliferative and hyperproliferative diseases include, without limitation, cancer.

The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colonrectum, large intestine, rectum, brain and central nervous system; chronic myeloid leukemia (CMIL), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

The term "cancer" also refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Cancer may also include colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

Cancer may also include colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In one embodiment, the compounds of this application are useful for treating hematopoietic disorders, in particular, acute-myelogenous leukemia (AML), chronic-myelogenous leukemia (CML), acute-promyelocytic leukemia, and acute lymphocytic leukemia (ALL).

Examples of neurodegenerative diseases include, without limitation, Adrenoleukodystrophy (ALD), Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases, Progressive Supranuclear Palsy, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, and Toxic encephalopathy.

In one aspect, the present application also provides a method of treating or preventing cell proliferative disorders such as hyperplasias, dysplasias, or pre-cancerous lesions. Dysplasia is the earliest form of pre-cancerous lesion recognizable in a biopsy by a pathologist. The compounds of the present application may be administered for the purpose of preventing hyperplasias, dysplasias, or pre-cancerous lesions from continuing to expand or from becoming cancerous. Examples of pre-cancerous lesions may occur in skin, esophageal tissue, breast, and cervical intra-epithelial tissue.

As inhibitors of CDK8 and/or CDK19, the compounds and compositions of this application are also useful in assessing, studying, or testing biological samples. One aspect of the application relates to inhibiting protein kinase activity in a biological sample, comprising contacting the biological sample with a compound or a composition of the application.

The term "biological sample", as used herein, means an in vitro or an ex vivo sample, including, without limitation, cell cultures or extracts thereof, biopsied material obtained from a mammal or extracts thereof; and blood, saliva, urine, feces, semen, tears, or other body fluids or extracts thereof. Inhibition of protein kinase activity in a biological sample is useful for a variety of purposes that are known to one of skill in the art. Examples of such purposes include, but are not limited to, blood transfusion, organ transplantation, and biological specimen storage.

Another aspect of this application relates to the study of CDK8 and/or CDK19 in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds and compositions of the present application as CDK8 and/or CDK19 inhibitors may be assayed in vitro, in vivo, or in a cell line. In vitro assays include assays that determine inhibition of either the kinase activity or ATPase activity of the activated kinase. Alternate in vitro assays quantitate the ability of the inhibitor to bind to the protein kinase and may be measured either by radio labelling the inhibitor prior to binding, isolating the inhibitor/kinase complex and determining the amount of radio label bound, or by running a competition experiment where new inhibitors are incubated with the kinase bound to known radioligands. Detailed conditions for assaying a compound utilized in this application as an inhibitor of various kinases are set forth in the Examples below.

In accordance with the foregoing, the present application provides a method for preventing or treating any of the diseases or disorders described above in a subject in need of such treatment, comprising administering to the subject a therapeutically effective amount of a compound of the application or an enantiomer, diastereomer, stereoisomer, or pharmaceutically acceptable salt thereof, or a pharmaceutical composition of the application. For any of the above uses, the required dosage will vary depending on the mode of administration, the particular condition to be treated and the effect desired.

Compounds and compositions of the application can be administered in therapeutically effective amounts in a combinational therapy with one or more therapeutic agents (pharmaceutical combinations) or modalities, e.g., anti-proliferative, anti-cancer, immunomodulatory or anti-inflammatory agent, and/or non-drug therapies, etc. For example, synergistic effects can occur with anti-proliferative, anti-cancer, immunomodulatory or anti-inflammatory substances. Where the compounds of the application are administered in conjunction with other therapies, dosages of the co-administered compounds will of course vary depending on the type of co-drug employed, on the specific drug employed, on the condition being treated and so forth.

Combination therapy may include the administration of the subject compounds in further combination with one or more other biologically active ingredients (such as, but not limited to, a second CDK8 inhibitor, a second CDK19 inhibitor, a second and different antineoplastic agent, a second cyclin-dependent kinase inhibitor (i.e., CDK1, CDK2, CDK4, CDK6, CDK7, CDK9, CDK11, CDK12, CDK13, CDK14, etc.) and non-drug therapies (such as, but not limited to, surgery or radiation treatment). For instance, the compounds of the application can be used in combination with other pharmaceutically active compounds, preferably compounds that are able to enhance the effect of the compounds of the application. The compounds of the application can be administered simultaneously (as a single preparation or separate preparation) or sequentially to the other drug therapy or treatment modality. In general, a combination therapy envisions administration of two or more drugs during a single cycle or course of therapy.

In one embodiment, the compounds may be administered in combination with one or more separate pharmaceutical agents, e.g., a chemotherapeutic agent, an immunotherapeutic agent, or an adjunctive therapeutic agent.

Another aspect of the present application relates to a kit comprising a compound of the application or an enantiomer, diastereomer, stereoisomer, or pharmaceutically acceptable salt thereof, or a pharmaceutical composition of the application.

Another aspect of the present application relates to a compound of the application or an enantiomer, diastereomer, stereoisomer, or pharmaceutically acceptable salt thereof, or a pharmaceutical composition of the application, for use in the manufacture of a medicament for modulating (e.g., inhibiting) a kinase (e.g., a cyclin-dependent kinase, such as CDK8 and/or CDK19), for treating or preventing a disease (e.g., a disease in which CDK8 and/or CDK19 plays a role), or for treating or preventing cancer in a subject, wherein the cell of the cancer comprises an activated CDK8 and/or activated CDK19 or wherein the subject is identified as being in need of inhibition of CDK8 and/or CDK19 for the treatment or prevention of cancer.

Another aspect of the present application relates to use of a compound of the application or an enantiomer, diastereomer, stereoisomer, or pharmaceutically acceptable salt thereof, or a pharmaceutical composition of the application, in the manufacture of a medicament for modulating (e.g., inhibiting) a kinase (e.g., a cyclin-dependent kinase, such as CDK8 and/or CDK19), for treating or preventing a disease (e.g., a disease in which CDK8 and/or CDK19 plays a role), or for treating or preventing cancer in a subject, wherein the cell of the cancer comprises an activated CDK8 and/or activated CDK19 or wherein the subject is identified as being in need of inhibition of CDK8 and/or CDK19 for the treatment or prevention of cancer.

Another aspect of the present application relates to a compound of the application or an enantiomer, diastereomer, stereoisomer, or pharmaceutically acceptable salt thereof, or a pharmaceutical composition of the application, for use in modulating (e.g., inhibiting) a kinase (e.g., a cyclin-dependent kinase, such as CDK8 and/or CDK19), in treating or preventing a disease (e.g., a disease in which CDK8 and/or CDK19 plays a role), or in treating or preventing cancer in a subject, wherein the cell of the cancer comprises an activated CDK8 and/or activated CDK19 or wherein the subject is identified as being in need of inhibition of CDK8 and/or CDK19 for the treatment or prevention of cancer.

Another aspect of the present application relates to use of a compound of the application or an enantiomer, diastereomer, stereoisomer, or pharmaceutically acceptable salt thereof, or a pharmaceutical composition of the application, in modulating (e.g., inhibiting) a kinase (e.g., a cyclin-dependent kinase, such as CDK8 and/or CDK19), in treating or preventing a disease (e.g., a disease in which CDK8 and/or CDK19 plays a role), or in treating or preventing cancer in a subject, wherein the cell of the cancer comprises an activated CDK8 and/or activated CDK19 or wherein the subject is identified as being in need of inhibition of CDK8 and/or CDK19 for the treatment or prevention of cancer.

Definitions

Listed below are definitions of various terms used in this application. These definitions apply to the terms as they are used throughout this specification and claims, unless otherwise limited in specific instances, either individually or as part of a larger group.

The term "alkyl," as used herein, refers to saturated, straight or branched-chain hydrocarbon radicals containing, in certain embodiments, between one and six carbon atoms.

Examples of C1-C6 alkyl radicals include, but are not limited to, methyl, ethyl, propyl, isopropyl, n-butyl, tert-butyl, neopentyl, and n-hexyl radicals.

The term "alkenyl," as used herein, denotes a monovalent group derived from a hydrocarbon moiety containing, in certain embodiments, from two to six carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl and the like.

The term "alkoxy" refers to an —O-alkyl radical.

The terms "hal," "halo," and "halogen," as used herein, refer to an atom selected from fluorine, chlorine, bromine and iodine.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, indenyl and the like.

The term "aralkyl," as used herein, refers to an alkyl residue attached to an aryl ring. Examples include, but are not limited to, benzyl, phenethyl and the like.

The term "cycloalkyl," as used herein, denotes a monovalent group derived from a monocyclic or polycyclic saturated or partially unsaturated carbocyclic ring compound.

Examples of $C_3$-$C_8$ cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl. Also contemplated is a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O, and N; zero, one, or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, indazoyl, cinnolinyl, phthalazinyl, pyridazinyl, indolyl, acridinyl, benzoquinolinyl, pyrimidinyl, a purinyl, pyrrolopyrimidinyl, quinoxalinyl, quinazolinyl, indazolinyl, and phthalazinyl, and the like.

The term "heteroaralkyl," as used herein, refers to an alkyl residue attached to a heteroaryl ring. Examples include, but are not limited to, pyridinylmethyl, pyrimidinylethyl and the like.

The term "heterocyclyl," or "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, and (iv) the nitrogen heteroatom may optionally be quaternized. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure —NH($C_1$-$C_{12}$ alkyl), e.g., —NH($C_1$-$C_6$ alkyl), where $C_1$-$C_{12}$ alkyl is as previously defined.

The term "dialkylamino" refers to a group having the structure —N($C_1$-$C_{12}$ alkyl)$_2$, e.g., —NH($C_1$-$C_6$ alkyl), where $C_1$-$C_{12}$ alkyl is as previously defined.

The term "acyl" includes residues derived from acids, including but not limited to carboxylic acids, carbamic acids, carbonic acids, sulfonic acids, and phosphorous acids.

Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

In accordance with the application, any of the aryls, substituted aryls, heteroaryls and substituted heteroaryls described herein, can be any aromatic group. Aromatic groups can be substituted or unsubstituted.

The terms "hal," "halo," and "halogen," as used herein, refer to an atom selected from fluorine, chlorine, bromine and iodine.

As described herein, compounds of the application and moieties present in the compounds may optionally be substituted with one or more substituents, such as are illustrated generally above, or as exemplified by particular classes, subclasses, and species of the application. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:

—F, —CI, —Br, —I, —OH, protected hydroxy, —$NO_2$, —CN, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH— $C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —$NHCO_2$—$C_3$-$C_{12}$-cycloalkyl, —$NHCO_2$-aryl, —$NHCO_2$-heteroaryl, —$NHCO_2$-heterocycloalkyl, NHC(O)$NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, NHC(O)NH-heterocycloalkyl, —NHC(S)$NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH— $C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NHheterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, C(NH)NH—$C_3$-$C_{12}$-cycloalkyl, —C(NH)NH-aryl, —C(NH)NH-heteroaryl, —C(NH)NHheterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl-$SO_2NH_2$, —$SO_2NH$—$C_1$-$C_{12}$-alkyl, —$SO_2NH$—$C_2$-$C_{12}$-alkenyl, —$SO_2NH$—$C_2$-$C_{12}$-alkenyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkenyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl.

It is understood that the aryls, heteroaryls, alkyls, and the like can be substituted.

The term "cancer" includes, but is not limited to, the following cancers: epidermoid oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma, and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal, rectum; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions.

The term "CDK8" herein refers to cyclin-dependent kinase 8.

The term "CDK19" herein refers to cyclin-dependent kinase 19.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

"Treat", "treating" and "treatment" refer to a method of alleviating or abating a disease and/or its attendant symptoms.

As used herein, "preventing" or "prevent" describes reducing or eliminating the onset of the symptoms or complications of the disease, condition or disorder.

The terms "disease(s)", "disorder(s)", and "condition(s)" are used interchangeably, unless the context clearly dictates otherwise.

The term "therapeutically effective amount" of a compound or pharmaceutical composition of the application, as used herein, means a sufficient amount of the compound or pharmaceutical composition so as to decrease the symptoms of a disorder in a subject. As is well understood in the medical arts a therapeutically effective amount of a compound or pharmaceutical composition of this application will be at a reasonable benefit/risk ratio applicable to any medical treatment. It will be understood, however, that the total daily usage of the compounds and compositions of the present application will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

As used herein, the term "pharmaceutically acceptable salt" refers to those salts of the compounds formed by the process of the present application which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences,* 66: 1-19 (1977). The salts can be prepared in situ during the final isolation and purification of the compounds of the application, or separately by reacting the free base or acid function with a suitable acid or base.

Examples of pharmaceutically acceptable salts include, but are not limited to, nontoxic acid addition salts: salts formed with inorganic acids such as hydrochloric acid, hydrobromic acid, phosphoric acid, sulfuric acid and perchloric acid, or with organic acids such as acetic acid, maleic acid, tartaric acid, citric acid, succinic acid or malonic acid. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, 7-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present application which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein, refers to those prodrugs of the compounds formed by the process of the present application which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present application. "Prodrug", as used herein, means a compound which is convertible in vivo by metabolic means (e.g., by hydrolysis) to afford any compound delineated by the formulae of the instant application. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This application also encompasses pharmaceutical compositions containing, and methods of treating disorders through administering, pharmaceutically acceptable prodrugs of compounds of the application. For example, compounds of the application having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the application. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in *Advanced Drug Delivery Reviews,* 1996, 19, 1-15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

The application also provides for a pharmaceutical composition comprising a therapeutically effective amount of a compound of the application, or an enantiomer, diastereomer, stereoisomer, or pharmaceutically acceptable salt thereof, and a pharmaceutically acceptable carrier.

In another aspect, the application provides a kit comprising a compound capable of inhibiting CDK8 and/or CDK19 activity selected from one or more compounds disclosed herein, or an enantiomer, diastereomer, stereoisomer, or pharmaceutically acceptable salt thereof, optionally in combination with a second agent and instructions for use.

In another aspect, the application provides a method of synthesizing a compound disclosed herein. The synthesis of the compounds of the application can be found herein and in the Examples below. Other embodiments are a method of making a compound of any of the formulae herein using any one, or combination of, reactions delineated herein. The method can include the use of one or more intermediates or chemical reagents delineated herein.

Another aspect is an isotopically labeled compound of any of the formulae delineated herein. Such compounds have one or more isotope atoms which may or may not be radioactive (e.g., $^{3}H$, $^{2}H$, $^{14}C$, $^{13}C$, $^{18}F$, $^{5}S$, $^{32}P$, $^{125}I$, and $^{131}I$) introduced into the compound. Such compounds are useful for drug metabolism studies and diagnostics, as well as therapeutic applications.

A compound of the application can be prepared as a pharmaceutically acceptable acid addition salt by reacting the free base form of the compound with a pharmaceutically acceptable inorganic or organic acid. Alternatively, a pharmaceutically acceptable base addition salt of a compound of the application can be prepared by reacting the free acid form of the compound with a pharmaceutically acceptable inorganic or organic base. Alternatively, the salt forms of the compounds of the application can be prepared using salts of the starting materials or intermediates. The free acid or free base forms of the compounds of the application can be prepared from the corresponding base addition salt or acid addition salt from, respectively. For example, a compound of the application in an acid addition salt form can be converted to the corresponding free base by treating with a suitable base (e.g., ammonium hydroxide solution, sodium hydroxide, and the like). A compound of the application in a base addition salt form can be converted to the corresponding free acid by treating with a suitable acid (e.g., hydrochloric acid, etc.).

Prodrugs of the compounds of the application can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the application with a suitable carbamylating agent (e.g., 1,1-acyloxyalkylcarbanochloridate, para-nitrophenyl carbonate, or the like).

Protected derivatives of the compounds of the application can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present application can be conveniently prepared, or formed during the process of the application, as solvates (e.g., hydrates). Hydrates of compounds of the present application can be conveniently prepared by recrystallization from an aqueous/organic solvent mixture, using organic solvents such as dioxin, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Combinations of substituents and variables envisioned by this application are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

When any variable (e.g., $R_1$) occurs more than one time in any constituent or formula for a compound, its definition at each occurrence is independent of its definition at every other occurrence. Thus, for example, if a group is shown to be substituted with one or more R moieties, then R at each occurrence is selected independently from the definition of R. Also, combinations of substituents and/or variables are permissible, but only if such combinations result in stable compounds within a designated atom's normal valency.

In addition, some of the compounds of this application have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. When the compounds described herein contain olefinic double bonds or other centers of geometric asymmetry, and unless specified otherwise, it is intended that the compounds include both E and Z geometric isomers. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present application.

Optical isomers may be prepared from their respective optically active precursors by the procedures described herein, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981).

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four non-identical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center, e.g., carbon. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds.

Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. The compounds of this application may also be represented in multiple tautomeric forms, in such instances, the application expressly includes all tautomeric forms of the compounds described herein (e.g., alkylation of a ring system may result in alkylation at multiple sites, the application expressly includes all such reaction products).

In the present application, the structural formula of the compound represents a certain isomer for convenience in some cases, but the present application includes all isomers, such as geometrical isomers, optical isomers based on an asymmetrical carbon, stereoisomers, tautomers, and the like. In the present specification, the structural formula of the compound represents a certain isomer for convenience in some cases, but the present application includes all isomers, such as geometrical isomers, optical isomers based on an asymmetrical carbon, stereoisomers, tautomers, and the like.

Additionally, the compounds of the present application, for example, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present application. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds of this application may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the application are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

EXAMPLES

Analytical Methods, Materials, and Instrumentation

All reactions were monitored by thin layer chromatography (TLC) with 0.25 mm E. Merck pre-coated silica gel plates (60 $F_{254}$), WATERS® LCMS system (WATERS® 2489 UV/Visible Detector, WATERS® 3100 Mass, WATERS® 515 HPLC pump, WATERS® 2545 Binary Gradient Module, WATERS® Reagent Manager, WATERS® 2767 Sample Manager) using SUNFIRE™ C18 column (4.6×50 mm, 5 μm particle size): solvent gradient=100% A at 0 min, 1% A at 5 min; solvent A=0.035% TFA in Water; solvent B=0.035% TFA in MeOH; flow rate: 2.5 mL/min, and/or WATERS® ACQUITY UPLC®/MS system (WATERS® PDA eλ Detector, QDa Detector, Sample manager—FL, Binary Solvent Manager) using ACQUITY UPLC® BEH C18 column (2.1×50 mm, 1.7 μm particle size): solvent gradient=90% A at 0 min, 1% A at 1.8 min; solvent A=0.1% formic acid in Water; solvent B=0.1% formic acid in Acetonitrile; flow rate: 0.6 mL/min. Reaction products were purified by flash column chromatography using COMBIFLASH©Rf with Teledyne Isco REDISEP® Rf High Performance Gold or Silicycle SILIASEP™ High Performance columns (4 g, 12 g, 24 g, 40 g, or 80 g), WATERS® HPLC system using SUNFIRE™ Prep C18 column (19×100 mm, 5 μm particle size): solvent gradient=80% A at 0 min, 5% A at 25 min; solvent A=0.035% TFA in Water; solvent B=0.035% TFA in MeOH; flow rate: 25 mL/min (Method A), and WATERS® ACQUITY UPLC®/MS system (WATERS® PDA eλ Detector, QDa Detector, Sample manager—FL, Binary Solvent Manager) using ACQUITY UPLC® BEH C18 column (2.1×50 mm, 1.7 μm particle size): solvent gradient=80% A at 0 min, 5% A at 2 min; solvent A=0.1% formic acid in Water; solvent B=0.1% formic acid in Acetonitrile; flow rate: 0.6 mL/min (method B). The purity of all compounds was over 95% and was analyzed with WATERS® LCMS system. $^1$H NMR was obtained using a 500 MHz Bruker Avance III. Chemical shifts are reported relative to dimethyl sulfoxide (δ=2.50) or chloroform (δ=7.26) for $^1H$ NMR. Data are reported as (br=broad, s=singlet, d=doublet, t=triplet, q=quartet, m=multiplet).

Abbreviations used in the following examples and elsewhere herein are:

AcOH acetic acid
atm atmosphere
BOC2O di-tert-butyl dicarbonate
br broad
$CuSO_4$ copper sulfate
$CDCl_3$ deuterated chloroform
DCM dichloromethane
DIEA N,N-diisopropylethylamine
DMA N,N-dimethylacetamide
DMAP 4-dimethylaminopyridine
DMF N,N-dimethylformamide
DMSO dimethyl sulfoxide
DMSO-$d_6$ deuterated dimethyl sulfoxide
EDCI 1-ethyl-3-(3-dimethylaminopropyl) carbodiimide
ESI electrospray ionization
EtOAc ethyl acetate
HCl hydrochloric acid
h hour(s)
HATU bis(dimethylamino)methylene]-1H-1,2,3-triazolo [4,5-b]pyridinium 3-oxide hexafluoro-phosphate
HPLC high-performance liquid chromatography
KHMDS potassium hexamethylsilazide
LCMS liquid chromatography-mass spectrometry
m multiplet
mL milliliter
MeCN acetonitrile
MeOH methanol
mg milligram
mmol millimole
$MgSO_4$ magnesium sulfate
MHz megahertz
min minutes
MS mass spectrometry
$Na_2CO_3$ sodium carbonate
$NaHCO_3$ sodium bicarbonate
NMR nuclear magnetic resonance
Tf triflate
$Pd_2(dba)_3$ tris(dibenzylideneacetone)dipalladium(0)
$Pd(PPh_3)_2Cl_2$ bis(triphenylphosphine)palladium(II) dichloride
$PhN(SO_2CF_3)_2$ N-phenyl-bis(trifluoromethanesulfonamide
$PMe_3$ trimethylphosphine
ppm parts per million
PTSA para-toluene sulfonic acid
rt room temperature
TBAF tetra-n-butylammonium fluoride
t-BuOH tert-butanol
TFA trifluoroacetic acid
TMS trimethylsilane
THF tetrahydrofuran
TLC thin layer chromatography
L microliter
Xphos 2-dicyclohexylphosphino-2',4',6'-triisopropylbiphenyl Example 1: (3S,8R,9S,10R,13S,14S)-17-(isoquinolin-7-yl)-10,13-dimethyl-2,3,4,7,8,9,10,11,12,13,14,15-dodecahydro-1H-cyclopenta[a]phenanthren-3-ol (1)

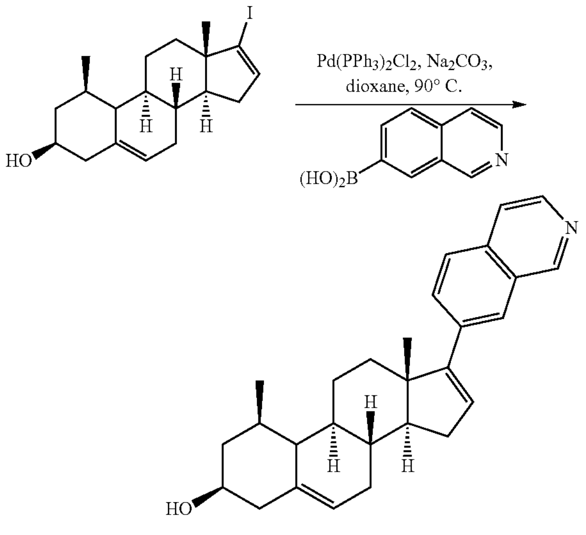

1

To a solution of (3S,8R,9S,10R,13S,14S)-17-iodo-10,13-dimethyl-2,3,4,7,8,9,10,11,12,13,14,15-dodecahydro-1H-cyclopenta[a]phenanthren-3-ol (50 mg, 0.13 mmol) in 1,4-dioxane (5 mL) and $Na_2CO_3$ 2M aq. (0.32 mL, 0.63 mmol) was added isoquinolin-7-ylboronic acid (25 mg, 0.14 mmol). The solution was thoroughly degassed and then $Pd(PPh_3)_2Cl_2$ (5 mg, 0.006 mmol) was added and the mixture was heated to 90° C. for 1 hour. The reaction was quenched with $H_2O$ and extracted with EtOAc (3×50 mL), dried over $MgSO_4$, and condensed to give a brown oil that was purified by reverse phase chromatography using a gradient of 1-90% MeCN in $H_2O$ to give the title compound (1) as a beige solid (40 mg, 80% yield). $^1H$ NMR (500 MHz, DMSO-$d_6$): δ 9.66 (s, 1H), 8.55 (d, J=5 Hz, 1H), 8.35 (s, 1H), 8.20 (d, J=6 Hz, 1H), 8.13 (s, 2H), 6.39 (s, 1H), 5.33 (s, 1H), 3.28 (m, 1H), 3.17 (s, 1H), 2.38-1.99 (m, 6H), 1.81-1.52 (m, 8H), 1.45-1.33 (m, 3H), 1.15 (s, 3H), 1.03 (s, 3H). MS m/z 400.39 $[M+H]^+$.

Compounds 2-7 in Table 1 above were prepared by this procedure from appropriate starting materials and appropriate boronic ester/acid.

Compound 2:

76% yield. $^1H$ NMR (500 MHz, DMSO-$d_6$): δ 9.65 (s, 1H), 8.56 (d, J=5 Hz, 1H), 8.32 (s, 1H), 8.17 (d, J=6 Hz, 1H), 8.12 (s, 2H), 6.37 (s, 1H), 3.38 (m, 1H), 3.17 (s, 1H), 2.41-2.22 (m, 3H), 1.75-1.14 (m, 17H), 1.11 (s, 3H), 0.84 (s, 3H). LCMS m/z 401.74 $[M+H]^+$.

Compound 3:

68% yield. $^1H$ NMR (500 MHz, DMSO-$d_6$): δ 9.86 (s, 1H), 9.80 (s, 1H), 8.28 (s, 1H), 8.24 (d, J=6 Hz, 2H), 6.51 (s, 1H), 5.34 (s, 1H), 3.26 (m, 1H), 3.17 (s, 1H), 2.41-1.87 (m, 6H), 1.83-1.54 (m, 8H), 1.41-1.30 (m, 3H), 1.11 (s, 3H), 1.01 (s, 3H). LCMS m/z 400.86 $[M+H]^+$.

Compound 4:

60% yield. $^1$H NMR (500 MHz, DMSO-$d_6$): δ 9.38 (s, 1H), 8.06 (br, 2H), 7.89 (s, 1H), 7.80 (d, J=6 Hz, 1H), 7.54 (d, J=6 Hz, 1H) 6.34 (s, 1H), 5.32 (s, 1H), 3.29 (m, 1H), 3.17 (s, 1H), 1.83-1.21 (m, 17H), 0.93 (s, 3H), 0.44 (s, 3H). LCMS m/z 416.37 $[M+H]^+$.

Compound 5:

54% yield. $^1$H NMR (500 MHz, DMSO-$d_6$): δ 12.96 (s, 1H), 7.94 (s, 1H), 7.48 (s, 1H), 7.40 (d, J=6 Hz, 1H), 7.19 (d, J=6 Hz, 1H), 6.39 (s, 1H), 5.30 (s, 1H), 5.12 (s, 1H), 4.63 (s, 1H), 3.27 (m, 1H), 2.22-1.20 (m, 18H), 0.93 (s, 3H), 0.43 (s, 3H). LCMS m/z 403.61 $[M+H]^+$.

Compound 6:

58% yield. $^1$H NMR (500 MHz, DMSO-$d_6$): δ 12.91 (s, 1H), 7.98 (s, 2H), 7.58 (s, 1H), 7.43 (d, J=6 Hz, 1H), 7.21 (d, J=6 Hz, 1H), 6.38 (s, 1H), 5.30 (s, 1H), 4.63 (s, 1H), 3.27 (m, 1H), 2.22-1.20 (m, 18H), 0.93 (s, 3H), 0.43 (s, 3H). LCMS m/z 389.48 $[M+H]^+$.

Compound 7:

53% yield. $^1$H NMR (500 MHz, DMSO-d6): δ 12.91 (s, 1H), 7.97 (s, 1H), 7.46 (s, 1H), 7.31 (d, J=6 Hz, 1H), 7.18 (d, J=6 Hz, 1H), 6.39 (s, 1H), 5.30 (s, 1H), 4.63 (s, 1H), 3.27 (m, 1H), 2.22-1.20 (m, 19H), 0.93 (s, 3H), 0.43 (s, 3H). MS m/z 389.48 $[M+H]^+$.

Compound 48:

64% yield. $^1$H NMR (500 MHz, DMSO-$d_6$): δ 9.47 (s, 1H), 8.44 (s, 1H), 8.20 (s, 2H), 8.11 (d, J=6 Hz, 1H), 7.95 (d, J=6 Hz, 1H), 6.40 (s, 1H), 5.30 (s, 1H), 3.29 (m, 1H), 2.97 (t, J=10 Hz, 1H), 2.30-1.96 (m, 5H), 1.85-1.26 (m, 12H), 0.91 (s, 3H), 0.43 (s, 3H). LCMS m/z 400.56 $[M+H]^+$.

Example 2: (3S,8S,9S,10R,13S,14S,17S)-17-(isoquinolin-7-yl)-10,13-dimethyl-2,3,4,7,8,9,10,11,12,13,14,15,16,17-tetradecahydro-1H-cyclopenta[a]phenanthren-3-ol (8a)

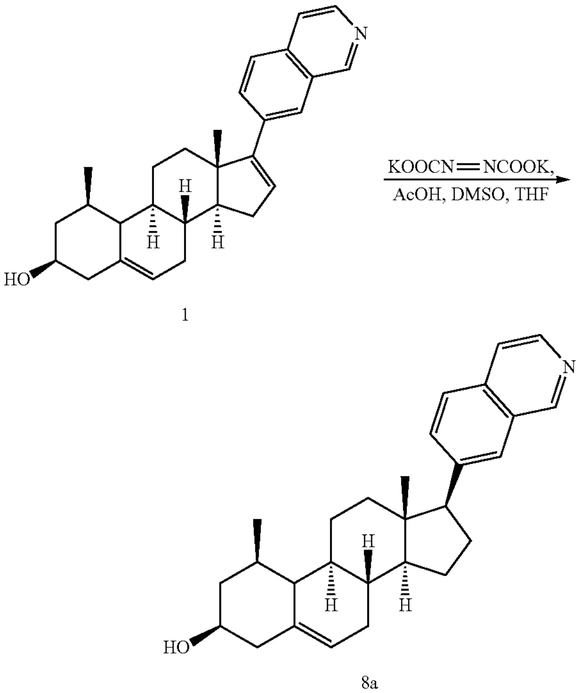

1

8a

To a solution of (3S,8R,9S,10R,13S,14S)-17-(isoquinolin-7-yl)-10,13-dimethyl-2,3,4,7,8,9,10,11,12,13,14,15-dodecahydro-1H-cyclopenta[a]phenanthren-3-ol (1) (10 mg, 0.025 mmol) in DMSO/THF (1:1) (3 mL) was added potassium diazene-1,2-dicarboxylate (109 mg, 0.50 mmol) and AcOH (64 μL, 1 mmol) in 3 portions over 2 hours. The mixture was stirred at rt overnight. An additional 109 mg of diazene-1,2-dicarboxylate and 64 μL of AcOH was added and the mixture stirred 2 h. The mixture was quenched with sat. aq. $NaHCO_3$ and extracted with EtOAc (3×50 mL). The combined organic extracts were washed with $H_2O$, brine, dried over $MgSO_4$, and condensed to give a yellow oil that was purified by reverse phase HPLC using a gradient of 1-80% MeCN in $H_2O$ to give the title compound (8a) as a brown oil (6 mg, 60% yield). $^1$H NMR (500 MHz, DMSO-$d_6$): δ 9.66 (s, 1H), 8.57 (s, 1H), 8.29 (s, 2H), 8.16 (d, J=6 Hz, 1H), 7.99 (d, J=6 Hz, 1H), 5.32 (s, 1H), 3.28 (m, 1H), 2.98 (t, J=10 Hz, 1H), 2.35-1.98 (m, 5H), 1.87-1.29 (m, 14H), 0.93 (s, 3H), 0.46 (s, 3H). MS m/z 402.39 $[M+H]^+$.

Compounds 8b and 9-14 in Table 1 above were prepared by this preceding procedure from Compounds 2-7 and 1, respectively.

Compound 8b:

71% yield. $^1$H NMR (500 MHz, DMSO-d6) δ 9.68 (s, 1H), 8.54 (d, J=5 Hz, 1H), 8.37 (d, J=6 Hz, 1H), 8.31 (s, 1H), 8.19 (d, J=6 Hz, 1H), 8.04 (d, J=6 Hz, 1H), 3.36 (m, 1H), 3.17 (s, 1H), 2.97 (t, J=10 Hz, 1H), 2.41-2.22 (m, 3H), 1.78-1.12 (m, 17H), 0.72 (s, 3H), 0.41 (s, 3H). MS m/z 404.76 $[M+H]^+$.

Compound 9:

64% yield. $^1$H NMR (500 MHz, DMSO-d6) δ 9.86 (s, 1H), 9.80 (s, 1H), 8.28 (s, 1H), 8.24 (d, J=6 Hz, 2H), 5.31 (s, 1H), 4.87 (s, 1H) 3.26 (m, 1H), 3.17 (s, 1H), 2.41-1.87 (m, 6H), 1.83-1.54 (m, 10H), 1.41-1.30 (m, 3H), 1.09 (s, 3H), 0.98 (s, 3H). MS m/z 403.38 $[M+H]^+$.

Compound 10:

52% yield. $^1$H NMR (500 MHz, DMSO-d6) δ 9.36 (s, 1H), 8.14 (br, 2H), 7.91 (s, 1H), 7.86 (d, J=6 Hz, 1H), 7.57 (d, J=6 Hz, 1H), 5.33 (s, 1H), 4.72 (s, 1H), 3.29 (m, 1H), 3.17 (s, 1H),), 2.97 (t, J=10 Hz, 1H), 1.85-1.20 (m, 18H), 0.72 (s, 3H), 0.41 (s, 3H). MS m/z 417.96 $[M+H]^+$.

Compound 11:

48% yield. $^1$H NMR (500 MHz, DMSO-d6): δ 12.96 (s, 1H), 7.94 (s, 1H), 7.48 (s, 1H), 7.40 (d, J=6 Hz, 1H), 7.19 (d, J=6 Hz, 1H), 5.32 (s, 1H), 4.66 (s, 1H), 3.27 (m, 1H), 2.22-1.20 (m, 20H), 0.93 (s, 3H), 0.43 (s, 3H). MS m/z: 405.83 $[M+H]^+$.

Compound 12:

50% yield. $^1$H NMR (500 MHz, DMSO-d6): δ 12.91 (s, 1H), 7.98 (s, 1H), 7.58 (s, 1H), 7.43 (d, J=6 Hz, 1H), 7.21 (d, J=6 Hz, 1H), 5.31 (s, 1H), 4.67 (s, 1H), 3.27 (m, 1H), 2.22-1.20 (m, 20H), 0.92 (s, 3H), 0.44 (s, 3H). MS m/z: 391.28 $[M+H]^+$.

Compound 13:

53% yield. $^1$H NMR (500 MHz, DMSO-d6): δ 12.91 (s, 1H), 7.97 (s, 1H), 7.46 (s, 1H), 7.31 (d, J=6 Hz, 1H), 7.18 (d, J=6 Hz, 1H), 5.32 (s, 1H), 4.63 (s, 1H), 3.27 (m, 1H), 2.22-1.20 (m, 20H), 0.91 (s, 3H), 0.46 (s, 3H). MS m/z: 391.34 $[M+H]^+$.

Compound 14:

68% yield. $^1$H NMR (500 MHz, DMSO-d6): δ 9.36 (s, 1H), 8.14 (br, 2H), 7.91 (s, 1H), 7.86 (d, J=6 Hz, 1H), 7.57 (d, J=6 Hz, 1H), 5.33 (s, 1H), 3.29 (m, 1H), 3.17 (s, 1H),), 2.98 (t, J=10 Hz, 1H), 1.85-1.20 (m, 19H), 0.72 (s, 3H), 0.41 (s, 3H). MS m/z: 402.83 $[M+H]^+$.

Example 3: (3S,8R,9S,10S,13S,14S)-17-(isoquinolin-7-yl)-N,N,10,13-tetramethyl-2,3,4,5,6,7,8,9,10,11,12,13,14,15-tetradecahydro-1H-cyclopenta[a]phenanthren-3-amine (22r)

Compound 22r was prepared according to literature procedure. Czakó, *J. Am. Chem. Soc.* 2009, 131, 9014-9019.

To a solution of (3S,8R,9S,10S,13S,14S)-3-(dimethylamino)-10,13-dimethyl-2,3,4,5,6,7,8,9,10,11,12,13,14,15-tetradecahydro-1H-cyclopenta[a]phenanthren-17-yl trifluoromethanesulfonate (100 mg, 0.22 mmol) in 1,4-dioxane (5 mL) and 2M aq. $Na_2CO_3$ (0.55 mL, 1.1 mmol) was added isoquinolin-7-yl boronic acid (46 mg, 0.27 mmol). The mixture was thoroughly degassed and $Pd(PPh_3)_2Cl_2$ (8 mg, 0.011 mmol) was added. The mixture was stirred at 90° C. for 1 hour. The reaction was quenched with $H_2O$ and extracted with EtOAc (3×50 mL). The combined organic extracts were washed with $H_2O$, brine, dried over $MgSO_4$, and condensed to give a yellow oil that was purified by reverse phase HPLC using a gradient of 1-70% MeCN in $H_2O$ to give the title compound as a brown oil (38 mg, 40% yield). MS m/z 429.39 $[M+H]^+$.

Example 4: (3S,8R,9S,10S,13S,14S,17S)-(isoquinolin-7-yl)-N,N,10,13-tetramethylhexadecahydro-1H-cyclopenta[a]phenanthren-3-amine (23)

Scheme 3.

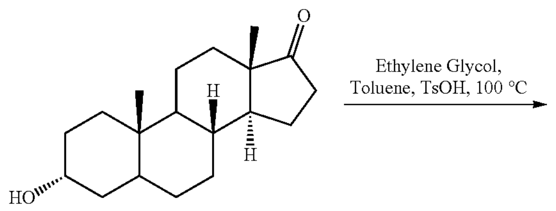

15

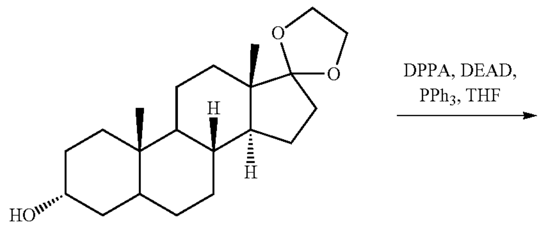

16

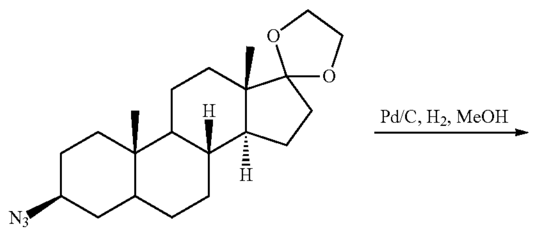

17

-continued

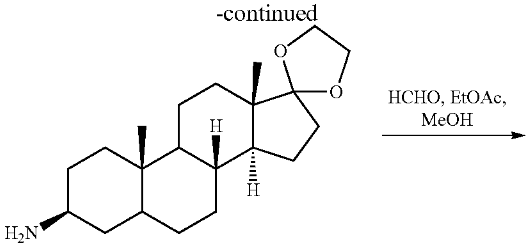

18

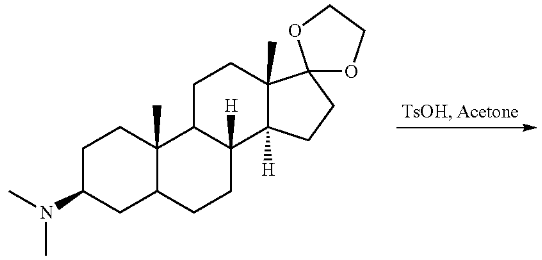

19

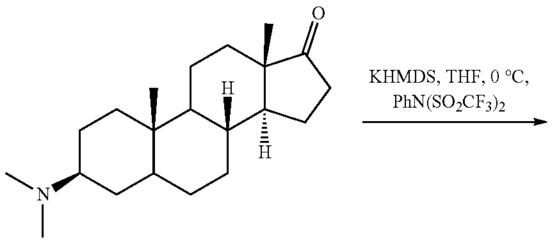

20

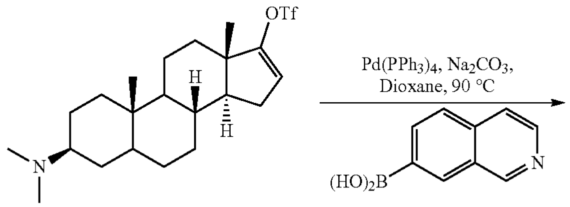

21

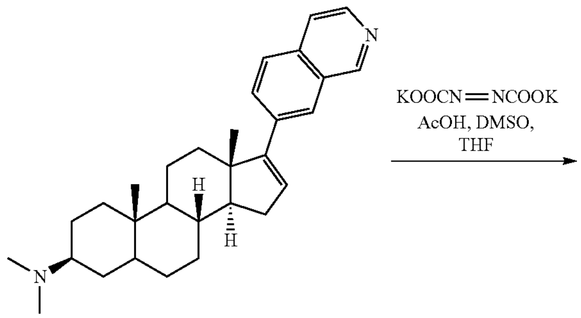

22r

-continued

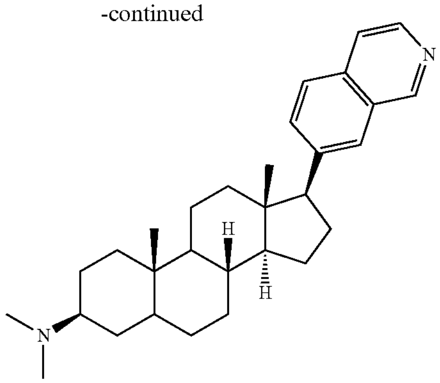

23

Compound 22r was prepared according to literature procedure. Czakó B., et al., *J. Am. Chem. Soc.* 2009, 131, 9014-9019. Compound 23 was prepared from compound 22r according to the reductive diimide procedure described above in the preparation of compound 8a. MS m/z 431.31 $[M+H]^+$.

Compounds 24 and 25 in Table 1 above were prepared in a similar manner as Compounds 22r and 23, respectively.

Compound 24: LCMS m/z 429.47 $[M+H]^+$.

Compound 25: LCMS m/z 431.82 $[M+H]^+$.

Example 5: (3S,8R,9S,10R,13S,14S)-17-(isoquinolin-7-yl)-N,N,10,13-tetramethyl-2,3,4,7,8,9,10,11,12,13,14,15,16,17-tetradecahydro-1H-cyclopenta[a]phenanthren-3-amine (33)

Scheme 4

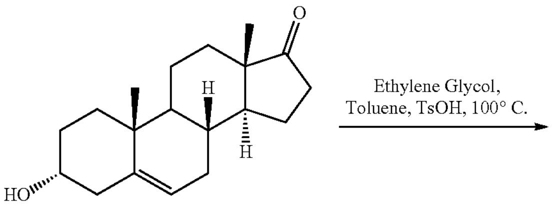

26

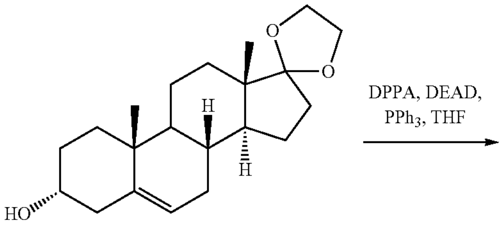

27

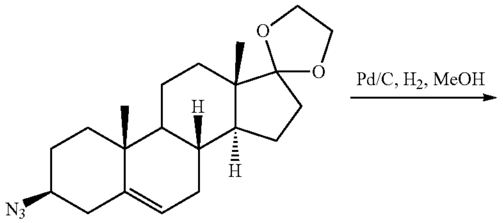

28

-continued

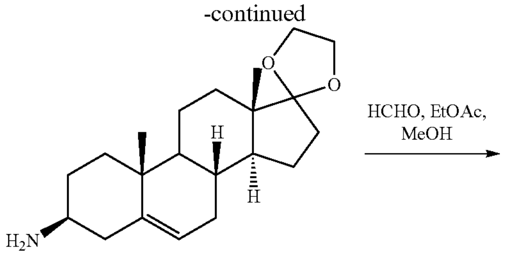

29a

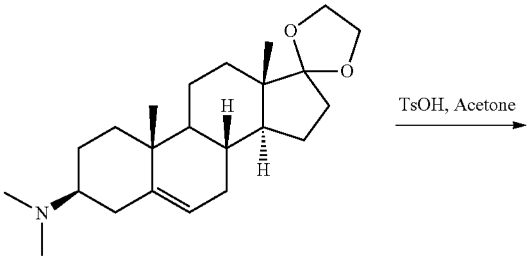

29b

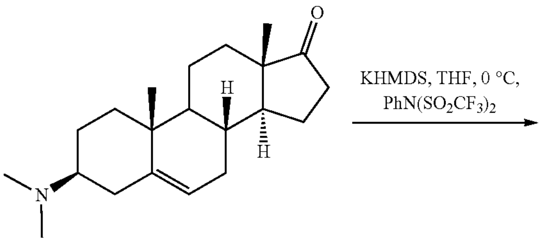

30

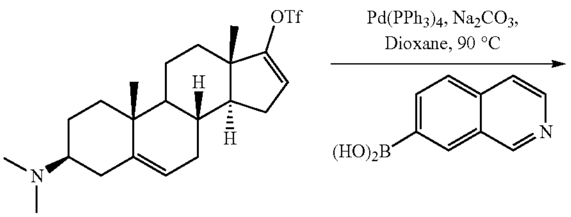

31

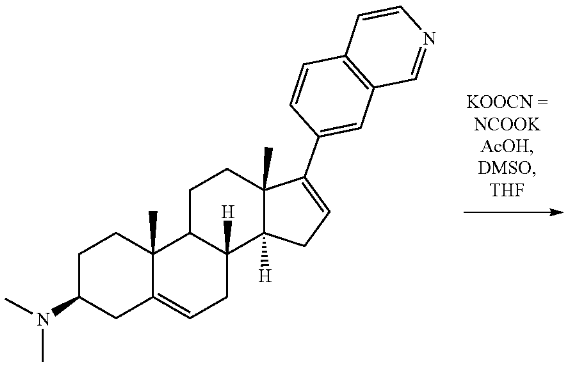

32

-continued

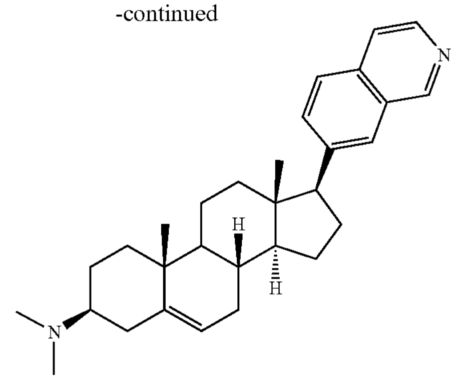

33

Step 1: Synthesis of Intermediates 26-28

Intermediates 26-28 were prepared in a similar manner according to literature procedure, beginning with cis-dehydroepiadrosterone, as shown in Scheme 4. Czakó, B., et al. *J. Am. Chem. Soc.* 2009, 131, 9014-9019. Intermediate 29a was prepared as shown in Scheme 3.

Step 2: Synthesis of Intermediate 29a

Scheme 5.

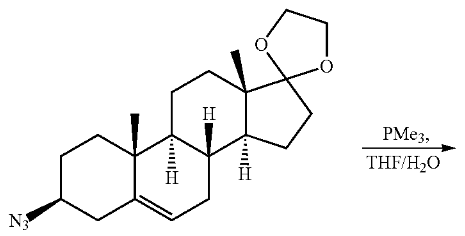

28

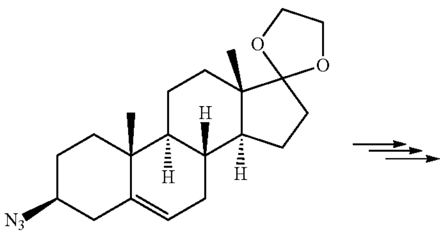

29a

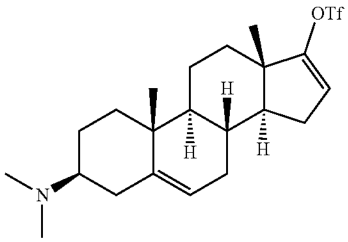

31

(3S,8R,9S,10R,13S,14S)-3-azido-10,13-dimethyl-1,2,3,4,7,8,9,10,11,12,13,14,15,16-tetradecahydrospiro[cyclopenta[a]phenanthrene-17,2'-[1,3]dioxolane](28) (2-g, 5.59 mmol) was dissolved in anhydrous THF (50 mL). $H_2O$ (503 µL, 28 mmol) was added after $PMe_3$ (1.15 mL, 11.2 mmol) was added. The mixture was stirred for 6 h. The reaction was quenched with $H_2O$ and extracted with EtOAc (3×50 mL). The combined organic extracts were washed with $H_2O$, brine, dried over $MgSO_4$, and condensed to give a yellow oil that was purified by flash chromatography using a gradient of 1-10% MeOH in DCM to give intermediate. 29a as a white solid (1.58 g, 85% yield). $^1$H NMR (500 MHz, $CDCl_3$): δ 5.39 (s, 1H), 3.97-3.86 (m, 4H), 3.47 (br, 2H), 2.81 (m, 4H), 2.28 (m, 1H), 2.05-1.98 (m, 2H), 1.92-1.78 (m, 3H), 1.74-1.67 (m, 1H), 1.64-1.38 (m, 9H), 1.32-1.24 (m, 1H), 1.15-1.07 (m, 1H), 1.03 (s, 3H), 0.88 (s, 3H). MS m/z 332.47 $[M+H]^+$.

Steps 3 and 4: Synthesis of Compounds 32 and 33 Compounds 32 and 33 were prepared from intermediate 29a, as shown above in Scheme 4.

Compound 32:

$^1$H NMR (500 MHz, DMSO-d6): δ 9.65 (s, 1H), 8.57 (d, J=6 Hz, 1H), 8.33 (s, 1H), 8.17 (d, J=6 Hz, 1H), 8.12 (s, 2H), 6.39 (s, 1H), 5.49 (s, 1H), 3.17 (s, 1H), 3.04 (m, 4H), 2.78 (s, 6H), 2.45-2.26 (m, 5H), 1.98-1.88 (m, 3H), 1.81-1.55 (m, 6H), 1.49-1.41 (m, 1H), 1.17 (s, 3H), 1.06 (s, 3H). MS m/z: 427.29 $[M+H]^+$.

Compound 33:

$^1$H NMR (500 MHz, DMSO-d6): δ 9.72 (s, 1H), 8.61 (d, J=6 Hz, 1H), 8.35 (d, J=6 Hz, 1H), 8.33 (s, 1H), 8.20 (d, J=6 Hz, 1H), 8.03 (d, J=6 Hz, 1H), 5.47 (s, 1H), 3.44 (m, 1H), 3.0 (t, J=10 Hz, 1H), 2.77 (s, 6H), 2.44-2.27 (m, 5H), 1.68-1.28 (m, 12H), 1.16-1.00 (m, 4H), 0.96 (s, 3H), 0.47 (s, 3H). MS m/z: 429.58 $[M+H]^+$.

Example 6: 4-((3S,5S,8R,10S,13S,14S,17S)-17-(isoquinolin-7-yl)-10,13-dimethylhexadecahydro-1H-cyclopenta[a]phenanthren-3-yl)morpholine (34)

Compound 34 was prepared in an analogous manner as demonstrated in Czakó, B., et al. *J. Am. Chem. Soc.* 2009, 131, 9014-9019, i.e., the unsaturated equivalent of intermediate 29a was treated with 2-bromoethyl ether and $NaHCO_3$ in toluene to the corresponding morpholine compound; the ketal was removed with para-toluene sulfonic acid (PTSA) in acetone and the resulting ketone was converted to the vinyl triflate with potassium hexamethyldisilazide (KHMDS) and $PhN(SO_2CF_3)_2$ in THF. The vinyl triflate was subsequently coupled with isoquinoline boronic acid under the Suzuki conditions described throughout.

Example 7: 7-((3S,8R,9S,10S,13S,14S,17S)-10,13-dimethyl-3-(1H-1,2,3-triazol-1-yl)hexadecahydro-1H-cyclopenta[a]phenanthren-17-yl)isoquinoline (39)

Scheme 6.

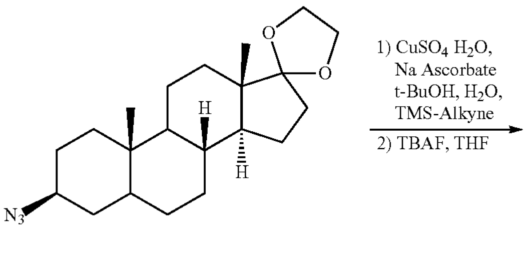

-continued

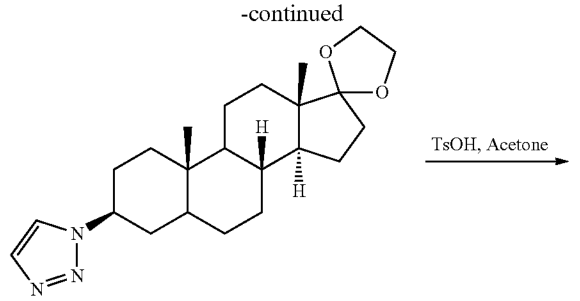

35

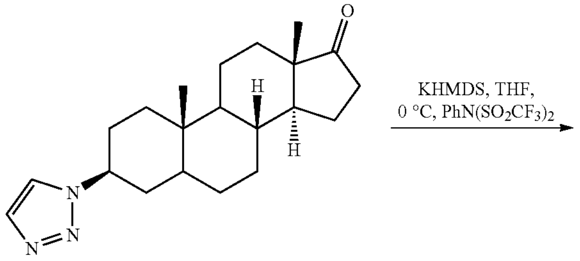

36

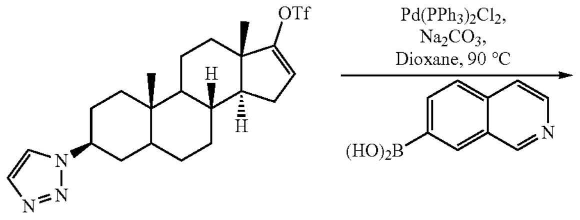

37

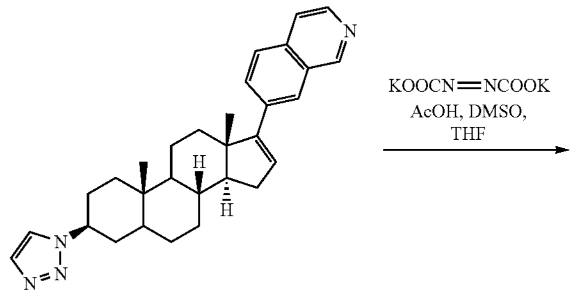

38

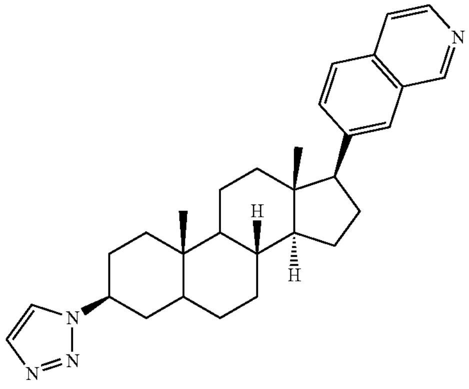

39

Step 1: Synthesis of Intermediate 35

To a solution of (3S,8R,9S,10S,13S,14S)-3-azido-10,13-dimethylhexadecahydrospiro-[cyclopenta[a]phenanthrene-17,2'-[1,3]dioxolane](500 mg, 1.39 mmol) in t-BuOH (10 mL) and $H_2O$ (3 mL) was added $CuSO_4 \cdot 5H_2O$ (18 mg, 0.07 mmol) and sodium ascorbate (6 mg, 0.03 mmol) followed by TMS-acetylene (231 μL, 1.67 mmol). The reaction mixture was heated to 70° C. for 1 h. The reaction was quenched with $H_2O$ and extracted with EtOAc (3×50 mL). The combined organic, extracts were washed with $H_2O$, brine, dried over $MgSO_4$, and condensed to give a yellow oil that was dissolved in THF (20 mL). TBAF 1M in THF (6.95 mL, 6.95 mmol) was added and stirred for 30 minutes. The reaction was quenched with $H_2O$ and extracted with EtOAc (3×50 mL). The combined organic extracts were washed with $H_2O$, brine, dried over $MgSO_4$, and condensed to give a brown oil that was purified by flash chromatography using a gradient of 10-60% EtOAc in hexanes to give intermediate 35 as a white solid (348 mg, 65% yield). $^1H$ NMR (500 MHz, $CDCl_3$): δ 8.01 (q, J=10 Hz, 2H), 4.31 (m, 1H), 3.95-3.82 (m, 4H), 2.83 (m, 3H), 2.27 (m, 1H), 2.03-1.95 (m, 2H), 1.90-1.75 (m, 3H), 1.71-1.63 (m, 1H), 1.67-1.39 (m, 10H), 1.35-1.26 (m, 1H), 1.13-1.07 (m, 1H), 0.97 (s, 3H), 0.78 (s, 3H). MS m/z 386.76 $[M+H]^+$.

Steps 2 and 3: Synthesis of Intermediates 36 and 37

Intermediate 36 (MS m/z 341.86 $[M+H]^+$) was prepared using the procedure used to prepare intermediates 20 and 30 above. Intermediate 37 (MS m/z 474.45 $[M+H]^+$) was prepared using the procedure used to prepare intermediates 21 and 31 above.

Step 4: Synthesis of Compound 38

Compound 38 was prepared from intermediate 37 using the procedure used to prepare compound 1 above. $^1H$ NMR (500 MHz, DMSO-$d_6$): δ 9.74 (s, 1H), 8.53 (d, J=6 Hz, 1H), 8.17 (s, 2H), 8.03 (q, J=10 Hz, 2H), 7.90 (s, 1H), 7.69 (s, 1H), 6.38 (s, 1H), 4.52 (m, 1H), 2.33-2.11 (m, 3H), 2.12-1.85 (m, 5H), 1.72-1.40 (m, 8H), 1.30-1.20 (m, 2H), 1.15-1.08 (m, 1H), 0.97 (s, 3H), 0.92-0.87 (m, 1H), 0.51 (s, 3H). MS m/z 453.51 $[M+H]^+$.

Step 5: Synthesis of Compound 39

Compound 39 was prepared from compound 38 using the procedure used to prepare compounds 8a. $^1H$ NMR (500 MHz, DMSO-$d_6$): δ 9.76 (s, 1H), 8.57 (d, J=6 Hz, 1H), 8.21 (s, 2H), 8.06 (q, J=10 Hz, 2H), 7.92 (s, 1H), 7.72 (s, 1H), 4.58 (m, 1H), 3.02 (t, J=10 Hz, 1H), 2.33-2.11 (m, 3H), 2.06-1.82 (m, 5H), 1.69-1.37 (m, 10H), 1.33-1.22 (m, 2H), 1.13-1.04 (m, 1H), 0.95 (s, 3H), 0.92-0.87 (m, 1H), 0.53 (s, 3H). MS m/z 455.68 $[M+H]^+$.

Example 8: (3S,8R,9S,10S,13S,14S,17S)-17-(isoquinolin-7-yl)-N,10,13-trimethylhexadecahydro-1H-cyclopenta[a]phenanthren-3-amine (46)

Scheme 7.

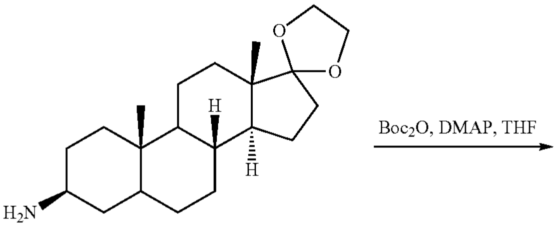

-continued

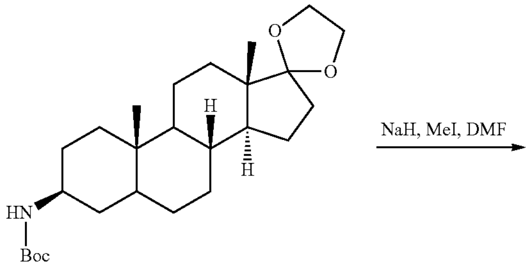

40

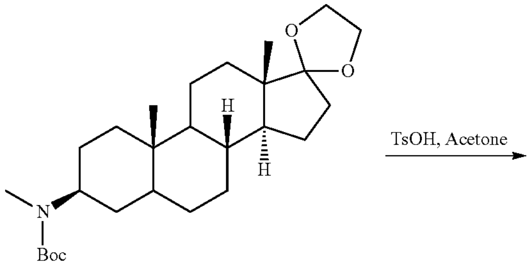

41

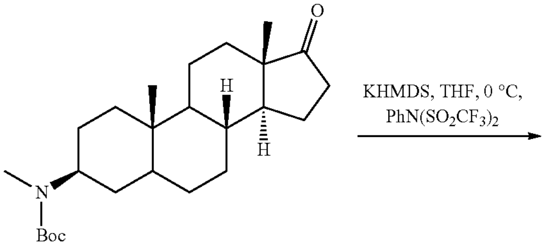

42

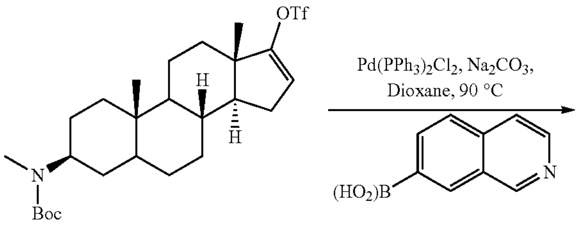

43

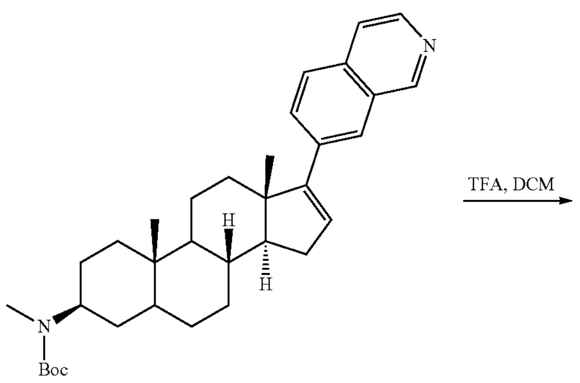

44

-continued

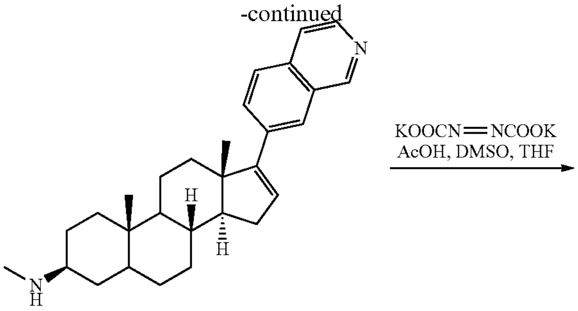

45

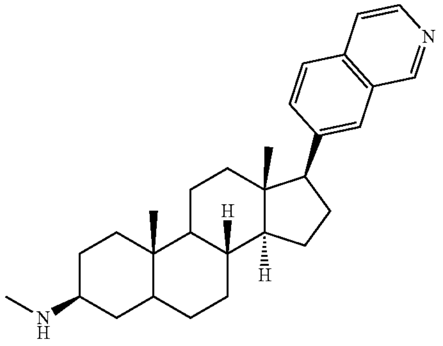

46

Step 1: Synthesis of Intermediate 40

To a solution of (3S,8R,9S,10S,13S,14S)-10,13-dimethylhexadecahydrospiro-[cyclopenta[a]phenanthrene-17,2'-[1,3]dioxolan]-3-amine (500 mg, 1.50 mmol) in THF (25 mL) was added $Boc_2O$ (393 mg, 1.80 mmol) followed by DMAP (37 mg, 0.3 mmol). The mixture was stirred for 3 h. The reaction was quenched with $H_2O$ and extracted with EtOAc (3×50 mL). The combined organic extracts were washed with $H_2O$, brine, dried over $MgSO_4$, and condensed to give a yellow oil that was purified by flash chromatography using a gradient of 5-20% EtOAc in Hexanes to give intermediate 40 as a white solid (602 mg, 93% yield). $^1H$ NMR (500 MHz, $CDCl_3$): δ 6.42 (br, 1H), 3.92-3.81 (m, 4H), 2.06-1.89 (m, 1H), 1.80-1.52 (m, 10H), 1.46 (s, 9H), 1.41-1.18 (m, 10H), 1.08-0.90 (m, 2H), 0.81 (s, 3H), 0.79 (s, 3H). MS m/z 434.58 $[M+H]^+$.

Step 2: Synthesis of Intermediate 41

To a solution of tert-butyl ((3S,8R,9S,10S,13S,14S)-10,13-dimethylhexadecahydrospiro[cyclopenta[a]phenanthrene-17,2'-[1,3]dioxolan]-3-yl)carbamate (602 mg, 1.39 mmol) in DMF (10 mL) was added NaH 60% in mineral oil (83 mg, 2.08 mmol). The mixture was stirred for 30 minutes, then MeI (208 μL, 3.34 mmol) was added and stirred overnight. The reaction was quenched with $H_2O$ and extracted with EtOAc (3×50 mL). The combined organic extracts were washed with $H_2O$, brine, dried over $MgSO_4$, and condensed to give a yellow oil that was purified by flash chromatography using a gradient of 5-30% EtOAc in Hexanes to give intermediate 41 as a white solid (602 mg, 93% yield). $^1H$ NMR (500 MHz, $CDCl_3$): δ 3.95-3.82 (m, 4H), 2.75 (s, 3H), 2.02-1.93 (m, 1H), 1.84-1.50 (m, 10H), 1.48 (s, 9H), 1.45-1.18 (m, 10H), 1.10-0.90 (m, 2H), 0.86 (s, 3H), 0.82 (s, 3H). MS m/z 448.83 $[M+H]^+$.

Steps 3 and 4: Synthesis of Intermediates 42 and 43

Intermediate 42 (MS m/z 404.31 $[M+H]^+$) was prepared from intermediate 41 using the procedure used to prepare intermediates 20 and 30 above. Intermediate 43 (MS m/z 536.78 $[M+H]^+$) was prepared from intermediate 42 using the procedure used to prepare intermediates 21 and 31 above.

Step 5: Synthesis of Intermediate 44

Intermediate 44 was prepared from intermediate 43 using the procedure used to prepare Compound 1 above. $^1H$ NMR (500 MHz, DMSO-$d_6$): δ 9.70 (s, 1H), 8.50 (d, J=6 Hz, 1H), 8.25 (s, 1H), 8.19 (d, J=6 Hz, 1H), 8.14 (d, J=6 Hz, 1H), 8.04 (d, J=8 Hz, 1H), 6.32 s, 1H), 2.77 (s, 3H), 2.40-2.33 (m, 1H), 2.21-2.10 (m, 2H), 1.82-1.59 (m, 8H), 1.49 (s, 9H), 1.44-1.24 (m, 8H), 1.15 (s, 3H), 1.12-1.05 (m, 2H), 0.90 (s, 3H). MS m/z 515.63 $[M+H]^+$.

Step 6: Synthesis of Compound 45

To a solution of tert-butyl ((3S,8R,9S,10S,13S,14S)-17-(isoquinolin-7-yl)-10,13-dimethyl-2,3,4,5,6,7,8,9,10,11,12,13,14,15-tetradecahydro-1H-cyclopenta[a]phenanthren-3-yl)(methyl)carbamate (50 mg, 0.1 mmol) in DCM (10 mL) was added TFA (1 mL). The mixture was stirred for 30 min and the solvent removed in vacuo to give compound 45 as a beige solid that was used without further purification (40 mg, 98% yield). MS m/z 415.57 $[M+H]^+$.

Step 7: Synthesis of Compound 46

Compound 46 was prepared from compound 45 using the procedure used to prepare compound 8a above. 91% yield. MS m/z 417.37 $[M+H]^+$.

Example 9: N-((3S,8R,10S,13S,14S,17S)-17-(isoquinolin-7-yl)-10,13-dimethylhexadecahydro-1H-cyclopenta[a]phenanthren-3-yl)-N-methylacetamide (47)

Scheme 8.

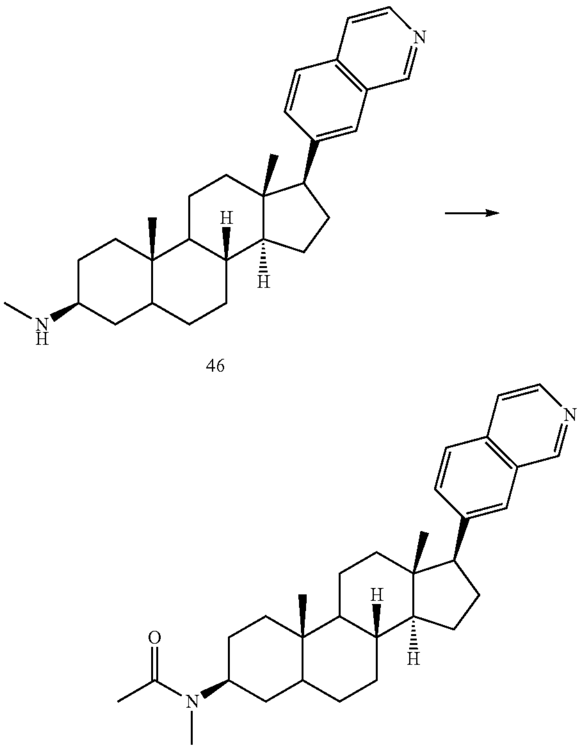

46

47

To a solution of (3S,8R,10S,13S,14S,17S)-17-(isoquinolin-7-yl)-N,10,13-trimethylhexadecahydro-1H-cyclopenta[a]phenanthren-3-amine 46 (20 mg, 0.048 mmol) in THE (3 mL) and sat. aq. $NaHCO_3$ solution (2 mL) was added acetyl chloride (4 μL, 0.058 mmol). The mixture was stirred for 30 minutes and then the reaction was quenched with $H_2O$ and extracted with EtOAc (3x50 mL). The combined organic extracts were washed with $H_2O$, brine, dried over $MgSO_4$ and condensed to give a yellow oil that was purified by reverse phase HPLC using a gradient of 1-80% MeCN in H2O to give the title compound 47 as a brown solid (12 mg, 57% yield). $^1H$ NMR (500 MHz DMSO-$d_6$): δ 9.70 (s, 1H), 8.62 (d, J=6 Hz, 1H), 8.33 (d, J=6 Hz, 1H), 8.31 (s, 1H), 8.22 (d, J=6 Hz, 1H), 8.01 (d, J=6 Hz, 1H), 3.54 (m, 1H), 3.21 (s, 3H), 3.1 (t, J=10 Hz, 1H), 2.70 (s, 3H), 2.44-2.27 (m, 6H), 1.68-1.28 (m, 12H), 1.16-1.00 (m, 4H), 0.94 (s, 3H), 0.44 (s, 3H). MS m/z: 459.72 $[M+H]^+$.

Example 10: Biological Activities of the Compounds of the Application

Compounds of the present application were tested in a competitive kinase binding assay by using commercially available assay system. For example, LANTHASCREEN© Eu Kinase Binding Assay (INVITROGEN™) was used to measure the $IC_{50}$ of the compounds of the present application in displacing the Tracer from binding to the target kinase, by following the assay protocol from INVITROGEN™.

Biological activities of the compounds of the application are shown in Table 2 below and FIG. 1.

TABLE 2

| Compound No. | Enzyme $IC_{50}$ (nM) | Compound No. | Enzyme $IC_{50}$ (nM) | Compound No. | Enzyme $IC_{50}$ (nM) |
|---|---|---|---|---|---|
| 1 | B | 2 | E | 3 | G |
| 4 | F | 5 | E | 6 | G |
| 7 | G | 8a | A | 8b | C |
| 9 | G | 10 | B | 11 | D |
| 12 | G | 13 | G | 14 | F |
| 22r | B | 23 | A | 24 | C |
| 25 | A | 32 | B | 33 | A |
| 34 | B | 39 | A | 46 | E |
| 47 | A | 48 | G | | |

$IC_{50}$ ratings: "A" ≤100 nM; "B" = 101-200 nM; "C" = 201-300 nM; "D" = 301-700 nM; "E" = 701-2,000 nM; "F" = 2,001-6,000 nM; "G" ≥ 6,001 nM.

Example 11: KINOMESCAN® of a Compound of the Application

Figure 2:
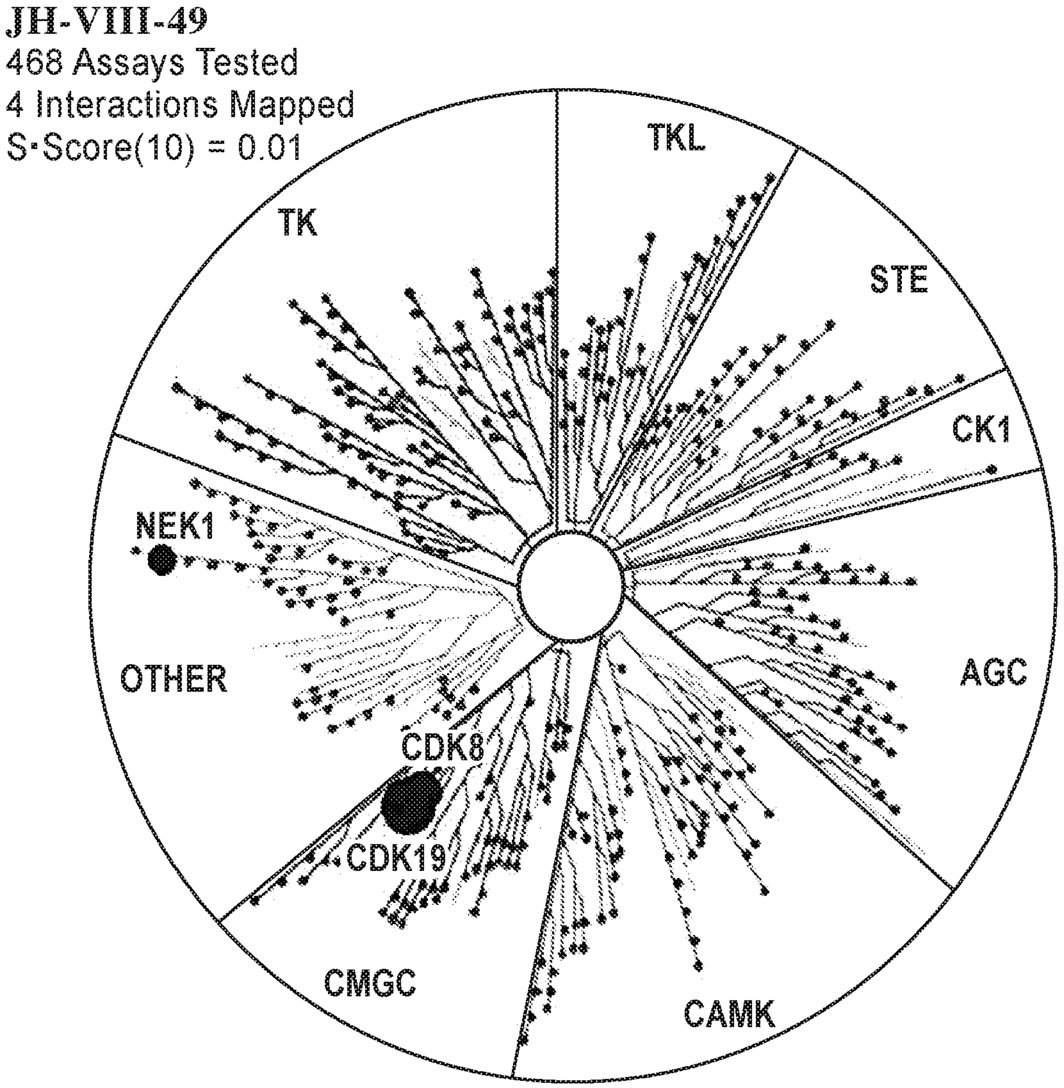
FIG. 2 is a KINOMESCAN® showing that Compound 33 is highly selective for CDK8 and CDK19. The KINOMESCAN® was performed with binding assays of Compound 33 against a panel of 468 kinases at a concentration of 10 μM.

To evaluate the kinase selectivity of compounds of the application, KINOMESCAN® binding analysis against a panel of 468 kinases at a concentration of 10 μM was conducted. The profiling revealed an extremely high level of selectivity for Compound 33 with only 4 interactions greater than 90% inhibition including CDK19, CDK8, NEK1 and PIKFYVE (FIG. 2). Dose-response analysis revealed no inhibition of NEK1 with an $IC_{50}$>10,000 nM.

EQUIVALENTS

Those skilled in the art will recognize, or be able to ascertain using no more than routine experimentation, many equivalents to the specific embodiments and methods described herein. Such equivalents are intended to be encompassed by the scope of the present application.

All patents, patent applications, and literature references cited herein are hereby expressly incorporated by reference.

The invention claimed is:

1. A compound represented by Formula (I):

(I)

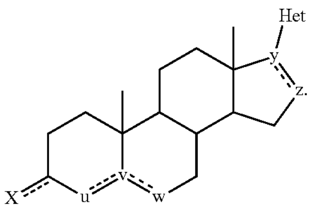

or a stereoisomer or pharmaceutically acceptable salt thereof, wherein:

X is —OR, or —$NR_1R_2$;

R is H or $C_1$-$C_6$ alkyl;

$R_1$ and $R_2$ are each independently H, $C_1$-$C_6$ alkyl, —C(O)—$C_1$-$C_6$ alkyl, or $R_1$ and $R_2$, together with the nitrogen atom to which they are attached, form a 3- to 7-membered heterocyclic or a 5-, 8-, or 9-membered heteroaryl ring optionally comprising one or more additional heteroatoms selected from nitrogen, sulfur, and oxygen;

u, v, and w together form (i):

(i)

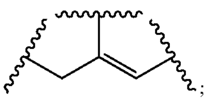

y and z together form (iv) or (v):

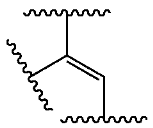

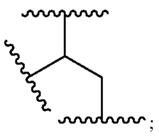

Het is

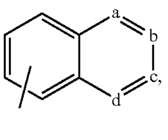

wherein a is $CR_3$; b, c, and d are each independently $CR_3$ or N, provided that at most two of b, c, and d are N; and each $R_3$ is independently H or $NH_2$, provided that Het is not quinolinyl; or Het is

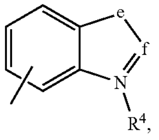

wherein $R_4$ is H or $C_1$-$C_6$ alkyl; e is $CR_5$; f is N; and $R_5$ is H or $NH_2$.

2. The compound of claim 1, wherein y and z together form

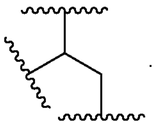 [SMILES: *CC(*)*]

3. The compound of claim 1, wherein X is —OR and R is H or $C_1$-$C_6$ straight-chain or $C_3$-$C_6$ branched alkyl optionally substituted with OH, O—($C_1$-$C_6$ alkyl), $NH_2$, NH($C_1$-$C_6$ alkyl), or N($C_1$-$C_6$ alkyl)$_2$.

4. The compound of claim 1, wherein X is —$NR_1R_2$.

5. The compound of claim 4, wherein $R_1$ and $R_2$ are each $C_1$-$C_6$ straight-chain or $C_3$-$C_6$ branched alkyl, or wherein $R_1$ and $R_2$, together with the nitrogen atom to which they are attached, form triazole, morpholine, or pyrrolidine.

6. The compound of claim 1, wherein X is =O.

7. The compound of claim 1, wherein Het is 6-isoquinolinyl, 7-isoquinolinyl, 6-quinazolinyl, 6-phthalazinyl, 6-indazolyl, 6-indazolyl-3-amine, or 5-indazolyl.

8. The compound of claim 7, wherein Het is 7-isoquinolinyl.

9. The compound of claim 1, of Formula (iv(a)'), (v(a)'), (iv(a)"), or (v(a)"):

(iv(a)')

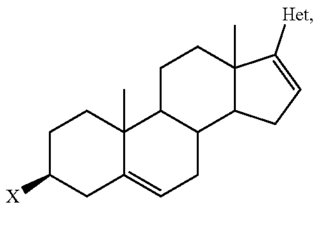

(v(a)')

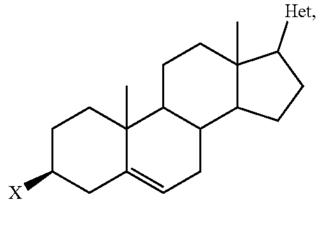

-continued (iv(a)″)

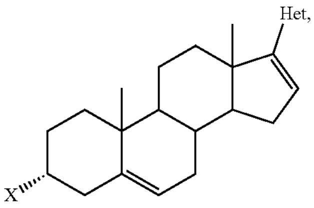

or (v(a)″)

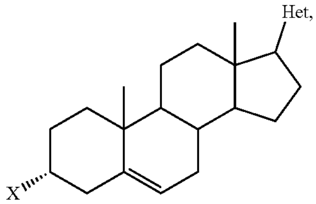

wherein:

X is —OR or —$NR_1R_2$;

R is H or $C_1$-$C_6$ alkyl; and $R_1$ and $R_2$ are each independently H, $C_1$-$C_6$ alkyl, or —C(O)—$C_1$-$C_6$ alkyl, or $R_1$ and $R_2$, together with the nitrogen atom to which they are attached, form a 3- to 7-membered heterocyclic or a 5-, 8-, or 9-membered heteroaryl ring optionally comprising one or more additional heteroatoms selected from nitrogen, sulfur, and oxygen.

10. The compound of claim 1, having a structure of one of the following formulae:

IIb

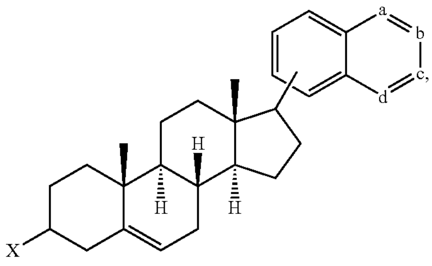

or

IId

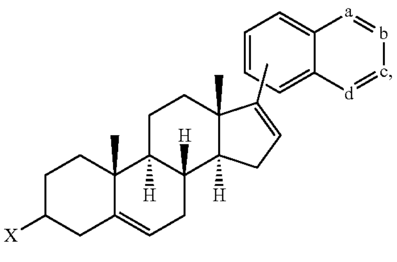

wherein:

X is —OH or —$NR_1R_2$;

$R_1$ and $R_2$ are each independently H, $C_1$-$C_6$ alkyl, or —C(O)—$C_1$-$C_6$ alkyl, or $R_1$ and $R_2$, together with the nitrogen atom to which they are attached, form a 3- to 7-membered heterocyclic or a 5-, 8-, or 9-membered heteroaryl ring optionally comprising one or more additional heteroatoms selected from nitrogen, sulfur, and oxygen;

a, b, c, and d are each independently $CR_3$ or N; and each $R_3$ is independently H or $NH_2$.

11. The compound of claim 1, having a structure of one of the following formulae:

IIIb

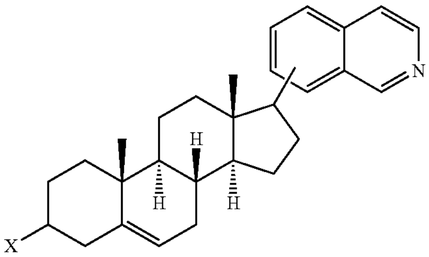

or

IIId

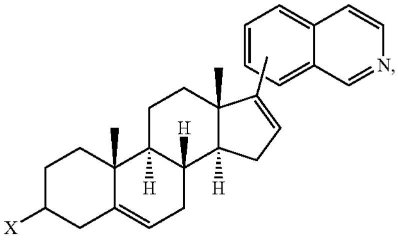

wherein:

X is —OH or —$NR_1R_2$; and $R_1$ and $R_2$ are each independently H, $C_1$-$C_6$ alkyl, or —C(O)—$C_1$-$C_6$ alkyl, or $R_1$ and $R_2$, together with the nitrogen atom to which they are attached, form a 3- to 7-membered heterocyclic or a 5-, 8-, or 9-membered heteroaryl ring optionally comprising one or more additional heteroatoms selected from nitrogen, sulfur, and oxygen.

12. The compound of claim 1, having a structure of one of the following formulae:

IVb

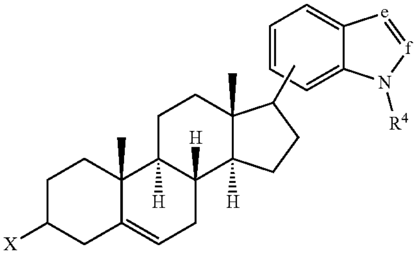

or

IVd

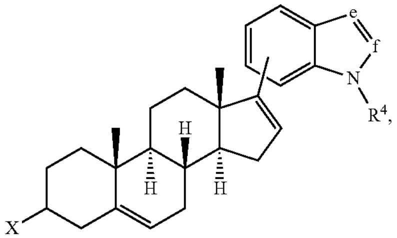

wherein:

X is —OH or —$NR_1R_2$;

$R_1$ and $R_2$ are each independently H, $C_1$-$C_6$ alkyl, —C(O)—$C_1$-$C_6$ alkyl, or $R_1$ and $R_2$, together with the nitrogen atom to which they are attached, form a 3- to 7-membered heterocyclic or a 5-, 8-, or 9-membered heteroaryl ring optionally comprising one or more additional heteroatoms selected from nitrogen, sulfur, and oxygen;
$R_4$ is H or $C_1$-$C_6$ alkyl;
e and f are each independently $CR_5$ or N; and
each $R_5$ is independently H or $NH_2$.
13. A compound which is:
(1)
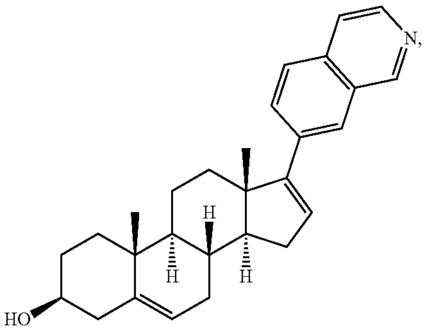
(2)
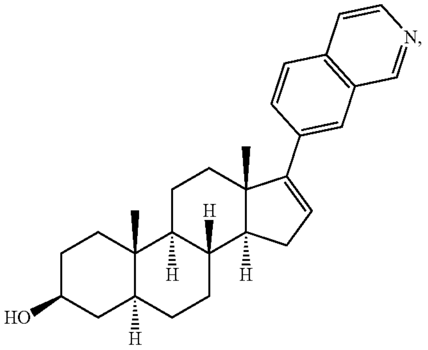
(3)
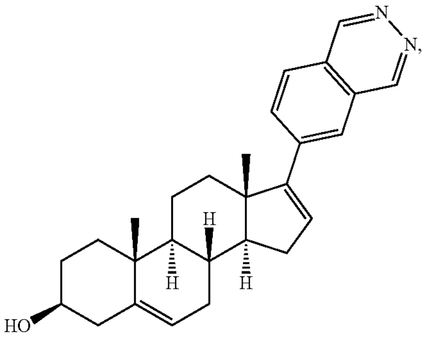
(4)
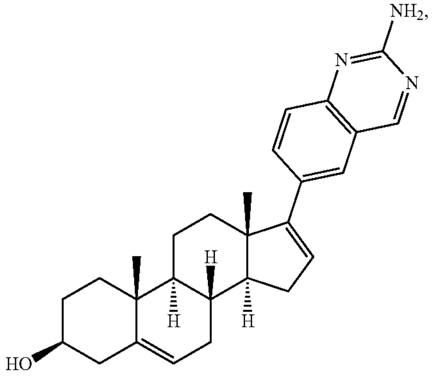
-continued
(5)
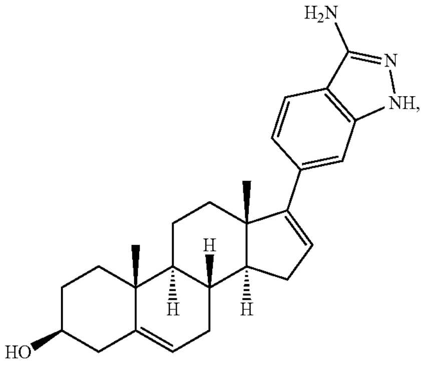
(6)
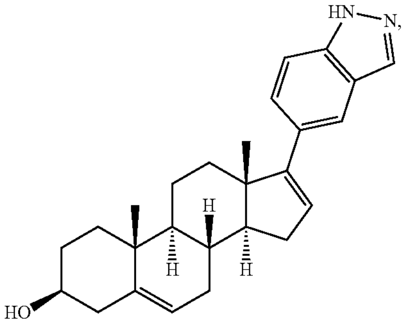
(7)
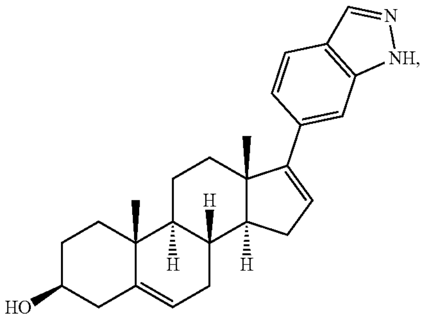
(8a)
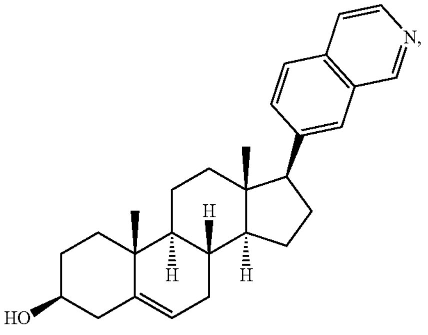

-continued
(8b)
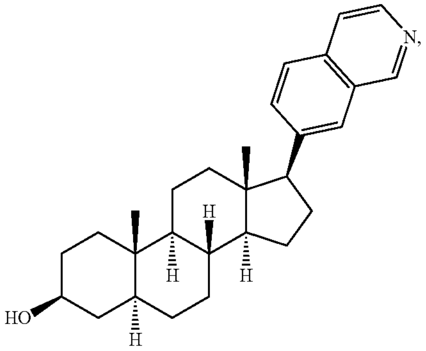
(9)
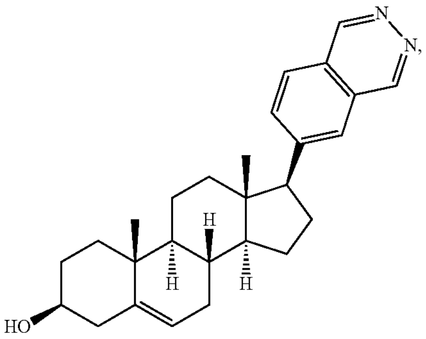
(10)
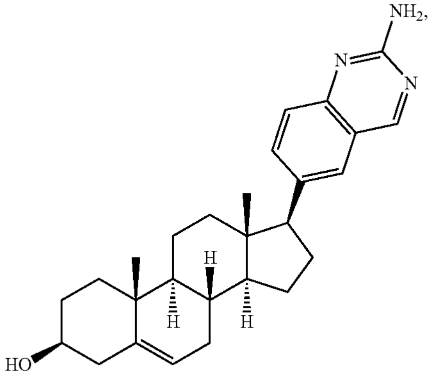
(11)
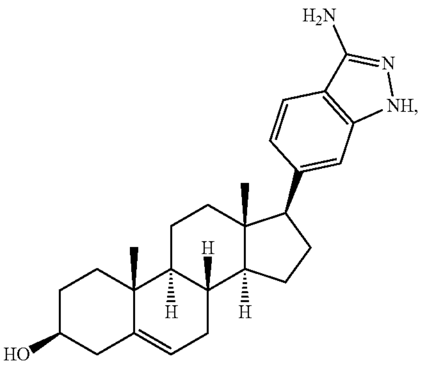
-continued
(12)
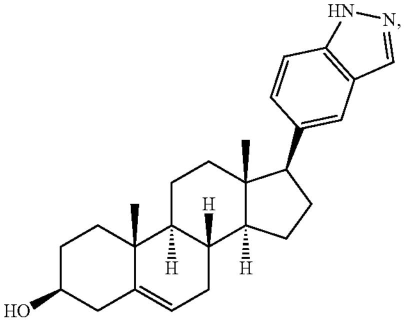
(13)
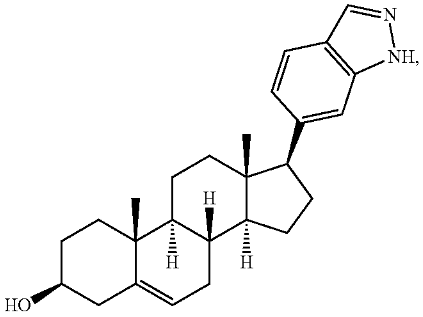
(14)
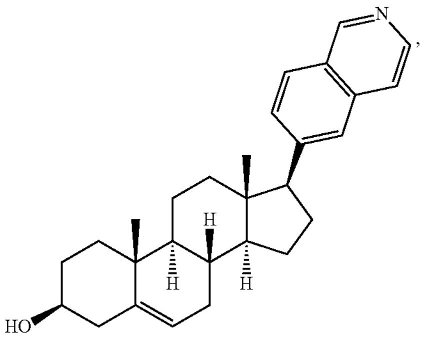
(32)
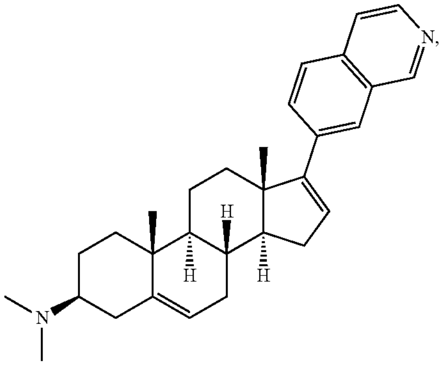

-continued (33)

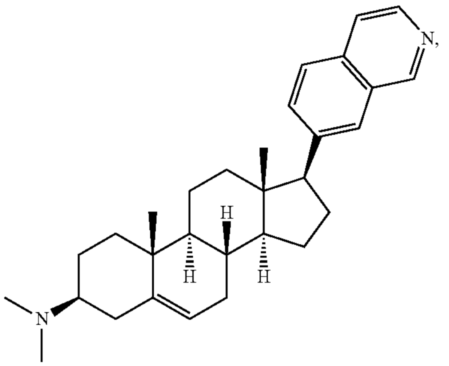

or (48)

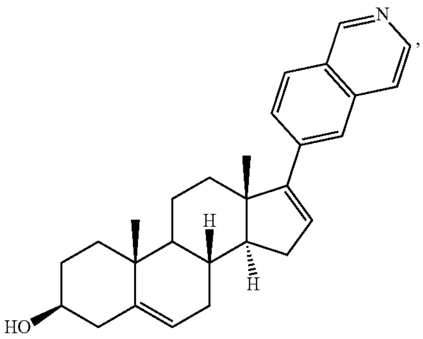

or a stereoisomer or pharmaceutically acceptable salt thereof.

14. A pharmaceutical composition comprising a therapeutically effective amount of the compound of claim 1, or a stereoisomer or pharmaceutically acceptable salt thereof, and a pharmaceutically acceptable carrier.

15. A method of treating a CDK8 and/or CDK19 mediated cancer in a subject comprising administering to the subject an effective amount of the compound of claim 1, or a stereoisomer or pharmaceutically acceptable salt thereof.

16. A compound which is:

(33)

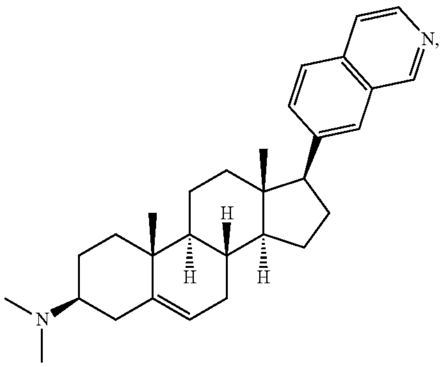

or a stereoisomer or pharmaceutically acceptable salt thereof.

17. A pharmaceutical composition comprising a therapeutically effective amount of the compound of claim 16, or a stereoisomer or pharmaceutically acceptable salt thereof, and a pharmaceutically acceptable carrier.

18. A method of treating a CDK8 and/or CDK19 mediated cancer in a subject comprising administering to the subject an effective amount of the compound of claim 16, or a stereoisomer or pharmaceutically acceptable salt thereof.

19. The method of claim 15, wherein the CDK8 and/or CDK19 mediated cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemia, lymphoma, myeloma, or a solid tumor.

20. The method of claim 18, wherein the CDK8 and/or CDK19 mediated cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemia, lymphoma, myeloma, or a solid tumor.

* * * * *